(12) United States Patent
Kobayashi et al.

(10) Patent No.: US 8,500,696 B2
(45) Date of Patent: Aug. 6, 2013

(54) METHOD OF PRODUCING INDWELLING NEEDLE ASSEMBLY AND INDWELLING NEEDLE ASSEMBLY

(75) Inventors: Ryoji Kobayashi, Nakakoma-gun (JP); Hidenori Tanabe, Nakakoma-gun (JP); Kazuhiro Hashimoto, Nakakoma-gun (JP); Takato Murashita, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 813 days.

(21) Appl. No.: 12/664,016

(22) PCT Filed: Mar. 28, 2008

(86) PCT No.: PCT/JP2008/056056
§ 371 (c)(1),
(2), (4) Date: Dec. 10, 2009

(87) PCT Pub. No.: WO2008/152849
PCT Pub. Date: Dec. 18, 2008

(65) Prior Publication Data
US 2010/0179478 A1    Jul. 15, 2010

(30) Foreign Application Priority Data

Jun. 12, 2007  (JP) .................................. 2007-155206
Jun. 25, 2007  (JP) .................................. 2007-166908
Jun. 26, 2007  (JP) .................................. 2007-168137
Jun. 26, 2007  (JP) .................................. 2007-168138

(51) Int. Cl.
*A61M 5/178* (2006.01)

(52) U.S. Cl.
USPC .................................................. 604/167.06

(58) Field of Classification Search
USPC ................. 604/167.01, 167.04, 167.06, 172, 604/507
See application file for complete search history.

(56) References Cited

U.S. PATENT DOCUMENTS 5,951,520 A    9/1999  Burzynski et al.
6,352,521 B1 *  3/2002  Prosl ........................ 604/167.03

(Continued)

FOREIGN PATENT DOCUMENTS

JP    10-272182 A    10/1998
JP    2001-502589 A   2/2001

(Continued)

OTHER PUBLICATIONS

International Search Report issued by the Japanese Patent Office on May 13, 2008 as the International Searching Authority in International Application No. PCT/JP2008/056056.

(Continued)

*Primary Examiner* — Nicholas Lucchesi
*Assistant Examiner* — Diva K Chander
(74) *Attorney, Agent, or Firm* — Buchanan Ingersoll & Rooney PC

(57) ABSTRACT

A method of producing an indwelling needle assembly formed by assembling an inner needle having a point only at its tip, an inner needle hub fixed to the base end of the inner needle, a hollow outer needle through which the inner needle is insertable, an outer needle hub fixed to the base end of the outer needle, and an elastic seal member on the outer needle hub effecting sealing when the inner needle is withdrawn. The method involves: inserting the inner needle into the seal member to set the inner needle to an inserted state; applying, in the inserted state, lubricant to the outer peripheral surface of at least that portion of the inner needle which protrudes from the seal member; and axially reciprocating at least one time the inner needle relative to the seal member to cause the lubricant to penetrate the inside of the seal member.

11 Claims, 31 Drawing Sheets

U.S. PATENT DOCUMENTS

| | | | |
|---|---|---|---|
| 2004/0068232 A1* | 4/2004 | Hart et al. | 604/167.06 |
| 2004/0267209 A1 | 12/2004 | Kunishige | |
| 2005/0192535 A1* | 9/2005 | Takagi et al. | 604/164.08 |
| 2008/0103449 A1 | 5/2008 | Murashita et al. | |
| 2010/0179478 A1* | 7/2010 | Kobayashi et al. | 604/167.01 |

FOREIGN PATENT DOCUMENTS

| | | |
|---|---|---|
| JP | 2005-261931 A | 9/2005 |
| JP | 2007-125126 A | 5/2007 |
| JP | 2007125126 A * | 5/2007 |
| WO | 03/041771 A1 | 5/2003 |
| WO | WO 2006/027923 A1 | 3/2006 |

OTHER PUBLICATIONS

Written Opinion of the International Searching Authority of Application No. PCT/JP2008/056056 dated May 13, 2008.

* cited by examiner

METHOD OF PRODUCING INDWELLING NEEDLE ASSEMBLY AND INDWELLING NEEDLE ASSEMBLY

TECHNICAL FIELD

The present invention relates to a method of producing an indwelling needle assembly and to an indwelling needle assembly produced by such a method.

BACKGROUND ART

When performing an infusion into a patient, or in other similar cases, an indwelling needle connected to an infusion line is made to puncture a blood vessel of the patient and to indwell within the blood vessel. The intended operation is conducted under this condition.

Such an indwelling needle includes a hollow outer needle, an outer needle hub firmly attached to a proximal end of the outer needle, an inner needle having a sharp needle point at its distal end and which is inserted through the outer needle, and an inner needle hub firmly attached to a proximal end of the inner needle (see, for example, International Publication No. WO 2006/027923 A1.

When the indwelling needle is made to puncture the patient's blood vessel, the puncturing operation is conducted in an assembled condition where the inner needle is inserted into the outer needle, and the needle point of the inner needle protrudes from the distal end of the outer needle. In the assembled condition, normally, the outer needle hub is connected with the connector of an infusion line.

Thereafter, when the needle point of the inner needle reaches the inside of the blood vessel, blood flowing in through the opening at the needle point passes through the lumen of the inner needle, and flows into the inside of a transparent inner needle hub (flashback). This enables confirmation (visual confirmation) that the inner needle has punctured the blood vessel securely.

After flashback is confirmed, the outer needle is advanced so that the outer needle becomes inserted into the blood vessel.

Next, while gripping the outer needle by hand, the inner needle is pulled out of the outer needle. Then, an infusion agent is dispensed through the infusion line and the outer needle, which are connected to each other.

Meanwhile, a seal member (plug body) is provided on (affixed to) the outer needle hub. The seal member has a slit through which the inner needle can be inserted and which is closed when the inserted inner needle is pulled out. In other words, the seal member has a self-closing property.

It has been a common practice that, when the indwelling needle having the seal member as mentioned above is set in an assembled condition by inserting the inner needle into and through the seal member, the inner needle is inserted into the seal member, starting with its easier-to-insert side, namely, starting with the needle point thereof. In this instance, there has been a fear that friction between the seal member and the needle point may be generated, resulting in damage to the needle point (chipping of the cutting edge). In addition, the insertion of the inner needle starting with the needle point thereof may cause the slit (seal member) to be unintentionally ruptured by the needle point. Unintentional rupture of the slit, if it occurs, may cause the slit, for example, to become deviated from its original shape. In this case, when the inner needle is pulled out from the seal member while using the indwelling needle assembly in an assembled condition, comparatively heavy friction may be generated between the seal member and the needle body, thus making it difficult to perform the pulling-out operation.

DISCLOSURE OF INVENTION

It is an object of the present invention to provide a method of producing an indwelling needle assembly such that the needle point of an inner needle can be protected during insertion of the inner needle into and through a seal member in order to assemble them together, and so that excellent operability is attained when the inner needle is pulled out from the seal member during use of the indwelling needle assembly in an assembled condition. The present invention further concerns an indwelling needle assembly produced by such a method.

(1) In order to attain the above object, the present invention provides:

a method of producing an indwelling needle assembly formed by assembling together an inner needle having a sharp needle point only at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom. The method of producing the indwelling needle assembly includes:

an insertion step for inserting the inner needle, with a side opposite to the needle point first, into and through the seal member so as to obtain an inserted condition;

a lubricant application step for applying, in the inserted condition, lubricant to an outer peripheral surface of at least a portion of the inner needle that protrudes from the seal member; and a reciprocation step for reciprocating at least one time the inner needle in an axial direction thereof relative to the seal member, so as to cause the lubricant to penetrate inside of the seal member.

This makes it possible to protect the needle point of the inner needle, at a time when the inner needle is inserted into and through the seal member in order to assemble them together. In addition, with the indwelling needle assembly in such an assembled condition, operability in pulling out the inner needle from the seal member during use of the assembly is excellent.

(2) Further, in the method of producing the indwelling needle assembly as described in (1) above, preferably, in the insertion step, insertion of the inner needle into and through the seal member is performed while the inner needle is rotated about its axis.

This enables the insertion operation to be carried out easily.

(3) In addition, in the method of producing the indwelling needle assembly as described in (1) above, preferably, the seal member preliminarily is formed with a slit therein, which permits the inner needle to be inserted therethrough.

This enables the operation of inserting the inner needle (insertion operation) to be carried out easily.

(4) Further, in the method of producing the indwelling needle assembly as described in (1) above, preferably, the indwelling needle assembly further includes a compression member mounted on the outer needle hub, and which accommodates the seal member therein and compresses an outer peripheral portion of the seal member; and the insertion step is carried out in a condition where the seal member is accommodated inside the compression member.

This ensures that the inner needle is compressed toward the center of the seal member, and therefore, that the inner needle can be inserted substantially in the center of the seal member.

(5) In addition, in the method of producing the indwelling needle assembly as described in (1) above, preferably, in the reciprocation step, a portion of the inner needle that corresponds to one end face of the seal member travels a distance sufficient to pass beyond the other end face of the seal member.

This ensures that the lubricant can assuredly be supplied to the inside of the seal member over the entire range thereof in the longitudinal direction. Therefore, frictional resistance between the inner needle and the seal member can be reduced assuredly.

(6) Further, in the method of producing the indwelling needle assembly as described in (1) above, preferably, in the reciprocation step, reciprocation of the inner needle relative to the seal member is performed while the inner needle is rotated about its axis.

This ensures that sliding resistance between the inner needle and the seal member during the reciprocating operation is reduced, to thereby facilitate the reciprocating operation.

(7) In addition, the method of producing the indwelling needle assembly as described in (1) above preferably includes, between the insertion step and the lubricant application step, an inner needle hub fixation step for fixing the inner needle hub to the proximal portion of the inner needle in the inserted condition.

This enables the inner needle hub to be fixed to the proximal portion of the inner needle in the inserted condition.

(8) Further, the method of producing the indwelling needle assembly as described in (1) above preferably includes, after the reciprocation step, an outer needle hub fixation step for fixing to the outer needle hub the seal member in the inserted condition.

This enables the seal member in the inserted condition to be fixed to the outer needle hub.

In addition, in the method of producing the indwelling needle assembly as described in (1) above, preferably, the lubricant application step is carried out by immersing the inner needle and the seal member in the inserted condition into the lubricant, which comprises a liquid.

This enables the lubricant to be applied (supplied) easily and assuredly to the outer peripheral surface of a portion of the inner needle that protrudes from the seal member.

Further, in the method of producing the indwelling needle assembly as described in (1) above, preferably, the reciprocation step is carried out after the inner needle and the seal member in the inserted condition have been drawn up from the lubricant.

This enables the reciprocating operation to be carried out easily.

In addition, in the method of producing the indwelling needle assembly as described in (1) above, preferably, the inner needle is provided with a marker thereon for enabling the distance traveled by the inner needle to be ascertained.

This enables the lubricant to be assuredly supplied to the interior of the seal member over the entire range along the longitudinal direction thereof. Therefore, frictional resistance between the inner needle and the seal member can be reduced more assuredly.

Further, in the method of producing the indwelling needle assembly as described in (1) above, preferably, the lubricant is composed mainly of silicone.

This ensures that the silicone, for example, remains on the surface of the inner needle for a long time, so that the effect thereof on friction between the inner needle and the seal member is maintained.

(9) In order to attain the above object, the present invention also provides:

an indwelling needle assembly produced by the method as described in any of (1) to (8) above.

This makes it possible to protect the needle point of the inner needle at a time when the inner needle is inserted into and through the seal member in order to assemble them together. In addition, the indwelling needle assembly in the assembled condition is excellent in operability, at a time when the inner needle is pulled out from the seal member during use of the indwelling needle assembly.

(10) In order to attain the above object, the present invention also provides:

a method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom, the method of producing the indwelling needle assembly including:

a jig insertion step for inserting a jig that permits the inner needle to be inserted therethrough into and through the seal member, so as to obtain a jig-inserted condition;

a lubricant application step for applying lubricant to at least a portion of the outer peripheral surface of the inner needle that corresponds to the seal member when the inner needle and the seal member are assembled together;

an inner needle insertion step for inserting the inner needle, with the lubricant applied thereto, into and through the inside of the jig in the jig-inserted condition; and a jig pulling-out step for moving the jig along an axial direction relative to the inner needle and the seal member in order to pull out the jig.

This makes it possible to protect the needle point of the inner needle upon inserting the inner needle into and through the seal member to assemble them together. Further, the indwelling needle assembly in the assembled condition is excellent in operability at a time when the inner needle is pulled out from the seal member during use of the indwelling needle assembly.

(11) In addition, in the method of producing the indwelling needle assembly as described in (10) above, preferably, the lubricant is a liquid, and the lubricant application step is carried out by immersion.

This enables the lubricant to be applied (supplied) easily and assuredly to the outer peripheral surface of the inner needle, and in particular, to the outer peripheral surface of a part corresponding to the seal member in the assembled condition.

(12) In order to attain the above object, the present invention provides:

a method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom, the method of producing the indwelling needle assembly including:

a jig insertion step for inserting a jig that permits the inner needle to be inserted therethrough into and through the seal member, so as to obtain a jig-inserted condition;

a lubricant filling step for filling the inside of the jig with a lubricant;

a lubricant application step for inserting the inner needle into and through the inside of the jig, which is in the jig-inserted condition and filled with the lubricant, so as to apply the lubricant to at least a portion of the outer peripheral surface of the inner needle that corresponds to the seal member when the inner needle and the seal member are assembled together; and a jig pulling-out step for moving the jig along an axial direction relative to the inner needle and the seal member in order to pull out the jig.

This makes it possible to protect the needle point of the inner needle during insertion of the inner needle into and through the seal member to assemble them together. In addition, the indwelling needle assembly in the assembled condition is excellent in operability at a time when the inner needle is pulled out from the seal member during use of the indwelling needle assembly.

(13) In order to attain the above object, the present invention provides:

a method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom, the method of producing the indwelling needle assembly including:

a jig insertion step for inserting a jig that permits the inner needle to be inserted therethrough into and through the seal member, so as to obtain a jig-inserted condition;

an inner needle insertion step for inserting the inner needle into and through the inside of the jig in the jig-inserted condition;

a lubricant application step for filling a gap between the inside of the jig and the inner needle with a lubricant, so as to apply the lubricant to at least a portion of the outer peripheral surface of the inner needle that corresponds to the seal member when the inner needle and the seal member are assembled together; and a jig pulling-out step for moving the jig along an axial direction thereof relative to the inner needle and the seal member in order to pull out the jig.

This makes it possible to protect the needle point of the inner needle at the time of insertion of the inner needle into and through the seal member to assemble them together. Further, the indwelling needle assembly in the assembled condition is excellent in operability at the time when the inner needle is pulled out from the seal member during use of the indwelling needle assembly.

(14) In addition, in the method of producing the indwelling needle assembly as described in (12) or (13) above, preferably, the lubricant is a liquid, and filling with the lubricant is carried out by use of an injection container preliminarily filled with the liquid lubricant, and by injection from the injection container.

This enables the lubricant to be applied (supplied) easily and assuredly to the outer peripheral surface of the inner needle, and in particular, to an outer peripheral surface of a part corresponding to the seal member in the assembled condition.

(15) Further, in the method of producing the indwelling needle assembly as described in (10), (12) or (13) above, preferably, the indwelling needle assembly further includes a compression member mounted on the outer needle hub, and which accommodates the seal member therein and compresses an outer peripheral portion of the seal member; and the jig insertion step is carried out in a condition where the seal member is accommodated inside the compression member.

This ensures that pressure from the compression member is directed toward the center axis of the seal member, and therefore, that the inner needle can be located in the center.

(16) In addition, the method of producing the indwelling needle assembly as described in (10), (12) or (13) above preferably includes an inner needle hub fixation step for fixing the inner needle hub to the proximal portion of the inner needle, prior to the jig insertion step.

This enables the inner needle hub to be fixed to the inner needle.

(17) Further, the method of producing the indwelling needle assembly as described in (10), (12) or (13) above preferably includes an outer needle hub fixation step for fixing the seal member to the outer needle hub, after the jig pulling-out step.

This enables the seal member to be fixed to the outer needle hub.

(18) In addition, in the method of producing the indwelling needle assembly as described in (10), (12) or (13) above, preferably, the lubricant is comprised mainly of silicone.

This ensures that the silicone, for example, remains on the surface of the inner needle for a long time, and therefore, the effect of the silicone on reducing friction between the inner needle and the seal member is maintained.

Further, in the method of producing the indwelling needle assembly as described in (10), (12) or (13) above, preferably, the seal member is block-like in shape; and the seal member is preliminarily formed with a slit through which the jig is inserted in the jig assembled condition, and through which the inner needle is inserted in a condition where the seal member is assembled with the inner needle.

This enables the operation of inserting the jig (insertion operation) to be carried out easily.

In addition, in the method of producing the indwelling needle assembly as described in (10), (12) or (13) above, preferably, the jig is provided, at an end portion thereof on a side that is inserted into the seal member, with a part having an outside diameter that decreases gradually toward the side being inserted.

This ensures that in inserting the jig into the seal member (during the jig insertion step), the insertion operation can be carried out easily.

Further, in the method of producing the indwelling needle assembly as described in (10), (12) or (13) above, preferably, the jig is formed from a metallic material.

This ensures that the jig can have appropriate rigidity, and that insertion of the jig through (into) the seal member during the jig insertion step can be carried out easily and assuredly.

In addition, in the method of producing the indwelling needle assembly as described in (10), (12) or (13) above, preferably, the jig may be reused at a time of producing an indwelling needle assembly separate from the above-mentioned indwelling needle assembly.

This ensures that preparation of an unused jig each time that an indwelling needle assembly is produced can be avoided.

Further, in the method of producing the indwelling needle assembly as described in (10), (12) or (13) above, preferably, in the jig insertion step, insertion of the jig into and through the seal member is performed while the jig is rotated about its axis.

This enables the insertion operation to be carried out more easily.

In addition, in the method of producing the indwelling needle assembly as described in (10), (12) or (13) above, preferably, in the jig pulling-out step, pulling-out of the jig is performed while rotating the jig about its axis.

This enables the pulling-out operation to be carried out more easily.

Further, the method of producing the indwelling needle assembly as described in (10), (12) or (13) above preferably includes a reciprocation step, for reciprocating the inner needle in an axial direction thereof relative to the jig, at least one time prior to the jig pulling-out step.

This enables the lubricant to be applied evenly to the outer peripheral surface of the inner needle over a comparatively wide range.

(19) In order to attain the above object, the present invention further provides:

an indwelling needle assembly produced by the method described in any of (10) to (18) above.

This makes it possible to protect the needle point of the inner needle at a time when the inner needle is inserted into and through the seal member in order to assemble them together. In addition, the indwelling needle assembly in the assembled condition is excellent in operability when the inner needle is pulled out from the seal member during use of the indwelling needle assembly.

(20) In order to attain the above object, the present invention provides:

a method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, and having a slit that permits the inner needle to be inserted therethrough, the slit exhibiting a sealing function when the inner needle is pulled out therefrom, the method of producing the indwelling needle assembly including:

an insertion step for inserting the inner needle, with a side opposite to the needle point first, into and through the slit to obtain an inserted condition;

a slit opening step for opening the slit in the inserted condition; and a lubricant supplying step for supplying a lubricant into the opened slit to apply the lubricant to the inner surface of the slit and to a portion of the outer peripheral surface of the inner needle that is located inside the slit.

This makes it possible to protect the needle point of the inner needle at a time of inserting the inner needle into and through the seal member to assemble them together. Further, the indwelling needle assembly in the assembled condition is excellent in operability at a time when the inner needle is pulled out from the seal member during use of the indwelling needle assembly.

(21) In addition, in the method of producing the indwelling needle assembly as described in (20) above, preferably, in the insertion step, insertion of the inner needle into and through the seal member is carried out while rotating the inner needle about its axis.

This enables the insertion operation to be carried out more easily.

(22) Further, in the method of producing the indwelling needle assembly as described in (20) above, preferably, the slit has a portion formed in the shape of a straight line; and compression in the formation direction of the straight line-shaped portion, or in a direction inclined at a predetermined angle with respect to a formation direction, is performed in the slit opening step.

This ensures that the slit is opened assuredly, thus resulting in generation of a gap between the inner surface of the slit and the outer peripheral surface of the inner needle.

(23) In addition, in the method of producing the indwelling needle assembly as described in (20) above, preferably, the lubricant is a liquid; and the lubricant supply step is carried out by immersion.

This enables the lubricant to be assuredly applied not only to the part of the inner needle that protrudes from the seal member, but also to inner surfaces of the slit and to a portion of the outer surface of the inner needle that is located within the slit.

(24) Further, in the method of producing the indwelling needle assembly as described in (20) above, preferably, the lubricant is a liquid; and the lubricant supply step is carried out by use of an injection container, which is preliminarily filled with the liquid lubricant, and by injection from the injection container.

This enables the lubricant to be applied assuredly to inner surfaces of the slit and to a part of the outer surface of the inner needle that is located in the slit.

(25) In addition, the method of producing the indwelling needle assembly as described in (20) above preferably includes, after the insertion step, an inner needle hub fixation step for fixing the inner needle hub to the proximal portion of the inner needle in the inserted condition.

This enables the inner needle hub to be fixed to the inner needle.

(26) Further, the method of producing the indwelling needle assembly as described in (20) above preferably includes, after the lubricant supply step, a lubricant penetration step for causing the lubricant to further penetrate into the slit.

This ensures that the lubricant further penetrates into the slit, or stated otherwise, penetration of the lubricant into the slit is promoted. Therefore, the slit can be supplied assuredly with the lubricant over an entire range along the longitudinal direction thereof.

(27) In addition, in the method of producing the indwelling needle assembly as described in (20) above, preferably, the indwelling needle assembly further has a compression member mounted on the outer needle hub and accommodating the seal member therein, and compresses an outer peripheral portion of the seal member; and the method includes, after the lubricant supply step, a seal member accommodation step for accommodating the seal member into the compression member in the inserted condition.

This ensures that pressure from the compression member is directed toward the center axis of the seal member, so that the inner needle can be located in the center.

(28) Further, the method of producing the indwelling needle assembly as described in (20) above preferably includes, after the lubricant supply step, an outer needle hub fixation step for fixing the seal member to the outer needle hub in the inserted condition.

This enables the seal member to be fixed to the outer needle hub in the inserted condition.

In addition, in the method of producing the indwelling needle assembly as described in (20) above, preferably, the inner needle is provided at a proximal portion thereof with a part where the outside diameter decreases gradually along the proximal direction.

This ensures that when the inner needle is inserted, with the proximal portion thereof first, into and through the slit in the seal member, the operation can be carried out easily.

Further, in the method of producing the indwelling needle assembly as described in (20) above, preferably, the slit opening step is performed by compressing the seal member in directions so as to open the slit.

This ensures that the slit is opened assuredly, resulting in generation of a gap between the inner surface of the slit and the outer peripheral surface of the inner needle.

In addition, in the method of producing the indwelling needle assembly as described in (20) above, preferably, the lubricant is comprised mainly of silicone.

This ensures that the silicone, for example, remains on the surface of the inner needle for a long time, so that the effect thereof to reduce friction between the inner needle and the seal member is maintained.

(29) In order to attain the above object, the present invention provides:

an indwelling needle assembly produced by the method according to any of (20) to (28) above.

This makes it possible to protect the needle point of the inner needle at a time when the inner needle is inserted into and through the seal member to assemble them together. In addition, the indwelling needle assembly in the assembled condition is excellent in operability at a time when the inner needle is pulled out from the seal member during use of the indwelling needle assembly.

(30) In order to attain the above object, the present invention provides:

a method of producing an indwelling needle assembly formed by assembling together an inner needle having a sharp needle point only at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material, provided on the outer needle hub, for permitting the inner needle to be inserted therethrough, and exhibiting a sealing function when the inner needle is pulled out therefrom, the method of producing the indwelling needle assembly including:

an immersion step for immersing the inner needle and the seal member in nanobubble water containing nanobubbles;

an insertion step for inserting, in the nanobubble water, the inner needle, with a side opposite to the needle point first, into and through the seal member so as to obtain an inserted condition;

a pulling-up step for pulling the inner needle and the seal member in the inserted condition up from the nanobubble water;

a lubricant application step for applying, in the inserted condition, lubricant to the outer peripheral surface of at least a portion of the inner needle that protrudes from the seal member; and a reciprocation step for reciprocating at least one time the inner needle in an axial direction thereof relative to the seal member, so as to cause the lubricant to penetrate inside of the seal member.

This makes it possible to protect the needle point of the inner needle when the inner needle is inserted into and through the seal member to assemble them together. Further, the indwelling needle assembly in the assembled condition is excellent in operability at a time when the inner needle is pulled out from the seal member during use of the indwelling needle assembly.

(31) In addition, in the method of producing the indwelling needle assembly as described in (30) above, preferably, in the insertion step, insertion of the inner needle into and through the seal member is carried out while rotating the inner needle about its axis.

This enables the insertion operation to be carried out easily.

(32) Further, in the method of producing the indwelling needle assembly as described in (30) above, preferably, the seal member is block-like in shape; and the seal member is preliminarily formed with a slit therein that permits the inner needle to be inserted therethrough.

This enables the operation of inserting the inner needle (insertion operation) to be carried out easily.

(33) In addition, in the method of producing the indwelling needle assembly as described in (30) above, preferably, the lubricant is a liquid; and the lubricant application step is carried out by immersion.

This enables the lubricant to be applied (supplied) easily and assuredly to the outer peripheral surface of a part of the inner needle that protrudes from the seal member.

(34) Further, in the method of producing the indwelling needle assembly as described in (30) above, preferably, in the reciprocation step, a portion of the inner needle that corresponds to one end face of the seal member travels a distance sufficient to pass beyond the other end face of the seal member.

This enables the lubricant to be supplied assuredly into the interior of the seal member over the entire range thereof along the longitudinal direction. Therefore, frictional resistance on the inner needle can be reduced more assuredly.

(35) In addition, in the method of producing the indwelling needle assembly as described in (30) above, preferably, the indwelling needle assembly further includes a compression member mounted to the outer needle hub, which accommodates the seal member therein and compresses an outer peripheral portion of the seal member; and the method comprises, after the reciprocation step, a seal member accommodation step for accommodating the seal member inside the compression member in the inserted condition.

This ensures that pressure from the compression member is directed toward the center axis of the seal member, whereby the inner needle can be located in the center.

(36) Further, the method of producing the indwelling needle assembly as described in (30) above preferably includes, after the reciprocation step, an inner needle hub fixation step for fixing the inner needle hub to the proximal portion of the inner needle in the inserted condition.

This enables the inner needle hub to be fixed to the inner needle when the inner needle is in the inserted condition.

(37) In addition, the method of producing the indwelling needle assembly as described in (36) above preferably includes, after the inner needle hub fixation step, an outer needle hub fixation step for fixing the seal member to the outer needle hub in the inserted condition.

This ensures that the seal member in the inserted condition can be fixed to the outer needle hub.

Further, in the method of producing the indwelling needle assembly as described in (30) above, preferably, the inner needle is provided at a proximal portion thereof with a part where the outside diameter decreases gradually along the proximal direction of the inner needle.

This ensures that when the inner needle is inserted with its proximal portion first into and through the seal member, the operation can be performed easily.

In addition, in the method of producing the indwelling needle assembly as described in (30) above, preferably, the lubricant is composed mainly of silicone.

This ensures that the silicone, for example, remains on the surface of the inner needle for a long time. Therefore, the effect of the silicone to reduce friction between the inner needle and the seal member is maintained.

(38) In order to attain the above object, the present invention provides:

an indwelling needle assembly produced by any of (30) to (37) above.

This makes it possible to protect the needle point of the inner needle at the time of inserting the inner needle into and through the seal member in order to assemble them together. In addition, the indwelling needle assembly in the assembled condition is excellent in operability at a time when the inner needle is pulled out from the seal member during use of the indwelling needle assembly.

BEST MODE FOR CARRYING OUT THE INVENTION

Next, a method of producing an indwelling needle assembly, and an indwelling needle assembly, according to the present invention will be described in detail below, based on preferred embodiments of the present invention as shown in the accompanying drawings.

<First Embodiment>

Figure 1:
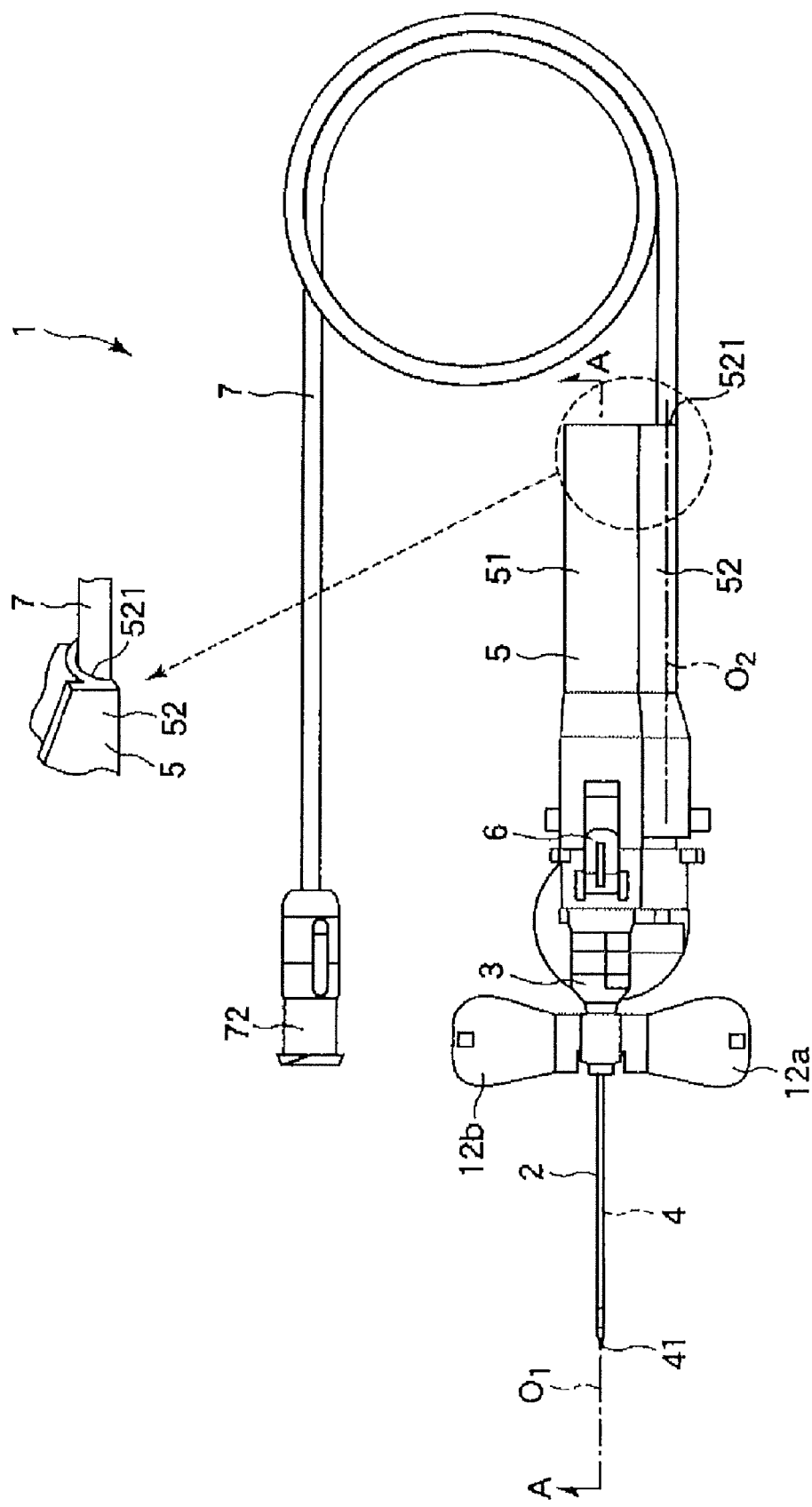
FIG. 1 is a plan view of an embodiment of the indwelling needle assembly according to the present invention.
Figure 2:
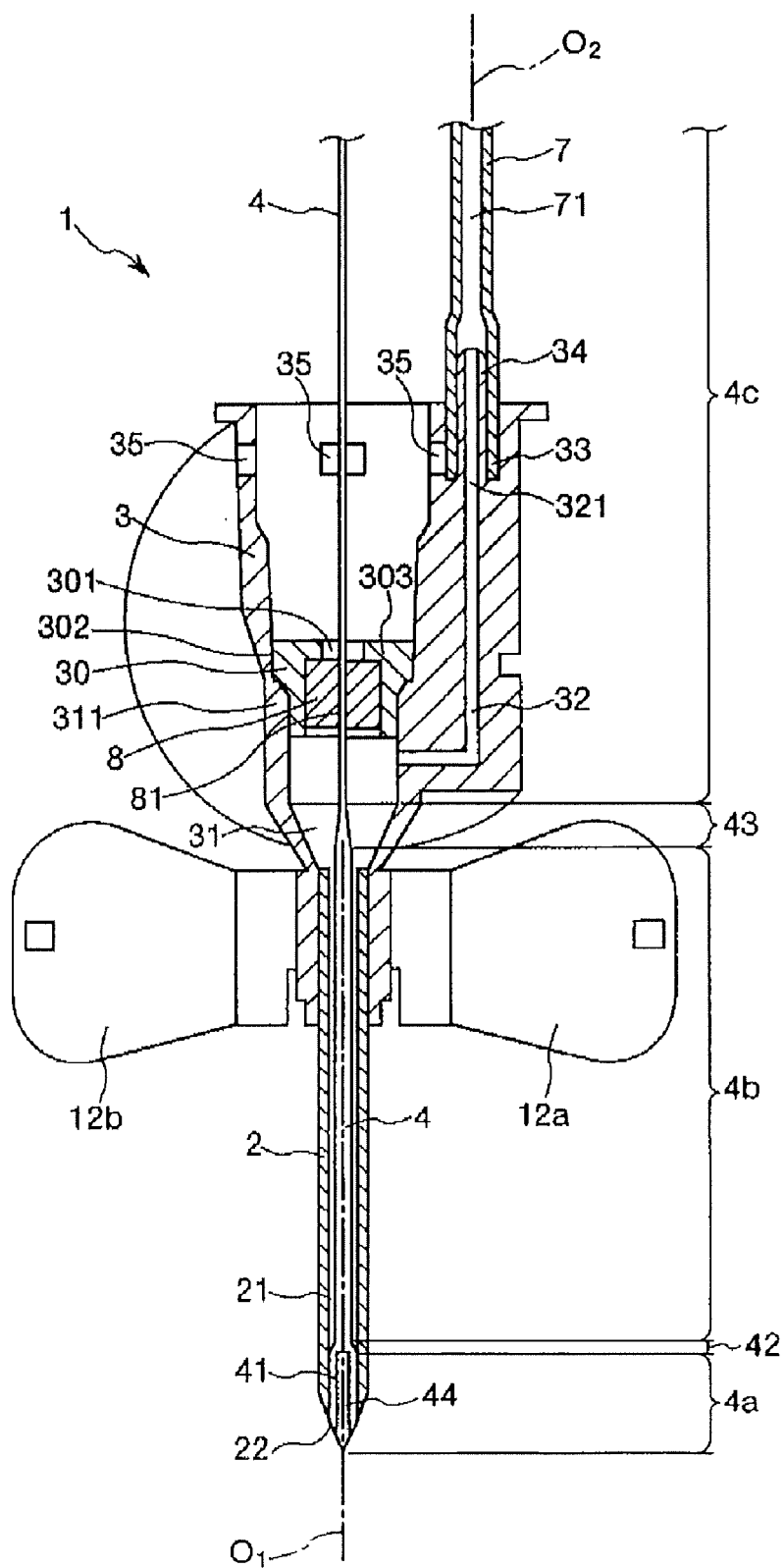
FIG. 2 is a longitudinal sectional view showing an outer needle, an outer needle hub, an inner needle and a tube of the indwelling needle assembly shown in FIG. 1.
Figure 3:
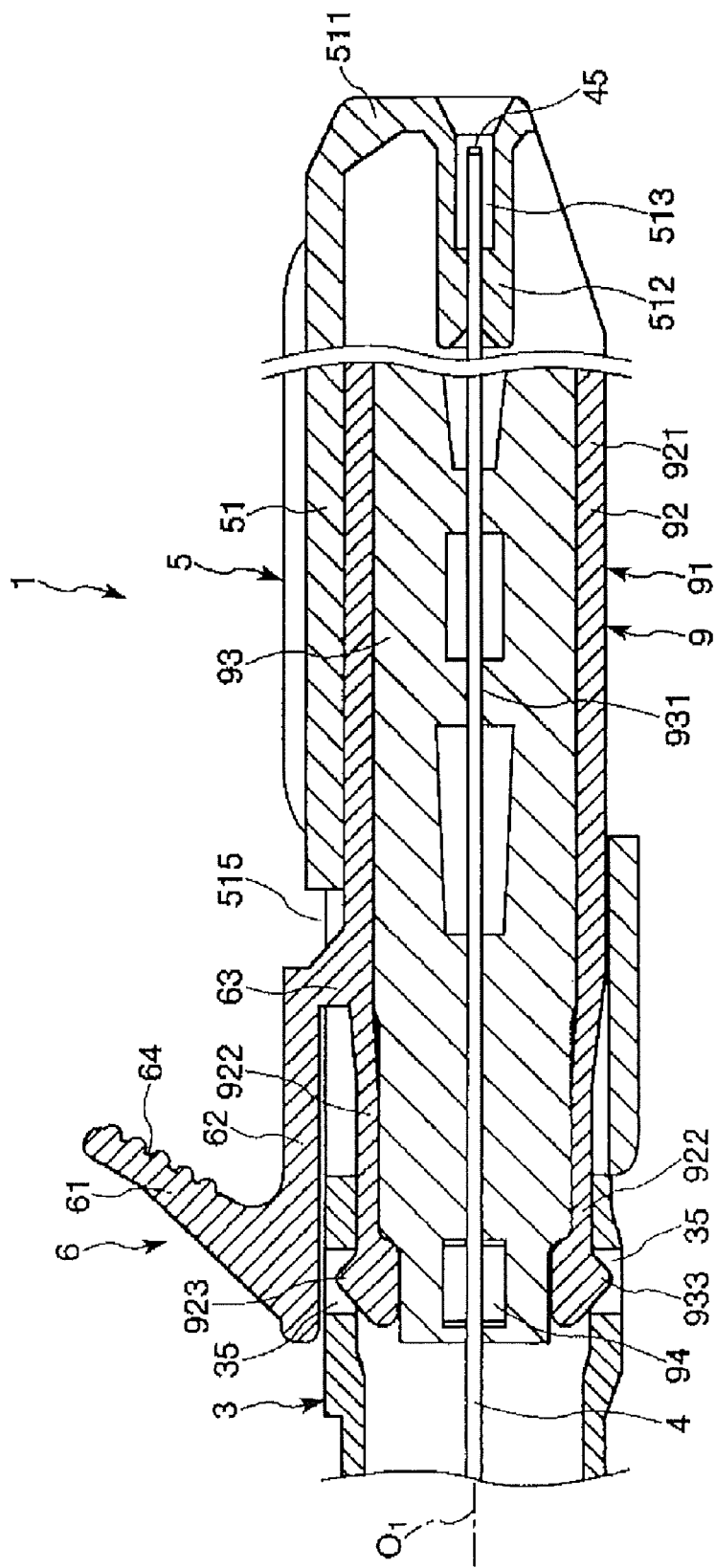
FIG. 3 is a sectional view taken along line A-A of FIG. 1.
Figure 4:
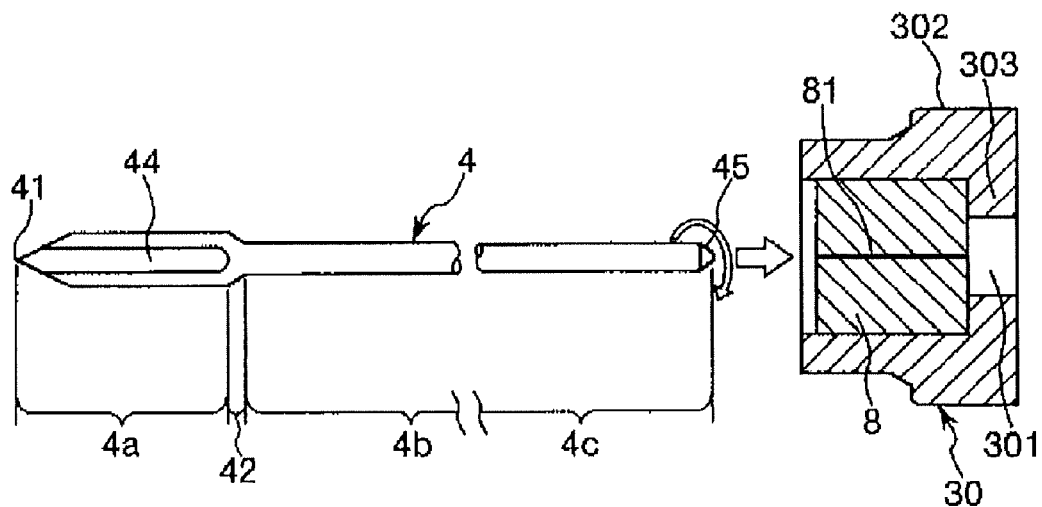
FIG. 4 is a drawing (longitudinal sectional view) for sequentially illustrating steps (first embodiment) for producing the indwelling needle assembly shown in FIG. 1.

FIG. 1 is a plan view showing an embodiment of the indwelling needle assembly according to the present invention; FIG. 2 is a longitudinal sectional view showing an outer needle, an outer needle hub, an inner needle and a tube of the indwelling needle assembly shown in FIG. 1; FIG. 3 is a sectional view taken along line A-A of FIG. 1; and FIGS. 4 to 9 are drawings (longitudinal sectional views) for sequentially illustrating steps (first embodiment) for producing the indwelling needle assembly shown in FIG. 1. Incidentally, in the following descriptions, the right side in FIGS. 1, 3 to 6, 8 and 9 shall be referred to as "proximal," the left side in the figures as "distal," the upper side in FIG. 2 as "proximal," and the lower side in the figure as "distal." Moreover, in FIG. 2, the inner needle hub has been omitted from the drawing.

The indwelling needle assembly 1 shown in FIGS. 1 to 3 includes a hollow outer needle 2, an outer needle hub 3 affixed to a proximal portion of the outer needle 2, a compression member 30 mounted to the outer needle hub 3, a seal member 8 provided on the outer needle hub 3 through the compression member 30, an inner needle 4 inserted in the outer needle 2, an inner needle hub 5 fixed to a proximal portion 45 of the inner needle 4, and a tube 7 connected to a proximal portion (or to a side portion) of the outer needle hub 3, so that a lumen 71 thereof communicates with a lumen 21 of the outer needle 2. The indwelling needle assembly 1 is produced by assembling these members together by a production method, which will be described later.

As the outer needle 2, a needle having a certain degree of flexibility preferably is used. The material used in forming the outer needle 2 preferably is a resin material, and more particularly, a flexible resin material. Specific examples of the resin material include fluororesins such as PTFE, ETFE, PFA, etc., olefin resins such as polyethylene, polypropylene, etc., or mixtures thereof, polyurethane, polyesters, polyamides, polyether-nylon resin, and mixtures of olefin resins with an ethylene-vinyl acetate copolymer, and so on.

The outer needle 2 may wholly or partially enable the inside thereof to be visible. Further, the material constituting the outer needle 2 may contain a radiopaque material such as barium sulfate, barium carbonate, bismuth carbonate, tungstic acid, etc., blended therein to attain a radiopacity function.

The outer needle hub 3 is firmly attached (affixed) in a liquid-tight manner to a proximal portion of the outer needle 2, by a method such as caulking, fusing (heat fusing, microwave fusing, etc.), adhesion with an adhesive, or the like.

The outer needle hub 3 is comprised of a substantially tubular member, the inside 31 of which communicates with the lumen 21 of the outer needle 2.

The outer needle hub 3 is provided, at a portion (part) thereof on the right side in FIG. 2, with a flow passage 32 opening at one end into the inside 31 of the outer needle hub 3. The flow passage 32 is substantially L-shaped, and the other end thereof opens at a recess 33 formed in a recessed form in the proximal end of the outer needle hub 3, thereby forming an opening 321. In addition, at a distal end surface (bottom surface) of the recess 33, an annular projected part (connecting part) 34 is formed, which protrudes in the proximal direction surrounding the opening 321.

The projected part 34 is inserted into the lumen 71 of a distal portion of the tube 7, such that one end portion (a distal portion) of the tube 7 is connected to the outer needle hub 3. This enables a liquid, such as a medical liquid, to be supplied through the tube 7 into the outer needle 2 (the outer needle hub 3).

Further, on the left and right sides of the outer needle hub 3, as shown in FIG. 2, a pair of wings 12a and 12b are formed by linking (assembling) the outer needle hub 3 with component parts separate from the outer needle hub 3, or by forming such wings integrally with the outer needle hub 3. The wings 12a and 12b have flexibility, and can be opened and closed by bending or curving portions thereof in the vicinity of joints between the wings 12a and 12b and the outer needle hub 3.

In the case where the outer needle 2 and the inner needle 4 are made to collectively puncture a blood vessel or the like, the puncturing operation can be performed by pinching the wings 12a, 12b with the fingers, so as to set the wings 12a, 12b in a closed state. In addition, the puncturing operation may also be conducted by pinching the inner needle hub 5 with the thumb and middle finger, instead of pinching the wings 12a, 12b. In this case, when the distal end of the outer needle 2 has entered into the blood vessel, a finger hook part 6 to be described later is pushed with the index finger in order to advance the outer needle hub 3, whereby only the outer needle 2 can be advanced into the blood vessel. When the outer needle 2 is left in an indwelling state, the wings 12a and 12b are placed in an opened state, and the wings 12a and 12b are fixed to the skin by means of a pressure sensitive adhesive tape or the like.

Further, in a proximal portion of the outer needle hub 3, four holes (recesses) 35 are provided, into which projections 923 of four projected parts 922 of a protector cover 92 of a protector 9 (described later) are to be inserted, the four holes 35 being formed at regular angular intervals around the axis of the outer needle 2.

The inner needle 4, which has a sharp needle point 41 only at the distal end thereof, is inserted into the outer needle 2. The indwelling needle assembly 1 is used in the condition where the inner needle 4 is inserted through the outer needle 2, and where the inner needle hub 5, described later, and the outer needle hub 3 abut against each other (in a condition where the needle point 41 protrudes from a distal end opening 22 of the outer needle 2), i.e., the condition shown in FIGS. 1 and 2. Hereinafter, this condition shall be referred to as an "assembled condition."

The length of the inner needle 4 is set substantially so that, in the assembled condition, at least the needle point 41 protrudes from the distal end opening 22 of the outer needle 2.

The inner needle 4 may be a hollow needle, or may also be a solid needle. If the inner needle 4 is a solid needle, sufficient strength can be secured while adopting a reduced outside diameter. In addition, when the inner needle 4 is a solid needle, there is no danger of blood remaining inside the inner needle 4, or of blood flowing out from the inner needle 4, at a time of discarding the inner needle 4 after an operation is finished. Thus, high safety is ensured.

On the other hand, in the case that the inner needle 4 is a hollow needle, blood flows into a hollow portion of the inner needle 4 upon puncturing a blood vessel with the inner needle 4, thus enabling flashback of the blood to be confirmed. In this connection, when the inner needle 4 is a solid needle, blood flows into a gap formed between the inner needle 4 and the outer needle 2, which also enables earlier confirmation of blood flashback.

Incidentally, although the inner needle 4 can be formed in a configuration in which it has both a hollow portion and a solid portion (e.g., a configuration in which a lumen of the hollow needle is partially filled, so that the needle is hollow on the distal side and solid on the proximal side), forming the inner needle 4 entirely of a single member leads to a reduction in cost of the inner needle 4.

In addition, the inner needle 4 may be constant in outside diameter. As shown in the figures, however, the inner needle 4 has a plurality of parts (three in the present embodiment), which differ in outside diameter. More specifically, the inner needle 4 has a maximum outside diameter part 4a, which is largest in outside diameter and located on the distal side (distal portion), a minimum outside diameter part 4c, which is smallest in outside diameter and located on the proximal side, and an intermediate outside diameter part 4b, which has an outside diameter between the maximum outside diameter part 4a and the minimum outside diameter part 4c, and which is located between the parts 4a and 4c.

Further, the inner needle 4 is provided with a first varying outside diameter part 42, which varies continuously in outside diameter, at a boundary portion between the maximum outside diameter part 4a and the intermediate outside diameter part 4b, as well as a second varying outside diameter part 43, which varies continuously between the intermediate outside diameter part 4b and the minimum outside diameter part 4c.

While the outside diameter of the inner needle 4 may vary stepwise in each of the varying outside diameter parts 42 and 43, a structure wherein the outside diameter varies continuously (in a tapered form) ensures, when the inner needle 4 is pulled out from the outer needle 2, that each of the varying outside diameter parts 42 and 43 can be prevented from becoming caught on a distal edge portion of the slit 81 in the seal member 8, described later, or on the protector 9 or the like, so that pulling of the inner needle 4 out of the outside needle 2 can be carried out more smoothly and assuredly.

Incidentally, the varying outside diameter parts 42 and 43 may be formed at the time when the inner needle 4 is produced, or may be formed by utilizing steps which are necessarily performed during forming a groove 44, to be described later.

In addition, the maximum outside diameter part 4a has an outside diameter set approximately equal to the inside diameter of the outer needle 2, thereby making firm contact with the inner surface of the outer needle 2 in a condition where the inner needle 4 is inserted through the outer needle 2. The maximum outside diameter part 4a (distal portion) is provided on an outer peripheral portion, with the groove (flow passage) 44 extending along the longitudinal direction of the inner needle 4 in a recessed manner. The groove 44 ensures that the distal end opening 22 of the outer needle 2 and the inside 31 of the outer needle hub 3 communicate with each other in a condition where the inner needle 4 is inserted through the outer needle 2. The groove 44 functions as a blood (body fluid) flow passage, for example, when a blood vessel is punctured. Consequently, flashback of blood can be confirmed securely.

Examples of materials for the aforementioned inner needle 4 include metallic materials, such as stainless steel, aluminum or aluminum alloys, titanium or titanium alloys, etc.

The inner needle hub 5 is firmly attached (affixed) to the proximal portion 45 of the inner needle 4. As shown in FIG. 1, the inner needle hub 5 has a tubular protector accommodating part (link member accommodating part) 51 through which the inner needle 4 is inserted, and in which the protector 9 is accommodated (disposed) in the assembled condition, and a tube accommodating part 52, which is disposed on a lateral side (lower side in FIG. 1) of the protector accommodating part 51, and in which the distal side of the tube 7 is accommodated (disposed) in the assembled condition.

As shown in FIG. 3, the protector accommodating part 51 is formed with a proximal end wall 511 at a proximal end thereof. The proximal end wall 511 is formed with a projected part (fixing part) 512, which projects in the distal direction. The projected part 512 is provided with a hole 513, into which the proximal portion 45 of the inner needle 4 is inserted. The proximal portion 45 of the inner needle 4 is inserted into the hole 513, so as to become firmly attached (affixed) to the projected part 512.

Further, the protector 9 is located inside the protector accommodating part 51 in the assembled condition, and can be moved relative to the protector accommodating part 51.

In addition, in the assembled condition, the tube 7 is inserted through the tube accommodating part 52 of the inner needle hub 5, whereby the tube 7 can be prevented from obstructing operations of the indwelling needle assembly 1 (see FIG. 1).

Herein, the tube accommodating part 52 is formed with a groove 521 therein, and the tube 7 is disposed inside the groove 521. A portion (part) defining (forming) the groove 521 functions as a guide means for guiding the tube 7. The guide means, or the portion that defines the groove 521, guides the tube 7 so that the center axis (axis) $O_2$ at a distal part of the tube 7 is set substantially parallel to the longitudinal direction of the inner needle hub 5 (the center axis $O_1$ of the outer needle 2).

Thus, the tube 7 is connected to a proximal portion of the outer needle hub 3, and is configured such that the center axis $O_1$ of the outer needle 2 and the center axis $O_2$ at the distal portion of the tube 7 are substantially parallel with each other in the assembled condition. In other words, the tube 7 protrudes in the proximal direction from the proximal end of the outer needle hub 3.

In addition, in the case that the tube 7 is detached from the inner needle hub 5 upon pulling the inner needle 4 out from the outer needle 2, the tube 7 can easily and speedily be detached owing to the groove 521 (i.e., by passing through the groove 521).

Examples of methods for fixing the inner needle 4 to the inner needle hub 5 include methods such as fitting, caulking, fusing, adhesion with an adhesive, etc., as well as combinations of such methods. Further, in the case that the inner needle 4 is hollow, it is necessary to provide a seal, so that blood which flows back, for example upon puncturing a blood vessel, is prevented from flying out from the proximal end of the inner needle 4.

The aforementioned inner needle hub 5 and outer needle hub 3 each are preferably formed from a transparent (colorless transparent), colored transparent, or translucent resin, whereby the inside thereof is made visible. This makes it possible to visually confirm flashback of the blood that flows in through the aforementioned groove 44 of the inner needle 4, upon puncturing of a blood vessel by the outer needle 2. In addition, if the inner needle 4 is solid, the entirety of the blood that undergoes flashback, for example, due to the pressure inside the blood vessel, flows back through the groove 44, so that better visibility (visual confirmation) thereof can be realized.

Materials for the outer needle hub 3, the inner needle hub 5, and the wings 12a, 12b are not particularly limited. Examples of usable materials include various resin materials, including polyolefins such as polyethylene, polypropylene, ethylene-vinyl acetate copolymer, etc., polyurethane, polyamides, polyesters, polycarbonate, polybutadiene, polyvinyl chloride, polyacetal, etc.

The tube 7 is flexible, and, as previously mentioned, one end of the tube 7 is connected to the proximal portion of the outer needle hub 3. The other end portion (proximal portion) of the tube 7 is connected by means of a connector 72 (see FIG. 1). The connector 72 may be connected, for example, to a connector, which is mounted on an end portion of an infusion line through which an infusion (medical liquid) to be dispensed is supplied, an opening (distal portion) of a syringe containing a medical liquid therein, or the like.

Incidentally, material for the tube 7 is not particularly limited. Examples of usable materials include polyolefins such as polyethylene, polypropylene, ethylene-vinyl acetate copolymer, etc., polyvinyl chloride, polybutadiene, polyamides, polyesters, etc., among which polybutadiene is particularly preferred. In the case that polybutadiene is used as the material for the tube 7, appropriate flexibility, chemical resistance, and excellent medicine adsorption preventative properties are obtained.

In addition, in the indwelling needle assembly 1, the seal member 8, which is cylindrical (block-like) in shape, is disposed at the inside 31 of the outer needle hub 3 through the compression member 30. The seal member 8 is provided with the slit 81 therein, through which the inner needle 4 can be inserted, and which closes, i.e., exhibits a sealing function, upon pulling-out of the inserted inner needle 4. The slit 81 is formed substantially in the center of the seal member 8, so as to penetrate through the seal member 8 in the longitudinal direction thereof.

The slit 81 is in the shape of a straight line. This enables the slit 81 to be placed in an opened state easily from a closed condition. Therefore, the inner needle 4 can be inserted through the seal member 8 (the slit 81) smoothly, or in other words, when the outer needle 2 is advanced with the inner needle 4 serving as a guide, as will be described later, frictional resistance between the outer surface of the inner needle 4 (the minimum outside diameter part 4c) and the inner surface of the slit 81 can be reduced. Accordingly, operability upon performing a puncturing operation with the indwelling needle assembly 1 can be enhanced.

The seal member 8 permits the inner needle 4 to be inserted through the slit 81 in the assembled condition, and has a self-closing property, such that the slit 81 becomes closed by an elastic force (restoring force) of the seal member 8 when the inserted inner needle 4 is pulled out. This ensures that when the inner needle 4 is pulled out, leakage of liquid from the proximal end of the outer needle hub 3 can be prevented, while also maintaining sterility inside the outer needle hub 3.

Further, as shown in FIG. 2, in the assembled condition, the minimum outside diameter part 4c of the inner needle 4 is located inside the slit 81. This reduces the area of contact between the outer surface of the minimum outside diameter part 4c and the inner surface of the slit 81, thereby making it possible to reduce frictional resistance between these surfaces. In addition, it is possible to prevent the seal member 8 (the slit 81) from being prone to deformation, thus lowering the sealing properties thereof.

Examples of materials which can be used for the aforementioned seal member 8 include various elastic materials, including various rubber materials (particularly, those having been vulcanized), such as natural rubber, isoprene rubber, butyl rubber, butadiene rubber, styrene-butadiene rubber, urethane rubber, nitrile rubber, acrylic rubber, fluoro-rubbers, silicone rubbers, etc., various thermoplastic elastomers based on urethane, polyester, polyamide, olefin, styrene, or the like, and mixtures of these materials.

The compression member 30 is operable to accommodate the seal member 8, and to evenly compress an outer peripheral portion of the seal member 8 in the radial direction. As shown in FIG. 2 (as well as in FIGS. 4 to 9), the compression member 30 is composed of a body, which is in the shape of a bottomed tube (tubular body). The compression member 30 has a hole 301 provided in a bottom portion 303 thereof, and a flange (enlarged diameter part) 302 provided on the outer periphery of the bottom portion 303.

The hole 301 is provided substantially in the center of the bottom portion 303. The hole 301 is set to have an inside diameter, which is slightly larger than the outside diameter of the maximum outside diameter part 4a of the inner needle 4, so that the inner needle 4 (a part thereof ranging from the minimum outside diameter part 4c to the maximum outside diameter part 4a) can be inserted therein.

The flange 302 forms a part where the outside diameter of the bottom portion 303 is enlarged.

In addition, the inside diameter of the compression member 30 is set smaller than the outside diameter of the seal member 8. This ensures that when the seal member 8 is pressed (fitted) into the compression member 30 (hereinafter this condition will be referred to as a "pressed-in condition"), the seal member 8 becomes compressed in the radial direction. In the pressed-in condition, the compression member 30 and the seal member 8 are disposed at the inside 31 of the outer needle hub 3.

As shown in FIG. 2, the outer needle hub 3 is provided, at the inside 31 thereof, with a stepped part 311, the inside diameter of which is changed. A distal end face of the flange 302 of the compression member 30 abuts against the stepped part 311. In addition, the compression member 30 is fitted into the inside 31 of the outer needle hub 3. By disposing the compression member 30 in this manner, the compression member 30 is positioned relative to the outer needle hub 3.

The compression member 30 configured in the foregoing manner ensures that, in the assembled condition, inner surfaces of the slit 81 of the seal member 8 make firm and assured contact with the outer surface of the inner needle 4, and also that the inner surfaces of the slit 81 make firm contact with each other. As a result, essentially, the sealing function of the slit 81 (the seal member 8) is securely maintained. More specifically, the sealing function thereof is securely prevented from being lowered, so that leakage of liquid, such as blood or a medical liquid, through the slit 81 can be reliably prevented from occurring. In addition, sterility inside the outer needle hub 3 (at the inside 31 thereof) can also be maintained.

Further, in a condition where the inner needle 4 has been pulled out from the slit 81, the inner surfaces of the slit 81 of the seal member 8 make firm and reliable contact with each other. Consequently, the sealing function of the slit 81 is maintained securely, so that leakage of liquid through the slit 81 can be reliably prevented from occurring. In addition, sterility inside the outer needle hub 3 can be maintained, in the same manner as in the aforementioned assembled condition.

In addition, since the seal member 8 is cylindrical in shape as mentioned above, the compression member 30 can compress the seal member 8 evenly along the circumferential direction thereof. Therefore, for example in the assembled condition, generation of uneven contact between the inner surface of the slit 81 and the outer surface of the inner needle 4 can be prevented, so that the sealing function of the seal member 8 is securely maintained.

Further, it is preferable for the inside diameter of the compression member 30 (tubular body) to be smaller than the outside diameter of the seal member 8, by a factor of 1 to 30%, and more preferably, 9 to 15%. In other words, the compression ratio of the seal member 8 performed by the compression member 30 is preferably 1 to 30%, and more preferably, 9 to 15%.

If the inside diameter of the compression member 30 is less than the aforementioned lower limit, the seal member 8 may be compressed insufficiently, leading to unsatisfactory sealing performance. If the inside diameter of the compression member 30 exceeds the aforementioned upper limit, on the other hand, the seal member 8 may be compressed excessively, thus making it difficult to insert the inner needle 4 into the slit 81, or to pull the inner needle 4 out from the slit 81 once it has been inserted therein.

Examples of materials for the compression member 30 include various resin materials including polyolefins such as polyethylene, polypropylene, ethylene-vinyl acetate copolymer, etc., polyurethane, polyamides, polyesters, polycarbonate, acrylic resin, polybutadiene, polyvinyl chloride, etc., and various metallic materials such as stainless steel, aluminum, aluminum alloys, titanium, titanium alloys, etc.

In addition, the indwelling needle assembly 1 includes the protector 9, which covers at least the needle point 41 of the inner needle 4 when the inner needle 4 is pulled out from the outer needle 2. The protector 9, which is accommodated in the protector accommodating part 51 of the inner needle hub 5, is movable along the longitudinal direction of the inner needle 4. Features of the protector 9 will be described below.

The protector 9 is configured so as to be capable of being detachably linked to the outer needle hub 3. As shown in FIG. 3, the protector 9 has a protector body 91, and a shutter member (shutter means) 94 provided in the protector body 91.

The protector body 91 has a protector cover 92, and an internal member 93 inserted in the protector cover 92. The protector cover 92 and the internal member 93 are configured so that they can be moved relative to each other, and so that each of them can be placed in a movable state and an immovable state.

The protector cover 92 has a cover body part 921, which is tubular (cylindrical) in shape, and four projected parts 922 formed at a distal portion of the cover body part 921 and which project in the distal direction. The projected parts 922 are inserted, on their distal sides, into a proximal portion of the outer needle hub 3. Each of the projected parts 922 is provided at a distal portion thereof with a projection 923, which is inserted into a hole part 35 formed at a proximal portion of the outer needle hub 3, so as to become caught on an edge portion confronting the hole part 35.

As shown in FIG. 3, when the internal member 93 is inserted into the protector cover 92, and a distal portion of the internal member 93 is located at the portion (position) of the projections 923 of the projected parts 922 of the protector cover 92, movement (displacement) of the projections 923 in the direction of the center axis (axis) of the inner needle 4 is inhibited by means of the internal member 93. Further, latching between the projections 923 and the edge portions confronting the hole part 35 (i.e., a condition in which the projections 923 are caught on the edge portions that confront the hole part 35) is held (maintained). As a result, a linked state between the protector 9 and the outer needle hub 3 is maintained.

Starting from this condition, when the inner needle hub 5 is moved in the proximal direction, the inner needle 4 is moved attendantly therewith. In this case, the protector 9 is still kept in the linked state, so that movement thereof in the proximal direction does not occur. When the inner needle hub 5 is moved further in the proximal direction, the maximum outside diameter part 4a of the inner needle 4 becomes engaged with the internal member 93 of the protector 9, so that the internal member 93 can be moved in the proximal direction relative to the protector cover 92. When a distal portion of the internal member 93, having moved in this manner, reaches the proximal side of the projections 923 of the protector cover 92, the projections 923 are made movable along the direction of the center axis of the inner needle 4. When the protector cover 92 is moved in the proximal direction relative to the outer needle hub 3 under this condition, the projected parts 922 are deformed (deflected) toward the center axis of the inner needle 4, thus resulting in latching between the projections 923 and the edge portions confronting the hole part 35 being released, whereby the protector 9 becomes released from the outer needle hub 3. In this instance, for example, the protector cover 92 and the internal member 93 are kept in engagement with each other on a structural basis, whereby the internal member 93 is prevented from falling off (becoming released) from the protector cover 92.

The materials used for the protector cover 92 are not particularly limited. For example, the same materials as those mentioned above as materials for the outer needle hub 3 and the inner needle hub 5 can be used.

The internal member 93 is inserted into the protector cover 92 and is tubular (cylindrical) in shape. More specifically, the internal member 93 is provided in a central portion thereof with an inner needle passage 931, for insertion of the inner needle 4 therethrough, in a form so as to penetrate through the internal member 93 from the proximal end to the distal end of the internal member 93. The shutter member 94 is accommodated in a distal portion of the internal member 93, at an intermediate position of the inner needle passage 931. The shutter member 94 is configured such that, when the inner needle 4 is moved in the proximal direction and the maximum outside diameter part 4a of the inner needle 4 engages with the internal member 93 of the protector 9 as mentioned above, the needle point 41 is located on the proximal side relative to the shutter member 94, whereby the shutter member 94 inhibits the needle point 41 from passing through the inner needle passage 931 in the distal direction.

Materials used for the internal member 93 are not particularly limited. For example, the same materials as those mentioned above as materials for the outer needle hub 3 and the inner needle hub 5 can be used.

According to the protector 9 as described above, after use thereof, the needle point 41 of the inner needle 4 can be covered speedily and safely through a simple operation. In addition, owing to the operation of the shutter member 94, once covered, the needle point 41 is prevented from protruding from the distal end of the protector body 91 (the internal member 93) of the protector 9. Therefore, at the time of disposal of the inner needle 4 or the like, an accident in which a worker or another person might puncture his or her finger or the like with the needle point 41 by mistake is prevented from occurring. Thus, high safety is secured.

In addition, the indwelling needle assembly 1 may be provided with a fall-off preventative means for preventing the protector 9 from falling off from the needle point 41 after the needle point 41 has been covered by the protector 9 of the inner needle 4.

Further, as shown in FIG. 3 (as well as in FIGS. 1, 6, 7 and 9), a finger hook part (tab) 6, which is pushed by a finger in order to move the outer needle 2 in the distal direction relative to the inner needle 4, is formed (provided) in a projecting manner on the protector cover 92 of the protector 9. The protector cover 92 and the finger hook part 6 are formed integrally (or in a linked state). In addition, the finger hook part 6 projects in an upward direction through a cutout 515 formed in a distal portion of the protector accommodating part 51 of the inner hub 5. Herein, the expression "upward direction" implies a direction in which the skin (body surface) in the vicinity of a part of the patient (a person on whom the indwelling needle assembly 1 is used) faces, namely, the direction from the skin side toward the side of the indwelling needle assembly 1, which is to be punctured by the outer needle 2 (and the inner needle 4). In other words, the upward direction implies a direction toward which the cutting edge surface (not shown) of the needle point 41 of the inner needle 4 faces.

The finger hook part 6 is provided on the proximal side thereof with a finger rest surface 64, which permits a finger to be placed thereon. The finger hook part 6 is formed such that a force in an upward direction (vertically upward direction), namely, in a direction in which the finger hook part 6 projects (projecting direction) (upward direction in FIG. 3) relative to the center axis (axis) $O_1$ of the outer needle 2, can act on the finger hook part 6 when the outer needle 2 is moved in the distal direction relative to the inner needle 4.

This ensures that, when the outer needle 2 is moved in the distal direction relative to the inner needle 4 during a puncturing operation, the finger hook part 6 can be pressed in the distal direction while being lifted up (i.e., in a manner of lifting the finger hook part 6 upwards) in the projecting direction (upward direction in FIG. 3) by the finger. This enables the center axis $O_1$ of the outer needle 2 during distal movement thereof to be inhibited from becoming slanted with respect to the center axis $O_1$ of the outer needle 2, in a condition prior to the finger hook part 6 being pressed. Thus, the outer needle 2 can be moved straightly along the center axis $O_1$, namely, along the direction of the center axis $O_1$, without bending. Consequently, the outer needle 2 can be moved (advanced) smoothly, and excellent operability is ensured.

In the present embodiment, the finger hook part 6 is formed at a distal end portion of the cover body part 921 of the protector cover 92, and is in the form of a bent plate, as shown in FIG. 3. More specifically, the finger hook part 6 is composed of a slanted portion (slant plate) 61, which is disposed on the distal side relative to the cover body part 921 and is slanted toward the proximal side, a base portion 63 fixed to the distal portion of the cover body part 921, and a connecting portion (connecting plate) 62 which serves to connect the slant portion 61 and the base portion 63 to each other. A proximal-side surface of the slant portion 61 constitutes a finger rest surface 64. In the event that the finger hook part 6 is provided, with the finger inserted between the finger rest surface 64 (slant portion 61) and the connecting portion 62 and with the finger being caught on the finger rest surface 64, the finger hook part 6 can be pressed in the distal direction while being lifted up by the finger in the projecting direction thereof.

In addition, although the positional relationship between the finger hook part 6 and the center axis $O_1$ of the outer needle 2 is not particularly limited, it is preferable for the finger hook part 6 to be arranged on the center axis $O_1$ of the outer needle 2 in plan view, as shown in FIG. 1. This enables the outer needle 2 to be moved along the direction of the center axis $O_1$ more smoothly and assuredly.

Further, the finger rest surface 64 of the finger hook part 6 is formed with a rugged pattern (for example, a plurality of ribs arrayed side by side along the up-down direction on the finger contact surface 64), which serve as an anti-slip means for the finger. This makes it possible to prevent the finger from slipping off when the finger hook part 6 is pressed by the finger to move the outer needle 2 in the distal direction.

Next, an example of a method of using (operation of) the indwelling needle assembly 1 (in the case of puncturing a blood vessel) will be described in detail below.

[1] The indwelling needle assembly 1 is placed in an assembled condition (see FIGS. 1 and 3), and a connector, which is mounted to an end portion of an infusion line, is preliminarily connected to the connector 72, so that an infusion can be supplied through the infusion line.

Incidentally, in this instance, a predetermined part of the tube 7 or the infusion line is preliminarily pinched, for example, by a clamp (an example of a flow passage opening/closing means), thereby closing the lumen thereof.

[2] Next, closure of the tube 7 or the infusion line by the clamp or the like is released, whereupon the infusion is supplied through the infusion line and is introduced through the tube 7 into the outer needle hub 3.

The infusion having been introduced into the outer needle hub 3 fills up the flow passage 32 and a space at the inside 31 of the outer needle hub 3, which is located on the distal side relative to the seal member 8. In addition, the infusion is introduced into the lumen 21 of the outer needle 2, whereby priming of the lumen 21 with the infusion is performed. In this instance, a portion of the infusion flows out from the distal end opening 22 of the outer needle 2.

[3] After priming is completed in this manner, the tube 7 or the infusion line is once again preliminarily closed with the clamp or the like, and the wings 12a and 12b are closed by pinching them with the fingers. Then, with the wings 12a and 12b serving as a gripping part (operating part), the integrated outer needle 2 and inner needle 4 are made to puncture a blood vessel (vein or artery) of a patient.

When the operation for puncturing the blood vessel is conducted by gripping the wings 12a and 12b, the puncture angle is reduced. Stated otherwise, the outer needle 2 and the inner needle 4 are set more closely to a parallel condition relative to the blood vessel, as compared to a case in which the puncturing operation is conducted by gripping the outer needle hub 3 directly. Consequently, the puncturing operation is easy to carry out, and the burden on the patient's blood vessel is alleviated.

When the blood vessel is securely punctured by the outer needle 2, the internal pressure (blood pressure) within the blood vessel causes the blood to pass through the groove 44 of the inner needle 4 and flow back through the lumen 21 of the outer needle 2 in the proximal direction. This phenomenon can be confirmed at least in one part of the outer needle 2, the outer needle hub 3, the inner needle hub 5, and the tube 7, where the interior thereof is visible.

After such a phenomenon is confirmed, the outer needle 2 is advanced by a tiny distance in the distal direction along the inner needle 4, with the inner needle 4 serving as a guide.

This operation is carried out by pressing the finger hook part 6 in the distal direction with the index finger (pressing operation). This causes the outer needle 2, the outer needle hub 3 and the protector 9 to move in unison in the distal direction relative to the inner needle 4 and the inner needle hub 5.

In addition, when the outer needle 2 is advance in the distal direction, the finger hook part 6 preferably is pressed in the distal direction, while being lifted up (i.e., in a manner of lifting the finger hook part 6 upwards) in the projecting direction (upward direction in FIG. 3) by the index finger in order to move the outer needle 4 in the distal direction. This enables the center axis $O_1$ of the outer needle 2 to be inhibited from slanting in a reliable manner.

Further, when the blood vessel is punctured in this manner, the lumen 21 of the outer needle 2 already has been primed with the infusion. Therefore, erroneous penetration of bubbles into the blood vessel can be securely prevented from occurring. Thus, extremely high safety is attained.

In addition, once the tube 7 has been connected to a proximal portion of the outer needle hub 3 and the assembled condition is attained, the center axis $O_1$ of the outer needle 2 and the center axis $O_2$ at the distal portion of the tube 7 are substantially in parallel with each other.

Therefore, at a time of puncturing a blood vessel with the outer needle 2 and the inner needle 4, the tube 7 does not obstruct the puncturing operation. Thus, excellent operability is ensured.

[4] After the blood vessel has been securely punctured by the outer needle 2 (after the outer needle 2 is moved to a target position), the outer needle 2 or the outer needle hub 3 is fixed by one hand, while the inner needle hub 5 is gripped by the other hand and pulled in the proximal direction. This ensures that operations (movements) ranging from pulling of the inner needle 4 out from the outer needle 2 to the release of the protector 9 from the outer needle hub 3, are carried out sequentially and continuously. More specifically, first, the inner needle 4 is moved in the proximal direction, and then, the inner needle 4 is pulled out from the outer needle 2.

[5] When the inner needle 4 is moved further in the proximal direction, and the needle point 41 passes through the slit 81, the seal member 8, which has a self-closing property, closes the slit 81 by an elastic force thereof. Accordingly, leakage of liquid through the slit 81 is obviated, and sterility inside the outer needle hub 3 and the infusion line is secured.

[6] When the inner needle 4 is moved further in the proximal direction in order to cause the needle point 41 to reach the proximal side of the shutter member 94, under the operation of the shutter member 94 as mentioned above, it becomes impossible to move the needle point 41 of the inner needle 4 so as to return in the distal direction. More specifically, the shutter member 94 abuts against the needle point 41, so that the needle point 41 cannot be returned in the distal direction.

[7] When the inner needle 4 is moved further in the proximal direction and the inner needle 4 engages with the internal member 93 of the protector 9, the internal member 93 becomes movable in the proximal direction relative to the protector cover 92. Then, when the internal member 93 is moved in the proximal direction relative to the protector cover 92 whereupon a distal portion of the internal member 93 reaches the proximal side of the projections 923 of the protector cover 92, the projections 923 are made movable in the direction of the center axis of the inner needle 4, as mentioned above. As a result, latching between the projections 923 and the edge portions that confront the hole part 35 is released. Thereafter, the internal member 93 and the protector cover 92 may be moved in a unitary manner in the proximal direction, whereby the protector 9 becomes separated (released) from the outer needle hub 3.

[8] Subsequently, the tube 7, which is inserted in the tube accommodating part 52 of the inner needle hub 5, is detached through the groove 521.

After the inner needle 4 has been pulled out from the outer needle 2, the inner needle 4 and the inner needle hub 5 become useless and should be discarded.

The inner needle 4 has the needle point 41 thereof covered by the protector 9, so that the needle point 41 is prevented from being moved toward the distal side beyond the shutter member 94 and protruding from the distal end of the protector 9. Therefore, an accident, in which a person in charge of disposal or another person might puncture his or her finger or the like with the needle point 41 by mistake, can be prevented from occurring.

[9] Next, the wings 12a and 12b are opened, and are affixed to the skin with a pressure sensitive adhesive tape or the like. In addition, closure of the tube 7 or the infusion line with the clamp, as mentioned above, is released, whereupon supply of an infusion is started.

The infusion supplied through the infusion line flows through the respective lumens of the connector 72, the tube 7, the outer needle hub 3 and the outer needle 2, so as to be injected into the patient's blood vessel.

Next, a method of producing the indwelling needle assembly 1 will be described below with reference to FIGS. 4 through 9.

The method of producing the indwelling needle assembly 1 includes an insertion step (first step), an inner needle hub fixation step (second step), a lubricant application step (third step), a reciprocation step (fourth step), a tube connection step (fifth step), and an outer needle hub fixation step (sixth step), which are carried out sequentially.

<1> Insertion Step

First, the seal member 8, the compression member 30 and the inner needle 4 are prepared.

The seal member 8 is formed preliminarily with the slit 81. This makes it possible to easily carry out insertion of the inner needle 4 (insertion operation), which will be described later. The seal member 8 is pressed into (accommodated in) the compression member 30, in order to obtain a pressed-in condition (see FIG. 4). Incidentally, the proximal portion 45 of the inner needle 4 may have a tapered shape, wherein the outside diameter thereof gradually decreases in the proximal direction.

The inner needle 4 is inserted through (into) the slit 81 of the seal member 8 in the pressed-in condition, starting with the side thereof that is opposite to the needle point 41, or in other words, starting with the proximal portion 45.

When the inner needle 4 is pushed in further toward the proximal side, the proximal portion 45 moves beyond the seal member 8 and passes through the hole 301 in the compression member 30, so as to protrude from the hole 301.

Figure 5:
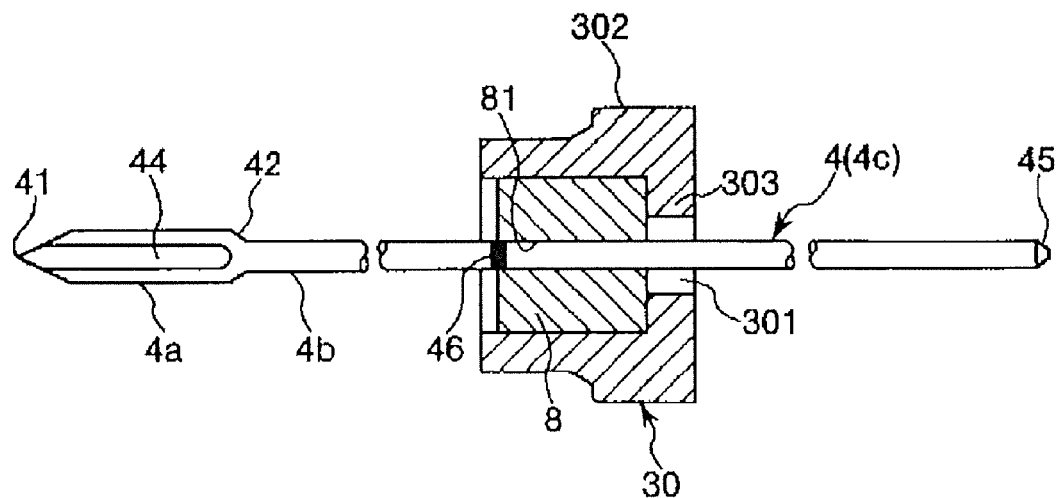
FIG. 5 is a drawing (longitudinal sectional view) for sequentially illustrating the steps (first embodiment) for producing the indwelling needle assembly shown in FIG. 1.
Figure 6:
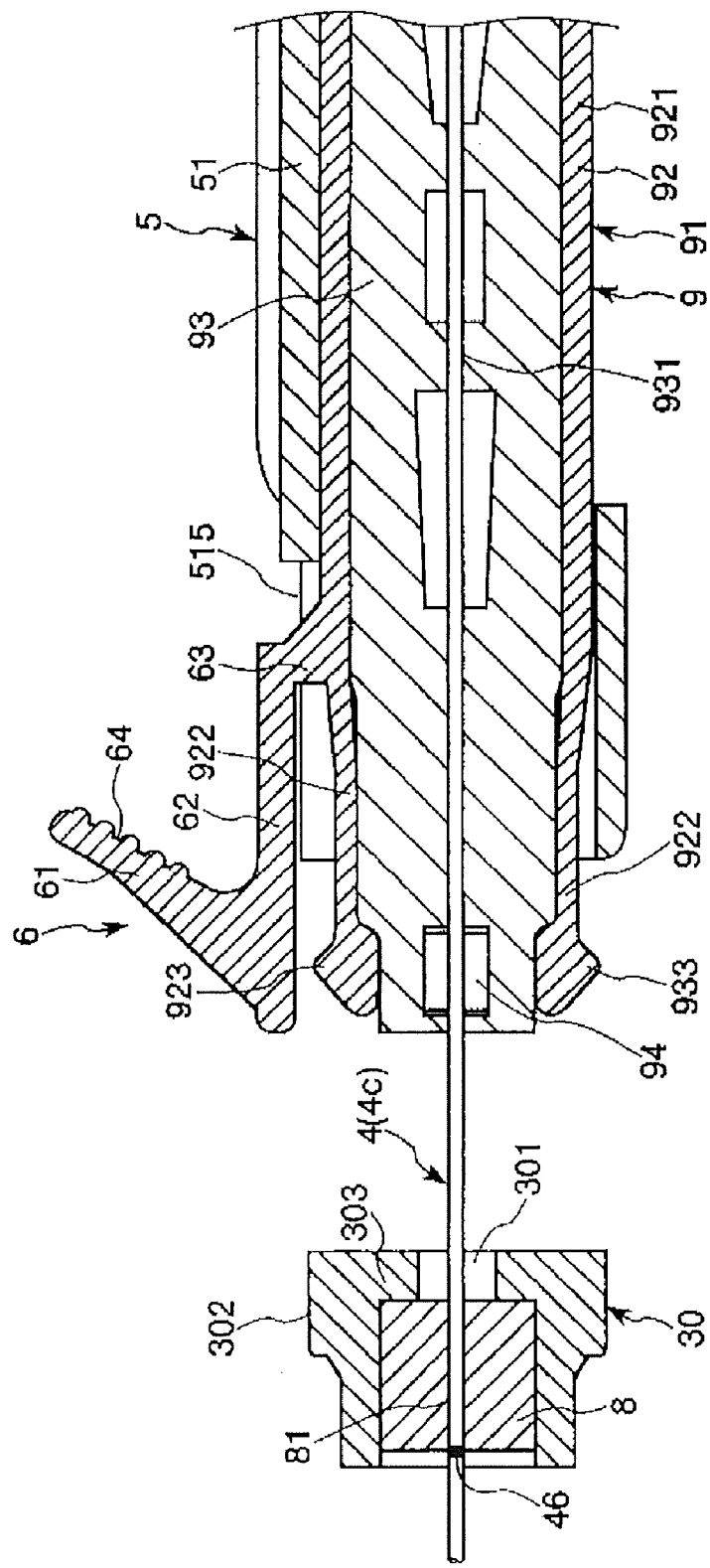
FIG. 6 is a drawing (longitudinal sectional view) for sequentially illustrating the steps (first embodiment) for producing the indwelling needle assembly shown in FIG. 1.

Further, in this instance, a predetermined position on the minimum outside diameter part 4c of the inner needle 4 is disposed within the slit 81, thereby positioning the inner needle 4 relative to the seal member 8. Incidentally, as shown in FIG. 5, the minimum outside diameter part 4c of the inner needle 4 may be provided with a marker 46 thereon for facilitating positioning. The marker 46 can be provided, for example, at a portion of the inner needle 4 that corresponds to the distal end face (the end face on one side) of the seal member 8.

The condition of the seal member 8, the compression member 30 and the inner needle 4, which are assembled in this manner, shall be referred to as an "inserted condition" (see FIG. 5).

In the insertion step, the needle point 41 of the inner needle 4 is prevented securely from experiencing wear, due to contact thereof with the seal member 8 (the slit 81). This ensures that damage to the needle point 41 (for example, chipping of the cutting edge) can be securely prevented from occurring, or in other words, that the needle point 41 can be protected assuredly.

In addition, when the inner needle 4 is inserted into and through the seal member 8, the insertion operation can be carried out while the inner needle 4 is rotated about its axis. This enables the insertion operation to be performed more easily.

Further, as mentioned above, when the inner needle 4 is inserted into and through the seal member 8, the operation (insertion operation) is carried out while the seal member 8 is set in a pressed-in condition. This ensures that the inner needle 4 is compressed toward the center of the seal member 8, so that the inner needle 4 can be inserted substantially through the center of the slit 81.

<2> Internal Needle Hub Fixation Step

Next, the inner needle hub 5, which is assembled (accommodated) in the protector 9, is prepared.

The inner needle 4 in the inserted condition (the condition shown in FIG. 5) is inserted into the inner needle hub 5 (the protector 9), starting with the proximal portion 45 thereof. As a result, the proximal portion 45 of the inner needle 4 passes through the inner needle passage 931 in the protector 9, until reaching the projected part 512 of the inner needle hub 5. The proximal portion 45 of the inner needle 4 is inserted into the hole 513, and is fixed in the projected part 512 by way of, for example, adhesion, fusing (heat fusing, microwave fusing, ultrasonic fusing) or the like. As a result, the inner needle hub 5 and the inner needle 4 are assembled together, and the inner needle 4 is affixed to the inner needle hub 5 (see FIG. 6).

<3> Lubricant Application Step

Figure 7:
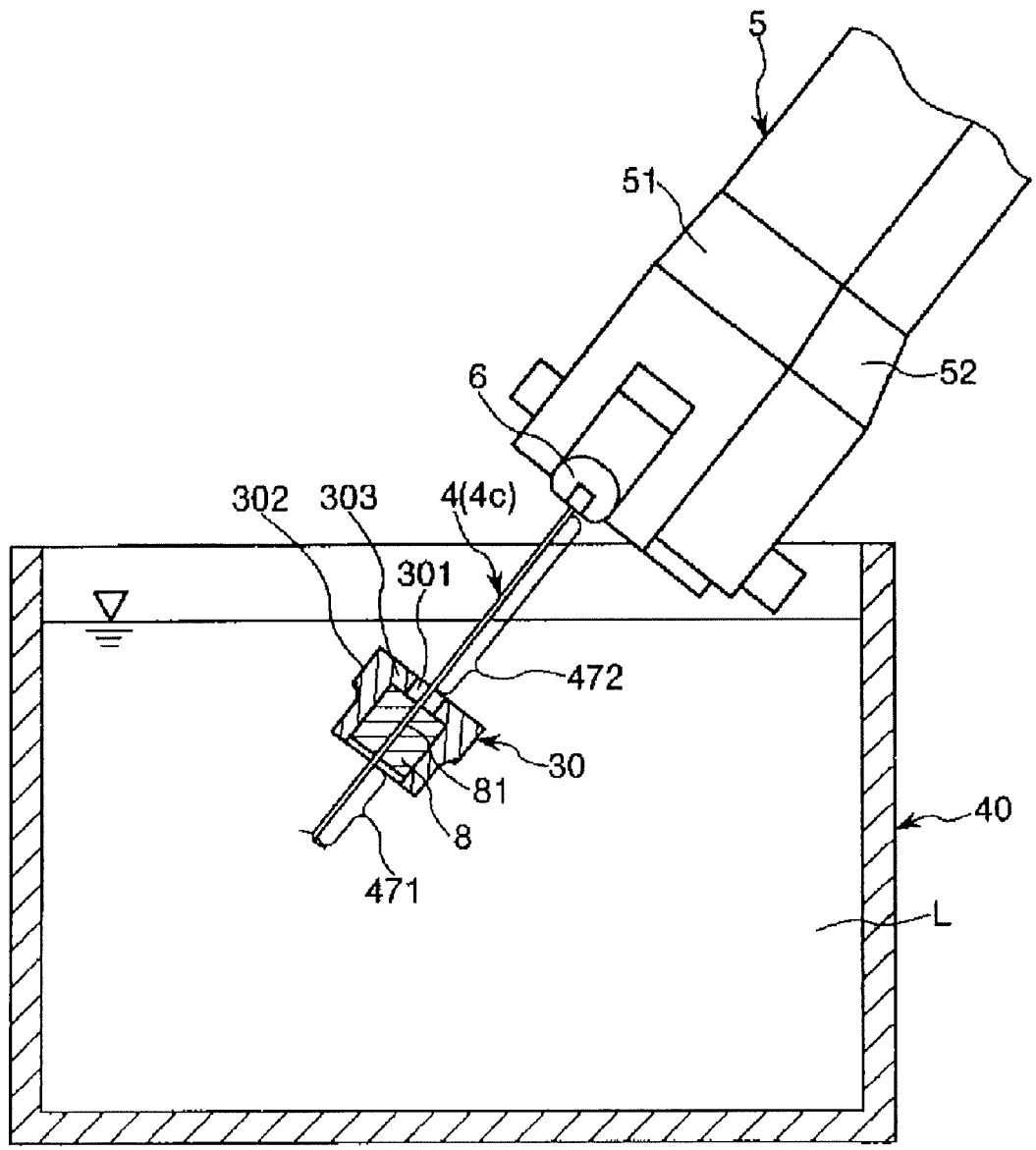
FIG. 7 is a drawing (longitudinal sectional view) for sequentially illustrating the steps (first embodiment) for producing the indwelling needle assembly shown in FIG. 1.

Subsequently, a reservoir 40, which is filled with a liquid lubricant (lubricating liquid) L, is prepared. Then, as shown in FIG. 7, the inner needle 4, the seal member 8 and the compression member 30 in the inserted condition are immersed in the reservoir 40. This enables the lubricant L to be easily and assuredly applied (supplied) to the outer peripheral surface of a portion of the inner needle 4 that protrudes from the seal member 8. Incidentally, the portion of the inner needle 4 that protrudes from the seal member 8 includes a distal-side part (distal-side protruding part 471) and a proximal-side part (proximal-side protruding part 472), with the seal member 8 being arranged therebetween (see FIG. 7). In addition, the proximal-side protruding part 472 does not have to be immersed entirely, and it suffices if only the portion thereof near the seal member 8 is immersed.

Further, when the inner needle 4 is immersed in the reservoir 40, the inner needle hub 5, which is not immersed in the reservoir 40, is gripped, so that immersion of the inner needle 4 can be carried out easily. Thus, the inner needle hub 5 functions as a gripping part, which is gripped by the worker when the inner needle 4 is immersed in the reservoir 40.

In addition, the reservoir 40 is of a size such that, when the inner needle 4 (inclusive of the seal member 8 and the compression member 30) is immersed therein, the immersed portion of the inner needle 4 can be securely accommodated.

Further, the lubricant L supplied to the reservoir 40 is provided in a sufficient amount, so that the lubricant L can be applied sufficiently both to the distal-side protruding part 471 and to the proximal-side protruding part 472.

In addition, the lubricant L is not particularly limited. Examples of lubricants which can be used for the lubricant L include lubricants composed mainly of silicone, especially, silicone oils, reactive silicones, and mixtures thereof. Reactive silicones imply silicones that can be cured by heat, radiation, or the like. When reactive silicone is used, the silicone remains on the inner surfaces of the slit 81 in the seal member 8, as well as on the surface of the inner needle 4, for a long time. Therefore, the effect of the silicone on reducing friction between the inner needle 4 and the seal member 8 is maintained. Further, although the mixing ratio used when mixing silicone oil with reactive silicone ("amount of silicone oil": "amount of reactive silicone") is not particularly limited, the mixing ratio preferably is in a range from, for example, 1:9 to 9:1, and more preferably, from 5:5 to 8:2.

<4> Reciprocation Step

Next, the inner needle 4, the seal member 8 and the compression member 30 in the inserted condition are drawn up (taken out) from the reservoir 40. As a result, the reciprocating operation, which shall be described later, can be performed easily.

Figure 8:
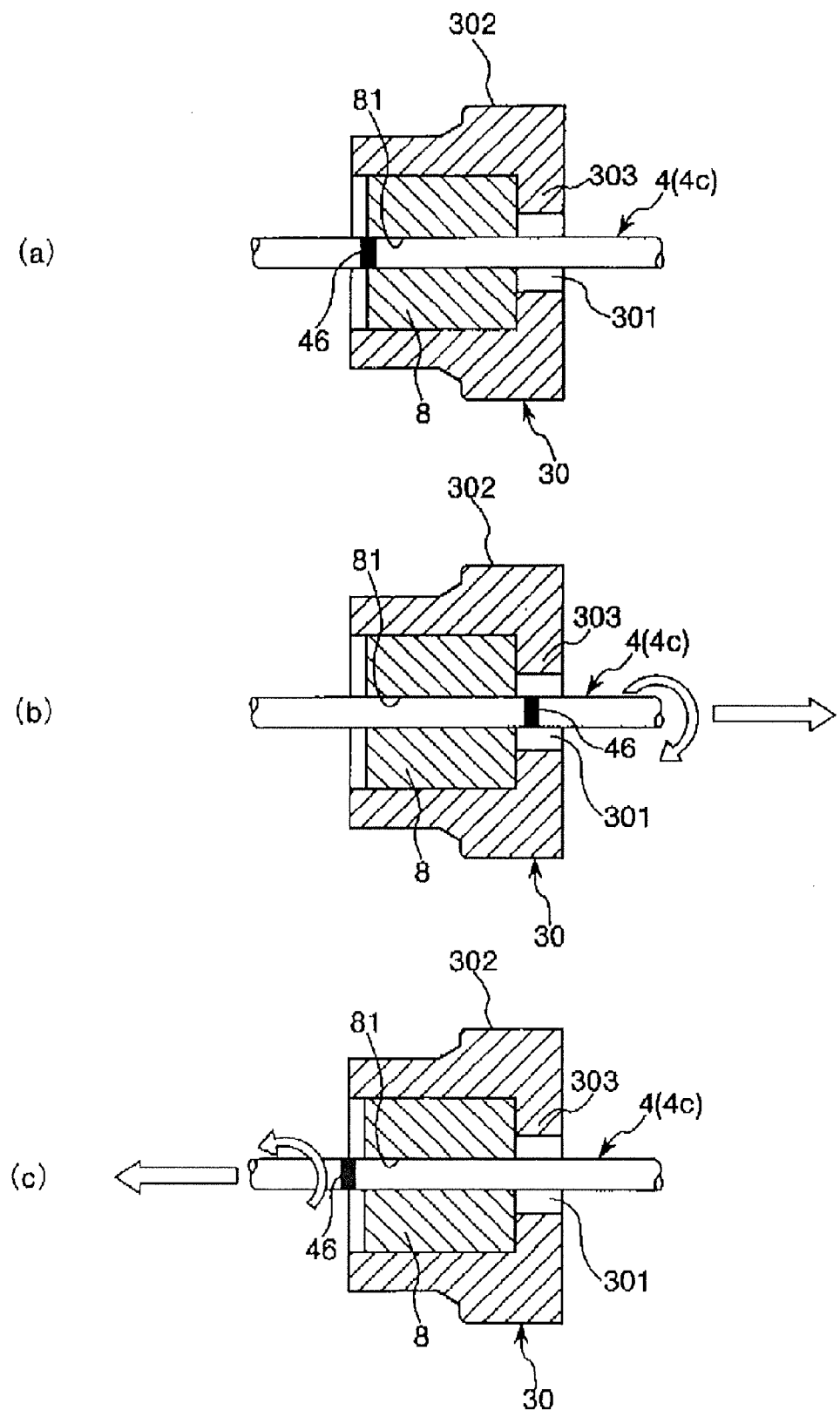
FIG. 8 shows drawings (longitudinal sectional views) for sequentially illustrating the steps (first embodiment) for producing the indwelling needle assembly shown in FIG. 1.

Then, while the inner needle hub 5 is gripped by one hand, and with the compression member 30 being gripped by the other hand, the inner needle hub 5 is reciprocated in the axial direction of the inner needle 4 relative to the compression member 30 (the seal member 8), as shown in FIG. 8. Attendant therewith, the inner needle 4 also is reciprocated along the axial direction thereof. As a result, the lubricant L, which is applied to outer peripheral surfaces of the distal-side protruding part 471 and to the proximal-side protruding part 472 of the inner needle 4, enters (penetrates) into the slit 81. By entry of the lubricant L into the slit 81, frictional resistance between the inner needle 4 and the seal member 8 (the slit 81) can reliably be reduced when the inner needle 4 is pulled out from the seal member 8, as mentioned above.

In addition, during the reciprocating operation, a marker 46 (see FIG. 8(a)) of the inner needle 4, which is located near the distal end face of the seal member 8, travels a distance so as to reach beyond the proximal end face (end face on the other side) of the seal member (see FIG. 8(b)). This ensures that the lubricant L can assuredly be supplied into the slit 81 over the entire range of the slit 81 along the longitudinal direction thereof, whereby frictional resistance can be reduced more assuredly. Further, by visually checking the marker 46, the distance traveled by the marker 46 can be ascertained.

In addition, the reciprocating operation preferably is conducted while the inner needle 4 is rotated about its own axis. This ensures that sliding resistance between the inner needle 4 and the seal member 8 is reduced during the reciprocating operation, whereby the reciprocating operation can be facilitated.

Further, the number of times that the reciprocating operation is carried out is not particularly limited. For example, the number of times preferably is at least one, and more preferably, 1 to 5 times.

<5> Tube Connection Step

On the other hand, the tube 7 with the connector 72 connected thereto and the outer needle hub 3 are prepared.

Incidentally, the outer needle hub 3 is accompanied by the outer needle 2 already being affixed thereto.

Figure 9:
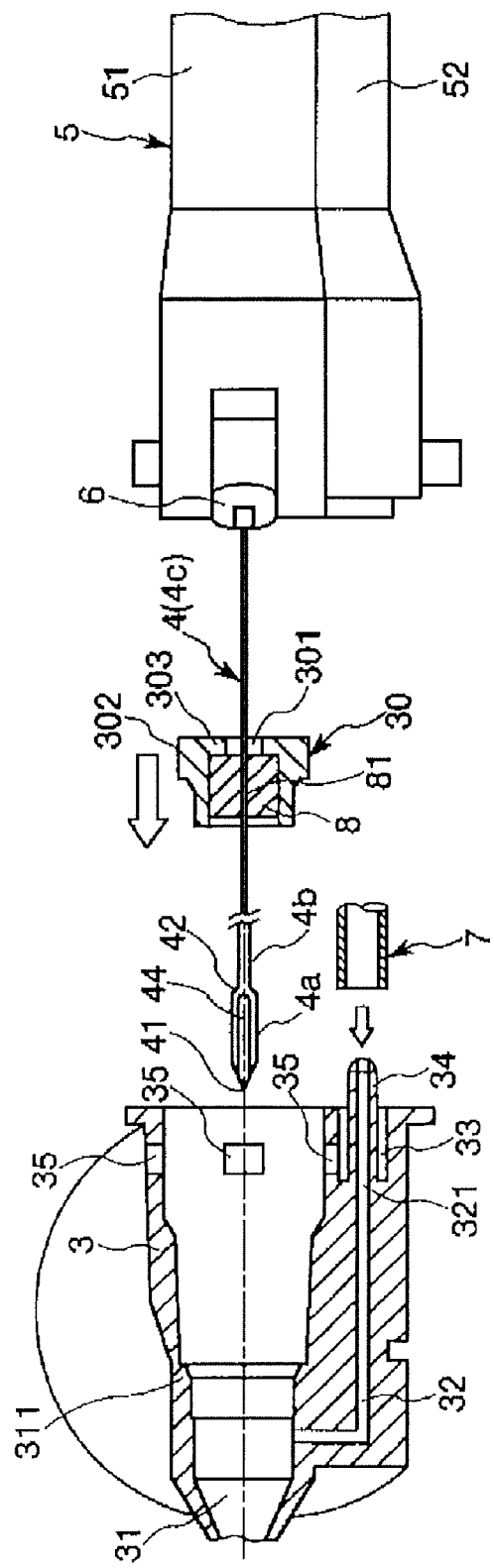
FIG. 9 is a drawing (longitudinal sectional view) for sequentially illustrating the steps (first embodiment) for producing the indwelling needle assembly shown in FIG. 1.

An end portion of the tube 7, on the side opposite to the connector 72, is inserted into the recess 33 of the outer needle hub 3 and is fitted onto the projected part 34 (see FIG. 9). This results in the tube 7 and the outer needle hub 3 becoming connected to each other.

<6> Outer Needle Hub Fixation Step

Subsequently, while maintaining the positional relationship between the inner needle 4 and the seal member 8, as shown in FIG. 9, the inner needle 4 in the inserted condition is inserted into the outer needle hub 3 from the proximal side thereof until the inner needle hub 5 abuts against the outer needle hub 3. As a result, the inner needle 4 is accommodated within the outer needle 2, the compression member 30 is fitted into the inside 31 of the outer needle hub 3, and the seal member 8 is affixed to the outer needle hub 3 through the compression member 30.

Thereafter, the tube 7, which is connected to the outer needle hub 3, is accommodated in the tube accommodating part 52 of the inner needle hub 5.

By means of the aforementioned steps, the indwelling needle assembly 1 is produced (assembled) assuredly.

Further, in the indwelling needle assembly 1 in the assembled condition, the lubricant L is deposited into the slit 81 and on the outer surface of the inner needle 4, thereby making it possible to reduce frictional resistance between the inner needle 4 and the seal member 8 reliably, at a time when the inner needle 4 is pulled from the seal member 8 in a condition where a blood vessel has been securely punctured by the outer needle 2. As a result, the outer needle 2 can be moved smoothly, and the indwelling needle assembly 1 is excellent in operability during the puncturing operation.

In addition, when the inner needle 4 is formed from a metallic material, as mentioned above, due to the presence of the lubricant L, slidability of the inner needle 4 relative to the seal member 8 is enhanced, or stated otherwise, frictional resistance between the seal member 8 and the inner needle 4 can be reduced more reliably. Consequently, excellent operability during the pulling-out operation can be ensured.

Further, since the lubricant application step takes place after the insertion step, fixation of the inner needle 4 to the inner needle hub 5 can be more easily carried out by the aforementioned fixing method.

In addition, while the seal member 8, which is preliminarily formed with the slit 81 therein, has been used in the insertion step, the invention is not limited by this feature. For example, a seal member 8, which is not formed with a slit 81 therein, may also be used. In this case, by inserting the inner needle 4 into and through the seal member 8 (i.e., by causing the inner needle 4 to penetrate through the seal member 8), a slit (through-hole) is formed therein.

Further, while the proximal portion 45 of the inner needle 4 has a tapered shape, in which the outside diameter decreases gradually along the proximal direction, the invention is not limited by this feature. For example, the proximal portion 45 may also have a rounded shape.

In addition, during the insertion step, the inner needle 4 is inserted into and through the seal member 8 in the pressed-in condition, namely, in the condition where the seal member 8 has been pressed into the compression member 30. However, the present invention is not limited to this procedure. More specifically, the inner needle 4 may be inserted into and through the seal member 8 as is, that is, in a condition where the seal member 8 has not been pressed into the compression member 30. In this case, pressing of the seal member 8 into the compression member 30 can be performed after the lubricant application step, for example.

Further, the lubricant application step is not limited to a method in which application of the lubricant L is conducted by immersion in the lubricant L. For example, a method of applying the lubricant L by spraying, or by use of a dropping pipette or the like, may also be used.

In addition, in the reciprocation step, reciprocation may be conducted while the inner needle 4 is swung to and fro.

<Second Embodiment>

FIGS. 10 to 17 are drawings (longitudinal sectional views) sequentially illustrating steps (second embodiment) for producing the indwelling needle assembly shown in FIG. 1. Incidentally, in the following description, the right side in FIGS. 10 to 12 and 14 to 17 (and in FIGS. 18 to 20 as well) shall be referred to as "proximal," and the left side as "distal."

Next, a second embodiment of the method of producing an indwelling needle assembly, as well as the indwelling needle assembly produced thereby, according to the present invention will be described below with reference to the drawings. The following description will be centered on differences from the above-described embodiment, while descriptions of the same items already discussed above will be omitted.

The present embodiment is the same as the aforementioned first embodiment, except for differences in the steps used for producing the indwelling needle assembly.

The method of producing the indwelling needle assembly 1 according to the present embodiment will be described with reference to FIGS. 10 through 17.

The method of producing the indwelling needle assembly 1 includes an inner needle hub fixation step, a jig insertion step, a lubricant application step, an inner needle insertion step, a reciprocation step, a jig pulling-out step, a tube connection step, and an outer needle hub fixation step.

When carrying out the steps used for producing the indwelling needle assembly 1, in particular, the jig insertion step, the inner needle insertion step and the reciprocation step, a jig 50 is used. The jig 50 is comprised of a tubular body, which is annular in cross-sectional shape, and which permits an inner needle 4 to be inserted through the inside thereof (the inside of a lumen 501) (see FIGS. 15 and 16). In addition, an inner peripheral part of the jig 50 functions as a guide part for guiding the inner needle 4 at the time when the inner needle 4 is inserted into and through the lumen 501. Therefore, the jig 50 serves as "a guide tube" for guiding the inner needle 4 as it is being moved.

The jig 50 is provided at a distal portion thereof with a distal-side tapered part 502, where the outside diameter decreases gradually along the distal direction, and further is provided at the proximal portion with a proximal-side tapered part 503, where the diameter decreases gradually along the proximal direction. The distal-side tapered part 502 and the proximal-side tapered part 503 ensure that when the jig 50 is inserted into a seal member 8 (jig insertion step), as will be described later, the insertion operation can easily be carried out, starting with either the distal side or the proximal side of the jig 50.

In addition, preferably, the inside diameter of the jig 50 is not less than 105%, based on the maximum outside diameter part 4*a* of the inner needle 4, and not more than the maximum opening diameter of a slit 81. Further, the length of the jig 50 preferably is greater than the length (entire length) of the seal member 8.

In addition, the material for the jig 50 is not particularly limited. Examples of materials which can be used include metallic materials, such as stainless steel, aluminum or aluminum alloys, titanium or titanium alloys, etc. When the jig 50 is formed from such a metallic material, the jig 50 can have appropriate rigidity, so that insertion of the jig 50 through (into) the seal member 8 in the jig insertion step can be carried out easily and assuredly. Also, the jig 50 may be formed using a plastic material instead of a metallic material.

Next, steps for producing the indwelling needle assembly 1 will be described below.

<<A1>> Inner Needle Hub Fixation Step

First, the inner needle 4 and an inner needle hub 5 with a protector 9 assembled (accommodated) therein are prepared.

Figure 10:
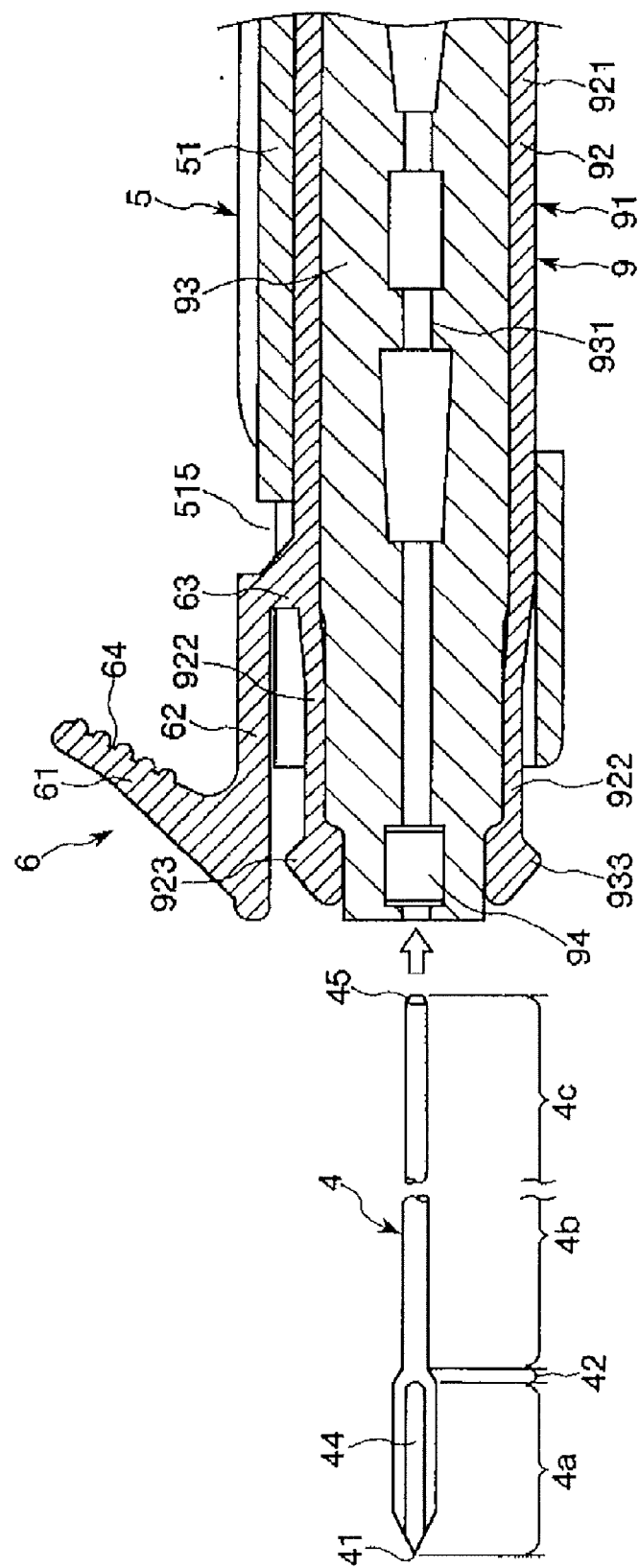
FIG. 10 is a drawing (longitudinal sectional view) for sequentially illustrating steps (second embodiment) for producing the indwelling needle assembly shown in FIG. 1.

As shown in FIG. 10, the inner needle 4 is inserted into and through the inner needle hub 5 (protector 9), starting with a proximal side thereof. As a result, a proximal portion 45 of the inner needle 4 passes through an inner needle passage 931 in the protector 9, to arrive at (reach) a projected part 512 of the inner needle hub 5. The proximal portion 45 of the inner needle 4 is inserted in a hole 513, whereupon the proximal portion 45 is fixed to the projected part 512, for example, by fitting. As a result, the inner needle hub 5 and the inner needle 4 are assembled together, and the inner needle 4 is affixed to the inner needle hub 5 (see FIG. 3).

Incidentally, the proximal portion 45 of the inner needle 4 may have a tapered shape, wherein the outside diameter thereof decreases gradually along the proximal direction (see FIG. 10).

<<A2>> Jig Insertion Step

Next, the seal member 8, a compression member 30, and the jig 50 are prepared.

The seal member 8 preliminarily is formed with the slit 81. This enables the operation of inserting the jig 50 (insertion operation) to be carried out easily. The seal member 8, in which the jig 50 has not yet been inserted, is pressed (accommodated) in the compression member 30 in order to obtain a pressed-in condition (see FIG. 11).

Figure 11:
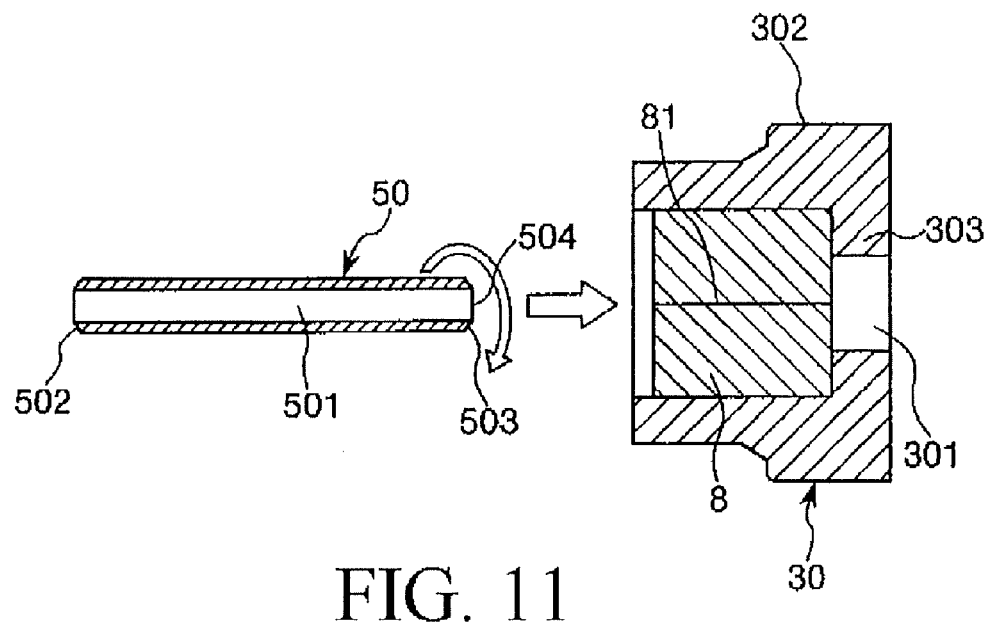
FIG. 11 is a drawing (longitudinal sectional view) for sequentially illustrating the steps (second embodiment) for producing the indwelling needle assembly shown in FIG. 1.

As shown in FIG. 11, the jig 50 is inserted through (into) the slit 81 of the seal member 8 in the pressed-in condition, starting with the proximal-side tapered part 503 thereof. The insertion operation can be carried out more easily, owing to the synergistic effect of the proximal-side tapered part 503, which is formed preliminarily at the proximal portion of the jig 50, and the slit 81, which is preliminarily formed in the seal member 8.

Figure 12:
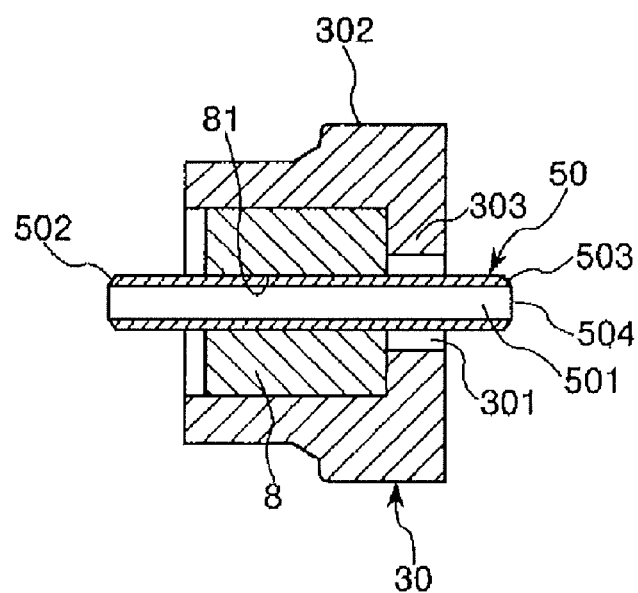
FIG. 12 is a drawing (longitudinal sectional view) for sequentially illustrating the steps (second embodiment) for producing the indwelling needle assembly shown in FIG. 1.

When the jig 50 is pressed in further toward the proximal side, as shown in FIG. 12, the proximal-side tapered part 503 reaches beyond the seal member 8 and passes through a hole 301 in the compression member 30, so as to protrude from the hole 301. Incidentally, it is preferable that the respective amounts of protrusion (protrusion lengths) of the jig 50, as measured from both end faces of the compression member 30, are approximately equal to each other.

The condition of the seal member 8, the compression member 30 and the jig 50, which are assembled together in this manner (i.e., the condition shown in FIG. 12), will be referred to as a "jig-inserted condition."

In addition, when the jig 50 is inserted into and through the seal member 8, the insertion operation can be performed while the jig 50 is rotated about its axis. This enables the insertion operation to be carried out more easily.

Further, when the inner needle 4 is inserted into and through the seal member 8, as mentioned above, the operation (insertion operation) is conducted with the seal member 8 set in a pressed-in condition. With the seal member 8 being compressed in this manner, pressure on the seal member 8 is directed toward the center axis of the seal member 8, so that the inner needle 4 can be located in the center of the seal member 8.

Incidentally, the seal member 8 may be compressed after insertion of the inner needle 4 into and through the seal member 8.

<<A3>> Lubricant Application Step

Figure 13:
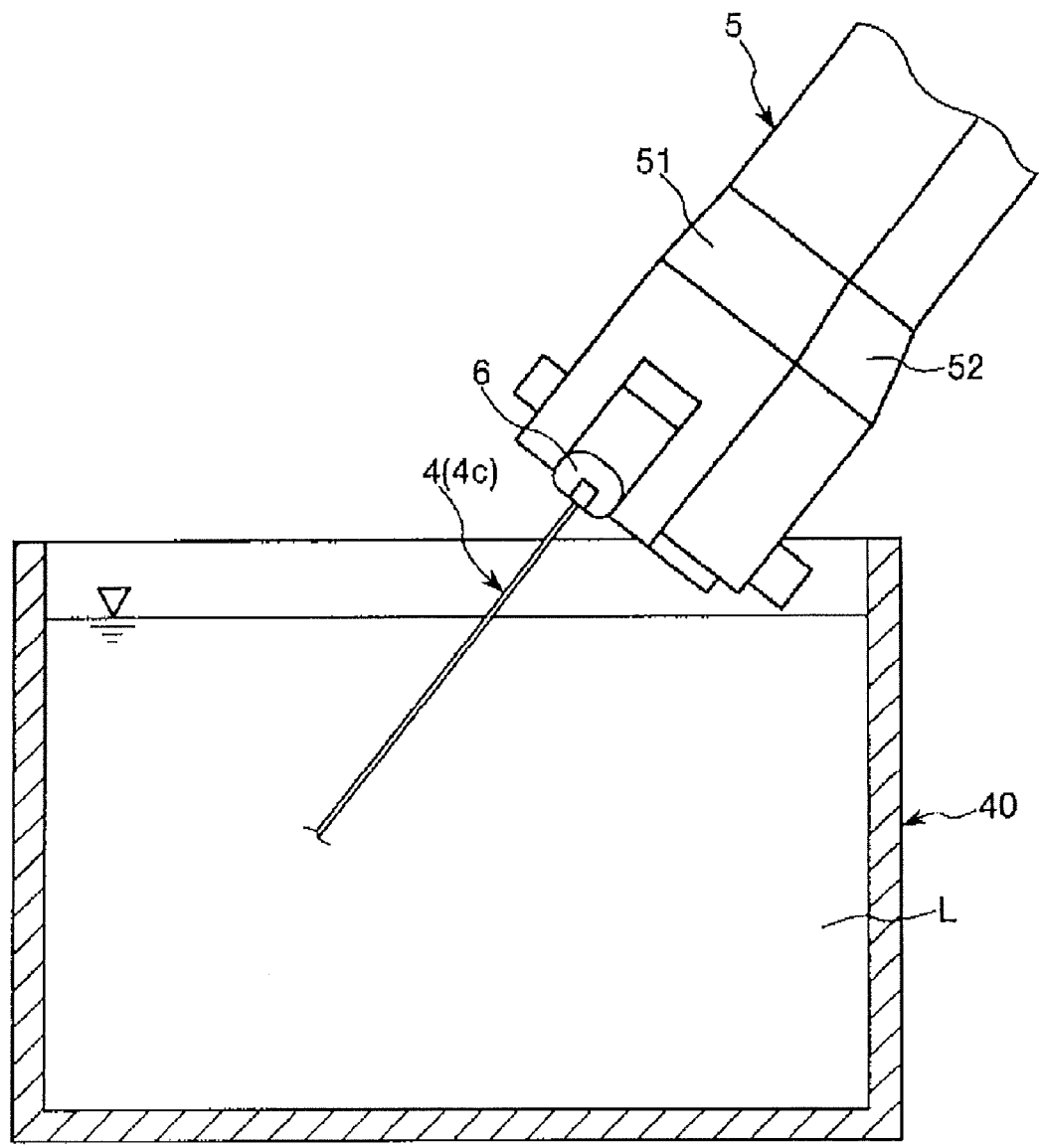
FIG. 13 is a drawing (longitudinal sectional view) for sequentially illustrating the steps (second embodiment) for producing the indwelling needle assembly shown in FIG. 1.

On the other hand, a reservoir 40, which is filled with a liquid lubricant (lubricating liquid) L, is prepared. Then, as shown in FIG. 13, the inner needle 4, which is affixed to the inner needle hub 5, is immersed in the reservoir 40. By such an immersion method, the lubricant L can be applied (supplied) easily and assuredly over the outer peripheral surface of the inner needle 4, and in particular, to the outer peripheral surface of a minimum outside diameter part 4c, which corresponds to the seal member 8 in the assembled condition.

In addition, when the inner needle 4 is immersed in the reservoir 40, the immersing operation can be easily carried out by gripping the inner needle hub 5, which is not immersed in the reservoir 40. Thus, the inner needle hub 5 functions as a grip part that may be gripped by the worker at the time of immersing the inner needle 4 in the reservoir 40.

Further, the reservoir 40 has a size such that when the inner needle 4 (inclusive of the seal member 8 and the compression member 30) is immersed, a portion of the inner needle 4 that is to be immersed can be fully accommodated therein.

In addition, the lubricant L is not particularly limited. Examples of usable lubricants include lubricants comprised mainly of silicone, particularly, silicone oils, reactive silicones, and mixtures thereof. Reactive silicones are silicones that can be cured by heat or radiation. When a reactive silicone is used, the silicone remains on the inner surfaces of the slit 81 in the seal member 8 and on the surface of the inner needle 4 for a prolonged period of time, so that the effect thereof on reducing friction between the inner needle 4 and the seal member 8 is maintained. In addition, although the mixing ratio used when mixing the silicone oil with reactive silicone ("amount of silicone oil": "amount of reactive silicone") is not particularly limited, the mixing ratio preferably lies within a range from, for example, 1:9 to 9:1, and more preferably, from 2:8 to 9:1.

<<A4>> Inner Needle Insertion Step

Next, the jig 50 (inclusive of the seal member 8 and the compression member 30) in the jig-inserted condition, which is produced (assembled) in the aforementioned jig insertion step, and the inner needle 4 with the lubricant L applied thereto, which is produced in the aforementioned lubricant application step, are prepared.

Figure 14:
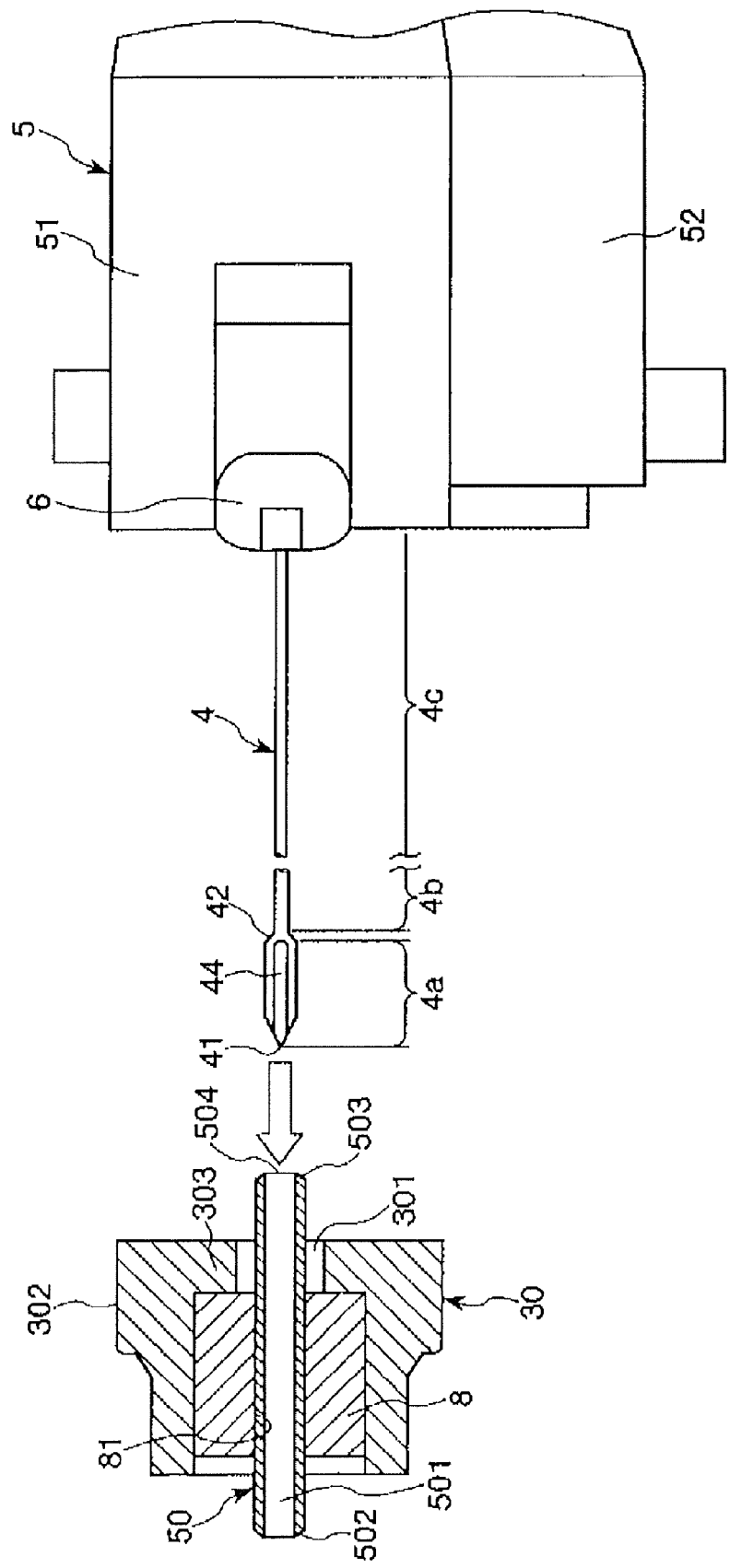
FIG. 14 is a drawing (longitudinal sectional view) for sequentially illustrating the steps (second embodiment) for producing the indwelling needle assembly shown in FIG. 1.
Figure 15:
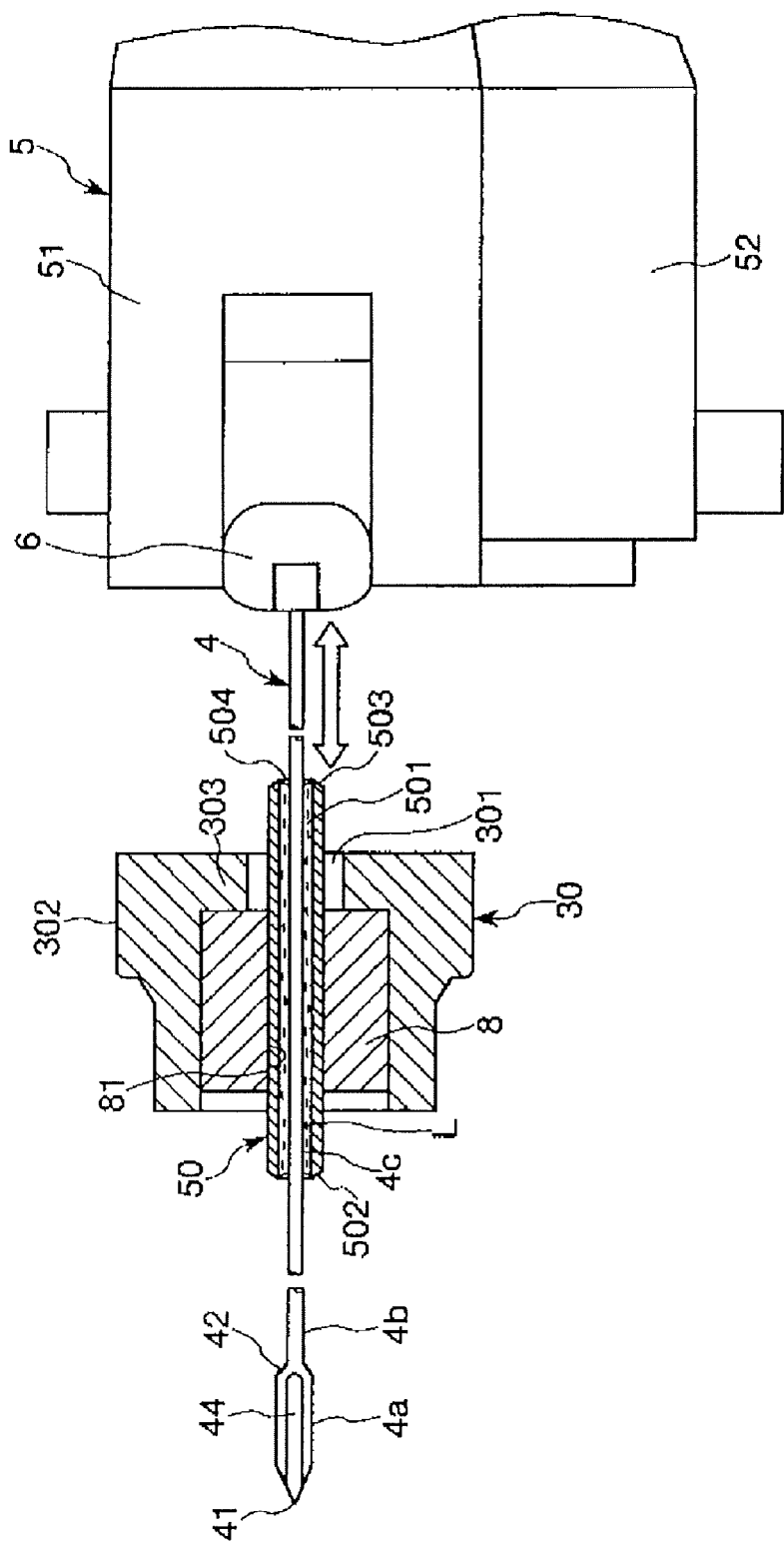
FIG. 15 is a drawing (longitudinal sectional view) for sequentially illustrating the steps (second embodiment) for producing the indwelling needle assembly shown in FIG. 1.
Figure 16:
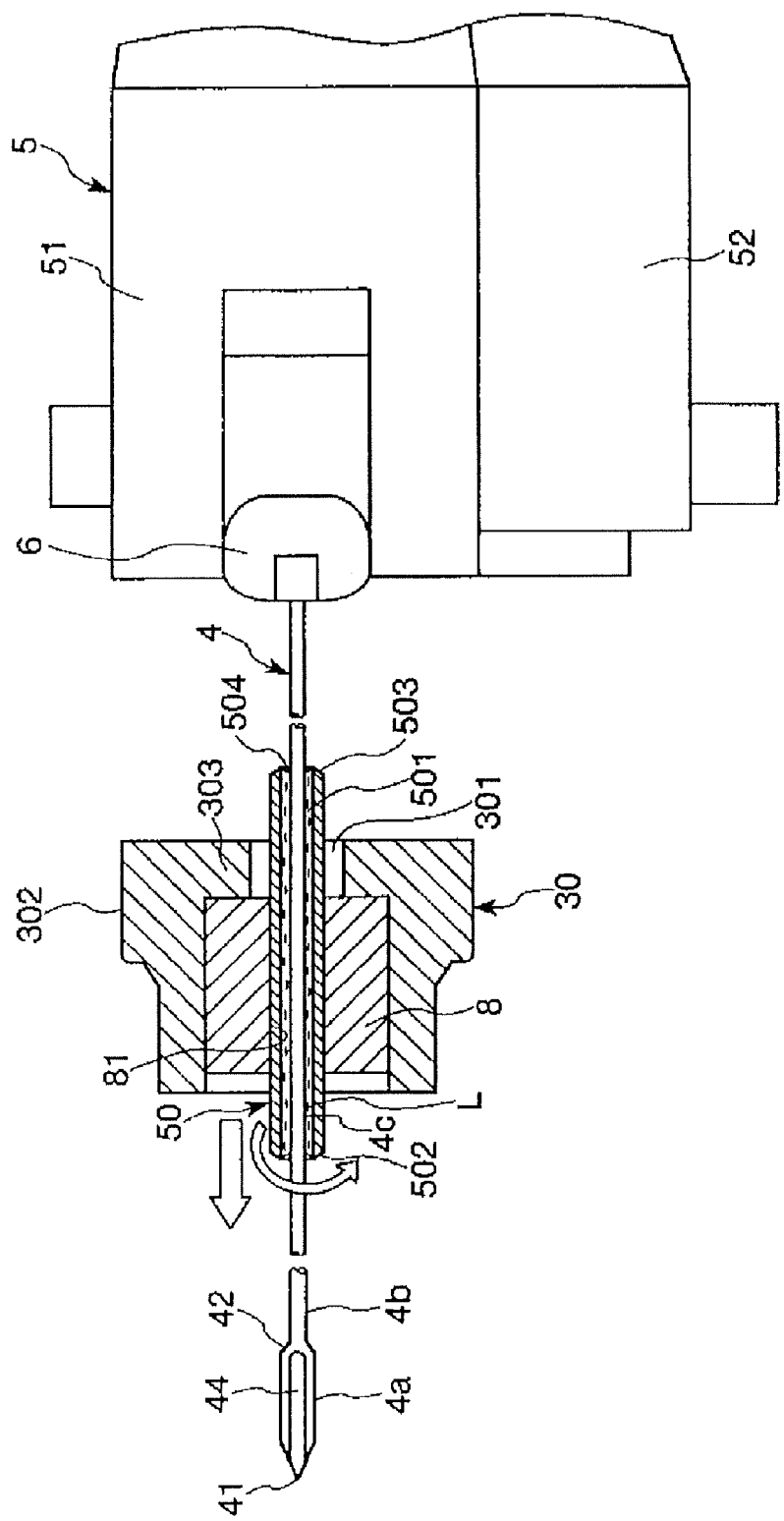
FIG. 16 is a drawing (longitudinal sectional view) for sequentially illustrating the steps (second embodiment) for producing the indwelling needle assembly shown in FIG. 1.

As shown in FIG. 14, the inner needle 4 is inserted, with the needle point 41 side thereof first, into a proximal end opening 504 of the jig 50, whereby the inner needle 4 is caused to penetrate into the jig 50 (see FIG. 15). Then, a portion of the minimum inside diameter part 4c of the inner needle 4, which is placed in firm contact with the seal member 8 in the assembled condition, and the seal member 8 are positioned so as to correspond with each other.

In the assembled condition, the inner needle 4 is inserted through the seal member 8 (see FIG. 2). In this case, i.e., where the inner needle 4 is inserted directly into the seal member 8 starting with the needle point 41 upon assembling the indwelling needle assembly 1, the needle point 41 may possibly make contact with the seal member 8 (slit 81), thus resulting in damage to the needle point 41 (for example, chipping of the cutting edge).

In the inner needle insertion step, however, the inner needle 4 is inserted into the seal member 8 through the jig 50, which has been preliminarily inserted beforehand into the seal member 8. This securely prevents the needle point 41 of the inner needle 4 from experiencing wear due to contact with the seal member 8 (slit 81). Therefore, damage to the needle point 41 (for example, chipping of the cutting edge) can securely be prevented from occurring. Stated otherwise, the needle point 41 can be securely protected.

<<A5>> Reciprocation Step

Subsequently, while the inner needle hub 5 is gripped by one hand and with the compression member 30 being gripped by the other hand, the inner needle hub 5 is reciprocated along the axial direction of the inner needle 4 (the jig 50) relative to the compression member 30 (the seal member 8), as shown in FIG. 15. Attendant on this operation, the inner needle 4, which is inserted through the jig 50, also is reciprocated along the axial direction thereof. This enables the lubricant L to be applied to the outer peripheral surface of the minimum outside diameter part 4c of the inner needle 4, over a comparatively wide range. In addition, the lubricant L is applied evenly and assuredly. When the lubricant L is applied in this manner, it is possible to reduce frictional resistance reliably between the inner needle 4 and the seal member 8 (the slit 81), at a time when the inner needle 4 is pulled out from the seal member 8, as mentioned above.

Incidentally, the number of times that the inner needle 4 is reciprocated is not particularly limited. For example, the number of times preferably is at least once, and more preferably, from 1 to 5 times.

In addition, when the reciprocating operation is performed, the operation may be carried out while rotating the inner needle 4 about its axis.

<<A6>> Jig Pulling-out Step

Next, while maintaining the positional relationship between the inner needle 4 and the seal member 8, the jig 50 is moved along the axial direction, and more specifically, is pulled in the distal direction relative to the inner needle 4 and the seal member 8. As a result, the jig 50 is pulled out of the seal member 8 (as well as the inner needle 4). In this instance, the seal member is deformed due to the elasticity (restoring force) thereof, in directions such that the slit 81 becomes closed (see FIG. 17). Consequently, the lubricant L, which has been deposited on the outer peripheral surface of the inner needle 4, also is deposited on the inner surfaces of the slit 81, or stated otherwise, the lubricant L also penetrates into the seal member 8.

Incidentally, when the jig 50 is pulled out, the operation may be performed while rotating the jig 50 about its axis. This makes it possible to carry out the pulling-out operation more easily.

<<A7>> Tube Connection Step

On the other hand, a tube 7 with a connector 72 connected thereto, and an outer needle hub 3 are prepared. Incidentally, the outer needle hub 3 is accompanied by the outer needle 2, which is already affixed thereto.

Figure 17:
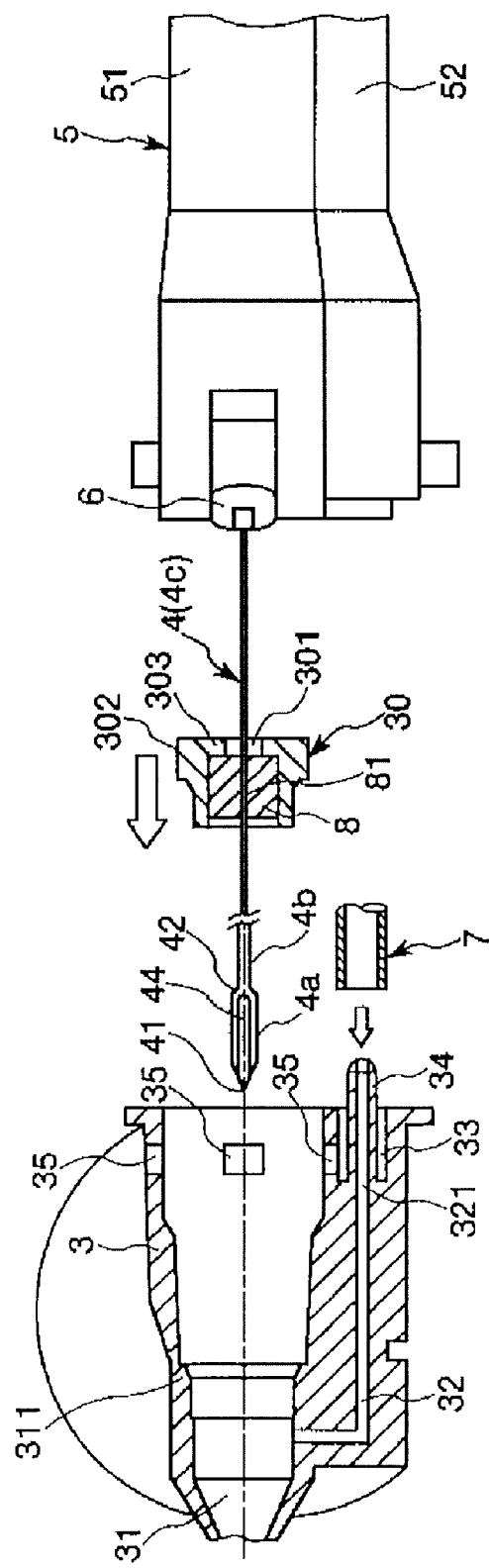
FIG. 17 is a drawing (longitudinal sectional view) for sequentially illustrating the steps (second embodiment) for producing the indwelling needle assembly shown in FIG. 1.

At an end portion, on a side thereof opposite to the connector 72, the tube 7 is inserted into a recess 33 in the outer needle hub 3, and is fitted onto a projected part 34 (see FIG. 17). This results in the tube 7 and the outer needle hub 3 being connected to each other.

<<A8>> Outer Needle Hub Fixation Step

While maintaining the positional relationship between the inner needle 4 and the seal member 8, as shown in FIG. 17, the inner needle 4, which is in the inserted condition and affixed to the inner needle hub 5, is inserted into the outer needle hub 3 from the proximal side of the outer needle hub 3, until the inner needle hub 5 abuts against the outer needle hub 3. As a result, the inner needle 4 is accommodated in the outer needle 2, the compression member 30 is fitted at the inside 31 of the outer needle hub 3, and the seal member 8 is affixed to the outer needle hub 3 through the compression member 30.

Thereafter, the tube 7, which is connected to the outer needle hub, is accommodated in a tube accommodating part 52 of the inner needle hub 5.

Through implementation of the aforementioned steps, the indwelling needle assembly 1 is produced (assembled) assuredly.

Further, when the indwelling needle assembly 1 is in the assembled condition, the lubricant L is deposited in the slit 81 and on the outer surface of the inner needle 4, whereby frictional resistance between the inner needle 4 and the seal member 8 can securely be reduced when the inner needle 4 is pulled out from the seal member 8, in a condition where the outer needle 2 has securely punctured a blood vessel. Consequently, the outer needle 2 can be moved smoothly, and the indwelling needle assembly 1 is excellent in operability during the puncturing operation.

In addition, where the inner needle 4 is formed from a metallic material, as mentioned above, due to the presence of the lubricant L, slidability of the inner needle 4 relative to the seal member 8 is enhanced, or stated otherwise, frictional resistance between the seal member 8 and the inner needle 4 can be reduced more assuredly. Consequently, operability during the pulling-out operation is excellent.

Further, since the inner needle insertion step takes place prior to the lubricant application step, fixation of the inner needle 4 to the inner needle hub 5 can be carried out more easily by use of the aforementioned fixing method.

Incidentally, although the inner needle 4, at a time of insertion into and through the jig 50, is accompanied by the inner needle hub 5 which is preliminarily fixed thereto, the invention is not limited by this feature. For example, at the time of insertion, the inner needle 4 may be used as is, i.e., without the inner needle hub 5 being preliminarily affixed thereto. In a case where the inner needle hub 5 has not been fixed to the inner needle 4, fixation of the inner needle hub 5 can be performed after the inner needle 4 has been inserted through the jig 50.

In addition, in the method of producing the indwelling needle assembly 1 according to the present invention, the jig 50 can be reused each time that an indwelling needle assembly 1 is produced, namely, at each time of production. After production of one indwelling needle assembly 1, another indwelling needle assembly 1, which is separate from the one indwelling needle assembly 1, can be produced. In the case that the jig 50 is reused, the jig 50 that has already been used (i.e., a used jig 50) preferably is subjected to cleaning and sterilizing treatments, before it is used again.

Since the jig 50 is reusable, preparation of an unused jig 50 each time that an indwelling needle assembly 1 is produced can be omitted.

Further, although the method of applying the lubricant L to the outer peripheral surface of the inner needle 4 by immersing the inner needle 4 in the lubricant L (immersion method) has been used in the lubricant application step, the invention is not limited by this feature. For example, a method of applying the lubricant L by spraying, or by use of a dropping pipette or the like, may also be used.

In addition, while the seal member 8 preliminarily formed with the slit 81 therein has been used in the jig insertion step, the invention is not limited by this feature. For example, a seal member 8, which does not have a slit 81 formed therein may also be used. In this case, by inserting the jig 50 into and through the seal member 8 (causing the jig 50 to penetrate through the seal member 8), a slit (through-hole) is formed.

Further, while the jig 50 is provided at a proximal portion thereof with the tapered part where the outside diameter decreases gradually along the proximal direction, the invention is not limited by this feature. For example, a rounded part having a rounded shape may also be provided.

In addition, in the jig insertion step, the inner needle 4 is inserted into and through the seal member 8 in the pressed-in condition, namely, in a condition where the seal member 8 has been pressed into the compression member 30, however, the invention is not limited to this procedure. Namely, the jig 50 may be inserted into and through the seal member 8 as is, or more specifically, in a condition where the seal member 8 has not yet been pressed into the compression member 30.

Further, the jig 50 is provided at both end portions thereof with tapered parts, where the outside diameter decreases gradually, however, the invention is not limited by this feature. The jig 50 may have a tapered part at only one end portion thereof.

In addition, while the jig 50 is annular (in the shape of the letter "O") in cross-sectional shape, the invention is not limited by this feature. The cross-sectional shape may be the shape of the letter "C," the shape of the letter "V," or the shape of the letter "U."

<Third Embodiment>

Figure 18:
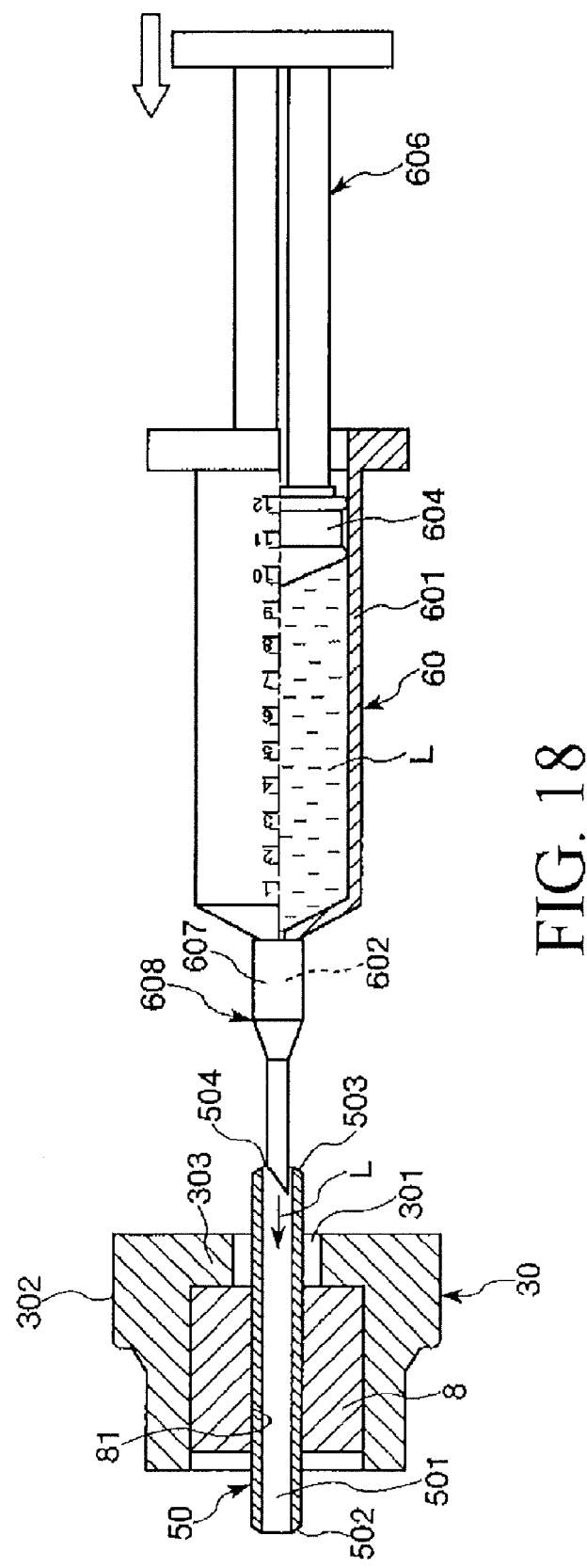
FIG. 18 is a drawing (longitudinal sectional view) for sequentially illustrating steps (third embodiment) for producing the indwelling needle assembly according to the invention.
Figure 19:
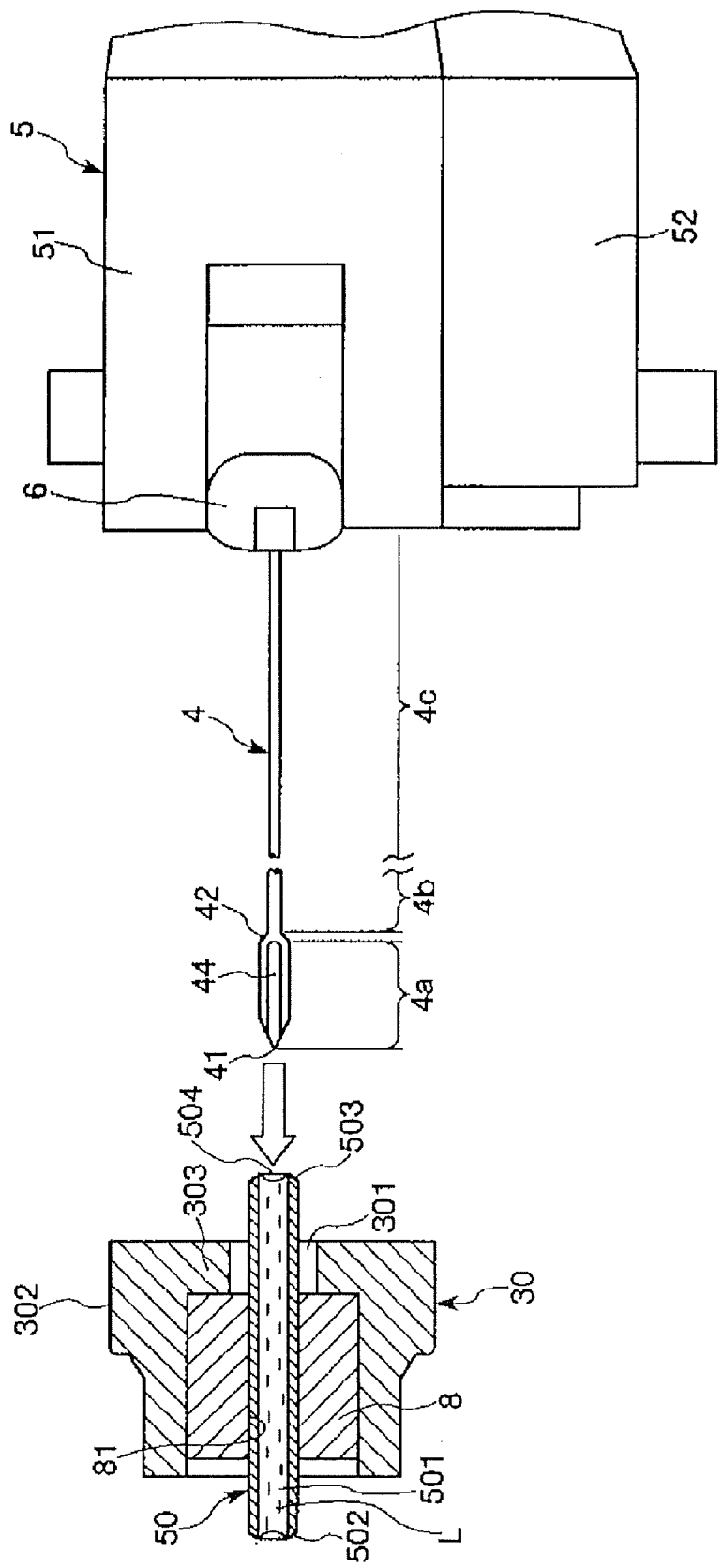
FIG. 19 is a drawing (longitudinal sectional view) for sequentially illustrating the steps (third embodiment) for producing the indwelling needle assembly according to the invention.

FIGS. 18 and 19 are drawings (longitudinal sectional views) for sequentially illustrating steps (third embodiment) for producing the indwelling needle assembly according to the present invention.

Next, referring to these figures, a third embodiment of the method of producing an indwelling needle assembly and the indwelling needle assembly according to the present invention will be described below. The following description will be centered on differences from the above-described embodiments, and descriptions of the same items utilized therein shall be omitted.

This embodiment is the same as the second embodiment above, except for differences in a part of the steps used for producing the indwelling needle assembly.

In this embodiment, steps ranging from the <<B1>> inner needle hub fixation step to the <<B2>> jig insertion step are the same as the steps ranging from the <<A1>> inner needle hub fixation step to the <<A2>> jig insertion step, as described in the first embodiment above.

<<B3>> Lubricant Filling Step

In this step, a syringe (injection container) preliminarily filled with a lubricant L is prepared.

The syringe 60 includes an outer tube (syringe outer tube) 601, a gasket 604 that can be slid inside the outer tube 601, and a plunger (plunger rod) 606, which is operable to move the gasket 604 along the longitudinal direction (axial direction) of the outer tube 601 (see FIG. 18). The gasket 604 is linked to the distal end of the plunger rod 606.

The outer tube 601 is composed of a member, which has a bottomed tubular shape. At a central portion of a distal-side bottom part of the outer tube 601, a mouth part (reduced diameter part) 602, which is reduced in diameter as compared with a barrel part of the outer tube 601, is formed integrally and in a projecting manner. A needle pipe 608 is mounted onto the mouth part 602 through a needle hub 607.

In addition, the outer peripheral surface of the outer tube 601 is provided with graduations thereon for indicating the amount of liquid.

Examples of materials for the outer tube 601 and the plunger rod 606 include various resins, such as polyvinyl chloride, polyethylene, polypropylene, and cyclic polyolefins. Incidentally, it is preferable for the material constituting the outer tube 601 to be substantially transparent, for enabling the inside thereof to be visible.

Materials used for the gasket 604 are not particularly limited. Examples of suitable materials include elastic materials, such as various rubber materials such as natural rubber, butyl rubber, isoprene rubber, butadiene rubber, styrene-butadiene rubber, silicone rubbers, etc., various thermoplastic elastomers based on polyurethane, polyester, polyamide, olefin, styrene or the like, as well as mixtures thereof.

In this step, the aforementioned syringe 60 may be used.

As shown in FIG. 18, a distal portion of the needle pipe 608 of the syringe 60 is inserted into a lumen 501 of a jig 50 in a jig-inserted condition. In this condition, the plunger rod 606 of the syringe 60 is pushed along the distal direction. This causes the lubricant L to flow out from the needle pipe 608, and to be injected into (fill) the lumen 501 of the jig 50 assuredly.

<<B4>> Lubricant Application Step

Next, the jig 50 (inclusive of a seal member 8 and a compression member 30), which is in the jig-inserted condition and filled with the lubricant L as produced in the aforementioned lubricant filling step, and an inner needle 4 with an inner needle hub 5 affixed thereto, which is produced (assembled) in the aforementioned inner hub fixation step, are prepared.

The inner needle 4 is inserted, with the side of the needle point 41 first, into a proximal end opening 504 of the jig 50 (see FIG. 19), whereupon the inner needle 4 is made to penetrate into the jig 50. Then, a portion of a minimum outside diameter part 4c of the inner needle 4 that is placed in firm contact with the seal member 8 in an assembled condition, and the seal member 8, are positioned so as to correspond with each other. This enables the lubricant L to be applied easily and assuredly to an outer peripheral surface of the inner needle 4, particularly to the outer peripheral surface of the minimum outside diameter part 4c corresponding to the seal member 8, in the assembled condition.

The steps subsequent to the foregoing step are the same as the steps ranging from the <<A5>> reciprocation step to the <<A8>> outer needle hub fixation step, as described in the second embodiment above.

By means of the aforementioned steps, the indwelling needle assembly 1 can be produced (assembled) assuredly.

<Fourth Embodiment>

Figure 20:
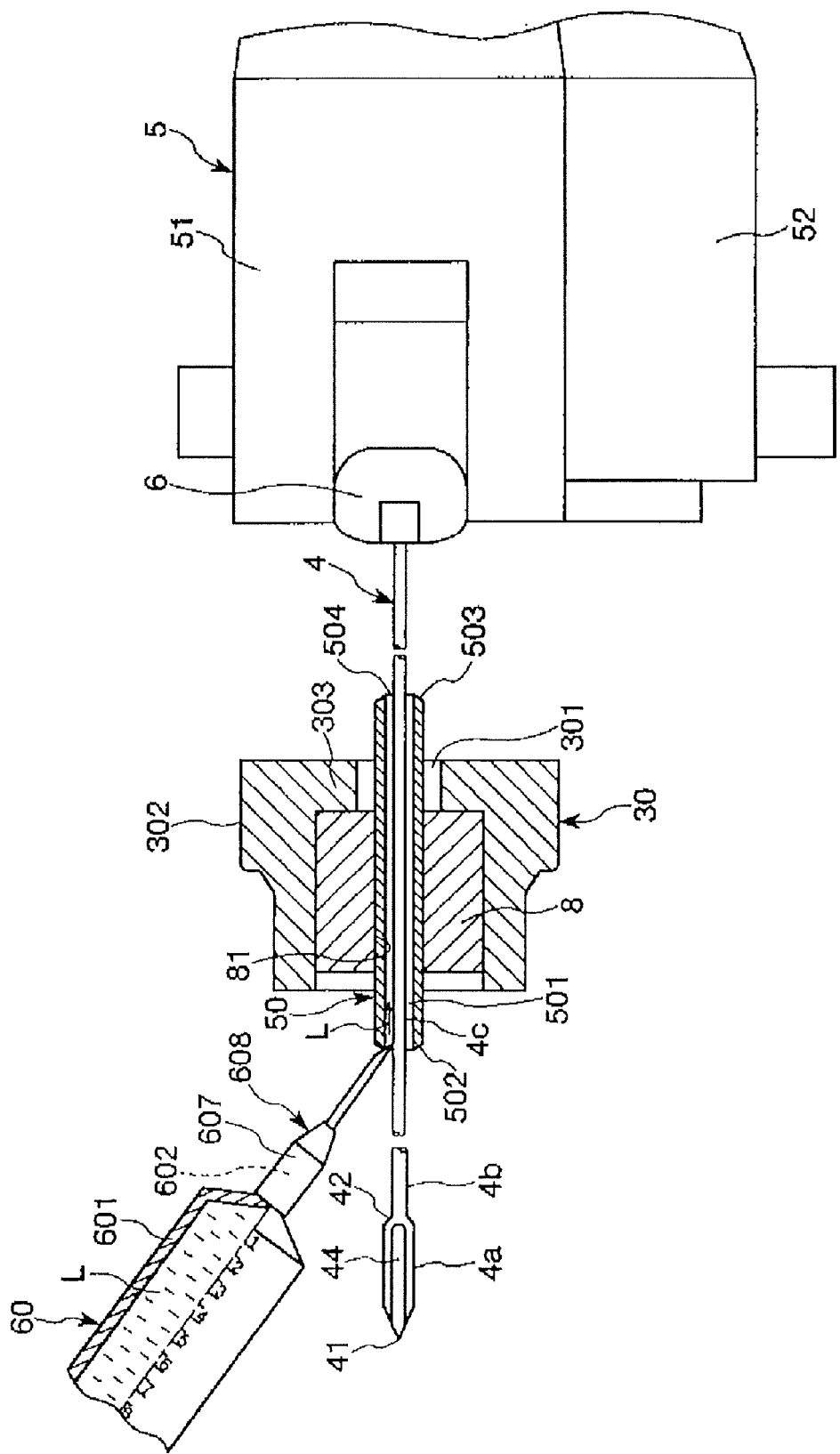
FIG. 20 is a drawing (longitudinal sectional view) for illustrating a step (fourth embodiment) for producing the indwelling needle assembly according to the invention.

FIG. 20 is a drawing (longitudinal sectional view) illustrating a step (fourth embodiment) for producing the indwelling needle assembly according to the present invention.

Next, referring to the figure, a fourth embodiment of the method of producing an indwelling needle assembly, and an indwelling needle assembly produced thereby according to the present invention, will be described below. The following description will be centered on differences thereof from the above-described embodiments, wherein descriptions of the same items discussed above shall be omitted.

The present embodiment is the same as the second embodiment above, except for differences in a part of the steps used for producing the indwelling needle assembly.

In this embodiment, the steps ranging from the <<C1>> inner needle hub fixation step to the <<C2>> jig insertion step are carried out in the same manner as the steps ranging from the <<A1>> inner needle hub fixation step to the <<A2>> jig insertion step, as described in the second embodiment above.

<<C3>> Inner Needle Insertion Step

An inner needle 4 with an inner needle hub 5 affixed thereto, which is assembled in the aforementioned inner needle hub fixation step, is prepared along with a jig 50 in a jig-inserted condition, which is assembled in the aforementioned jig insertion step.

As shown in FIG. 20, the inner needle 4 is inserted, with the side of the needle point 41 first, into a proximal end opening 504 of the jig 50, whereby the inner needle 4 is made to penetrate into the jig 50. Then, a portion of a minimum outside diameter part 4c of the inner needle 4, which is to be placed in firm contact with a seal member 8 in the assembled condition, and the seal member 8 are positioned so as to correspond to each other.

<<C4>> Lubricant Application Step

Next, a syringe 60 filled with a lubricant L is prepared, and a distal portion of a needle pipe 608 of the syringe 60 is inserted into (disposed in) a gap formed between an inner peripheral part of the jig 50 and the inner needle 4. In this condition, a plunger rod 606 of the syringe 60 is pushed. Such pushing causes the lubricant L to flow out from the needle pipe 608, and to be injected into (fill) the gap (lumen 501) between the jig 50 and the inner needle 4. Consequently, it is possible to apply the lubricant L easily and assuredly to an outer peripheral surface of the inner needle 4, and in particular, to the outer peripheral surface of the minimum outside diameter part 4c that corresponds to the seal member 8 in the assembled condition.

The steps subsequent to the aforementioned step are the same as the steps ranging from the <<A5>> reciprocation step to the <<A8>> outer needle hub fixation step, which were described in connection with the second embodiment.

By implementing the aforementioned steps, the indwelling needle assembly 1 can be produced (assembled) reliably.

<Fifth Embodiment>

FIGS. 21 to 28 are drawings for sequentially illustrating steps (fifth embodiment) for producing the indwelling needle assembly shown in FIG. 1. Incidentally, in the following descriptions, the right side in FIGS. 21 to 23 and 26 to 28 will be referred to as "proximal," and the left side as "distal."

Next, referring to the figures, a fifth embodiment of the method of producing an indwelling needle assembly, and the indwelling needle assembly produced thereby according to the present invention, will be described below. The following description shall be centered on differences from the above-described embodiments, and descriptions of the same items which are the same as in the foregoing embodiments will be omitted.

The present embodiment is the same as the first embodiment above, except for differences in the steps used to produce the indwelling needle assembly.

The method of producing the indwelling needle assembly 1 according to the present embodiment will be described below with reference to FIGS. 21 to 28.

The method of producing the indwelling needle assembly 1 includes an insertion step (first step), an inner needle hub fixation step (second step), a slit opening step (third step), a lubricant supply step (fourth step), a lubricant penetration step (fifth step), a seal member accommodation step (sixth step), a tube connection step (seventh step), and an outer needle hub fixation step (eighth step). The steps are carried out sequentially.

<<A1>> Insertion Step

Figure 21:
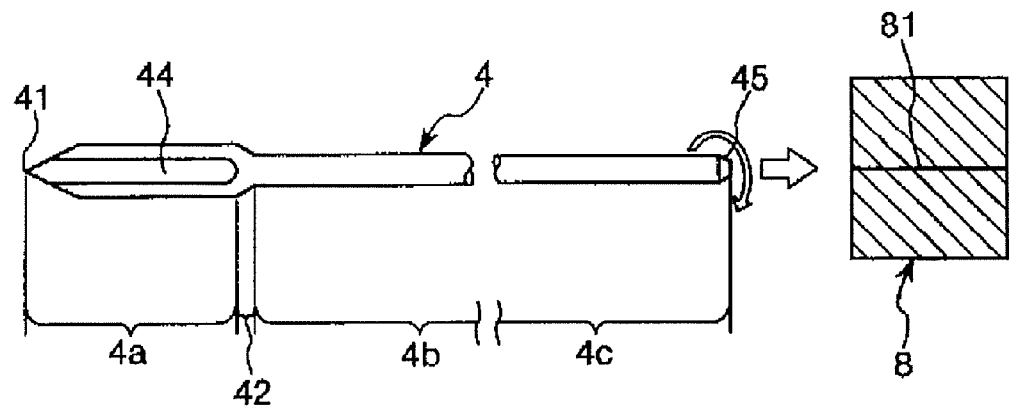
FIG. 21 is a drawing for sequentially illustrating steps (fifth embodiment) for producing the indwelling needle assembly shown in FIG. 1.

First, as shown in FIG. 21, a seal member 8 and an inner needle 4 are prepared.

The seal member 8 is preliminarily formed with a slit 81 therein, which ensures that the operation of inserting the inner needle 4 (insertion operation), to be described later, can be carried out easily.

In addition, a proximal portion 45 of the inner needle 4 may be formed with a tapered part, where the outside diameter decreases gradually along the proximal direction. Alternatively, the proximal portion 45 may consist of a simple flat surface. The inner needle 4 is inserted through (into) the slit 81 of the seal member 8, starting with a side thereof opposite to the needle point 41, namely, starting with the proximal portion 45. The insertion operation can be carried out more easily, owing to the synergistic effect of the tapered part, which is provided on the proximal portion 45 of the inner needle 4, and the slit 81, which is preliminarily formed in the seal member 8.

Figure 22:
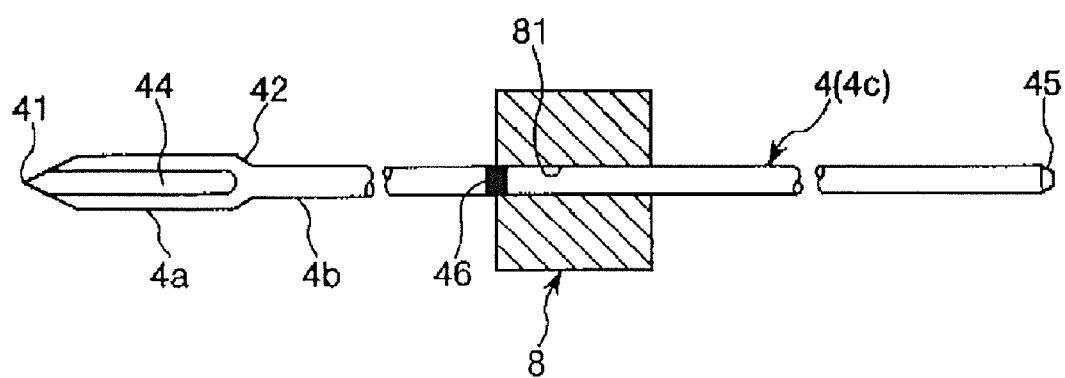
FIG. 22 is a drawing for sequentially illustrating the steps (fifth embodiment) for producing the indwelling needle assembly shown in FIG. 1.

When the inner needle 4 is pushed in further toward the proximal side, the proximal portion 45 thereof reaches beyond the seal member 8, and protrudes toward the proximal side of the seal member 8. Further, in this instance, a predetermined position of a minimum outside diameter part 4c of the inner needle 4 is disposed within the slit 81, thereby positioning the inner needle 4 relative to the seal member 8. Incidentally, as shown in FIG. 22, the minimum outside diameter part 4c of the inner needle 4 may be provided with a marker 46 thereon for positioning. This enables positioning of the inner needle 4 to be carried out easily. The marker 46 can be provided, for example, at a portion of the inner needle 4 that corresponds to the distal end face (the end face on one side) of the seal member 8.

The condition of the seal member 8 and the inner needle 4, which are assembled together in this manner, will be referred to as an "inserted condition" (see FIG. 22).

In the insertion step, when the inserted condition is obtained, the inner needle 4 is inserted into the seal member 8, starting with the side of the proximal portion 45. Therefore, wearing of the needle point 41 of the inner needle 4 due to making contact with the seal member 8 (the slit 81) can be securely prevented from occurring. This ensures that damage to the needle point 41 (for example, chipping of the cutting edge) can securely be prevented from occurring. In other words, the needle point 41 can be securely protected.

In addition, when the inner needle 4 is inserted into and through the seal member 8, the insertion operation may be conducted while the inner needle 4 is rotated about its axis. This enables the insertion operation to be carried out more easily.

<<A2>> Inner Needle Hub Fixation Step

Next, an inner needle hub 5, with a protector 9 assembled (accommodated) therein, and a compression member 30 are prepared.

The compression member 30 is disposed such that the flange 302 thereof is located on the proximal side, whereas the inner needle 4 in the inserted state is disposed such that the proximal portion 45 is located on the proximal side. Disposed in this manner, the inner needle 4 in the inserted condition is inserted into the compression member 30, starting from the proximal portion 45 thereof. Then, the compression member 30 is disposed at an intermediate portion of the minimum outside diameter part 4c of the inner needle 4, so that the seal member 8 does not become accommodated within the compression member 30.

Thereafter, the inner needle 4 along with the compression member 30 is inserted into the inner needle hub 5 (the protector 9), starting from the proximal portion 45 thereof. As a result, the proximal portion 45 of the inner needle 4 passes through an inner needle passage 931 in the protector 9, and arrives at (reaches) a projected part 512 of the inner needle hub 5. The proximal portion 45 of the inner needle 4 is inserted into a hole 513, and is affixed to the projected part 512, for example, through a fitting. Consequently, the inner needle hub 5 and the inner needle 4 are assembled together, with the inner needle 4 being fixed to the inner needle hub 5 (see FIG. 23).

<<A3>> Slit Opening Step

Figure 23:
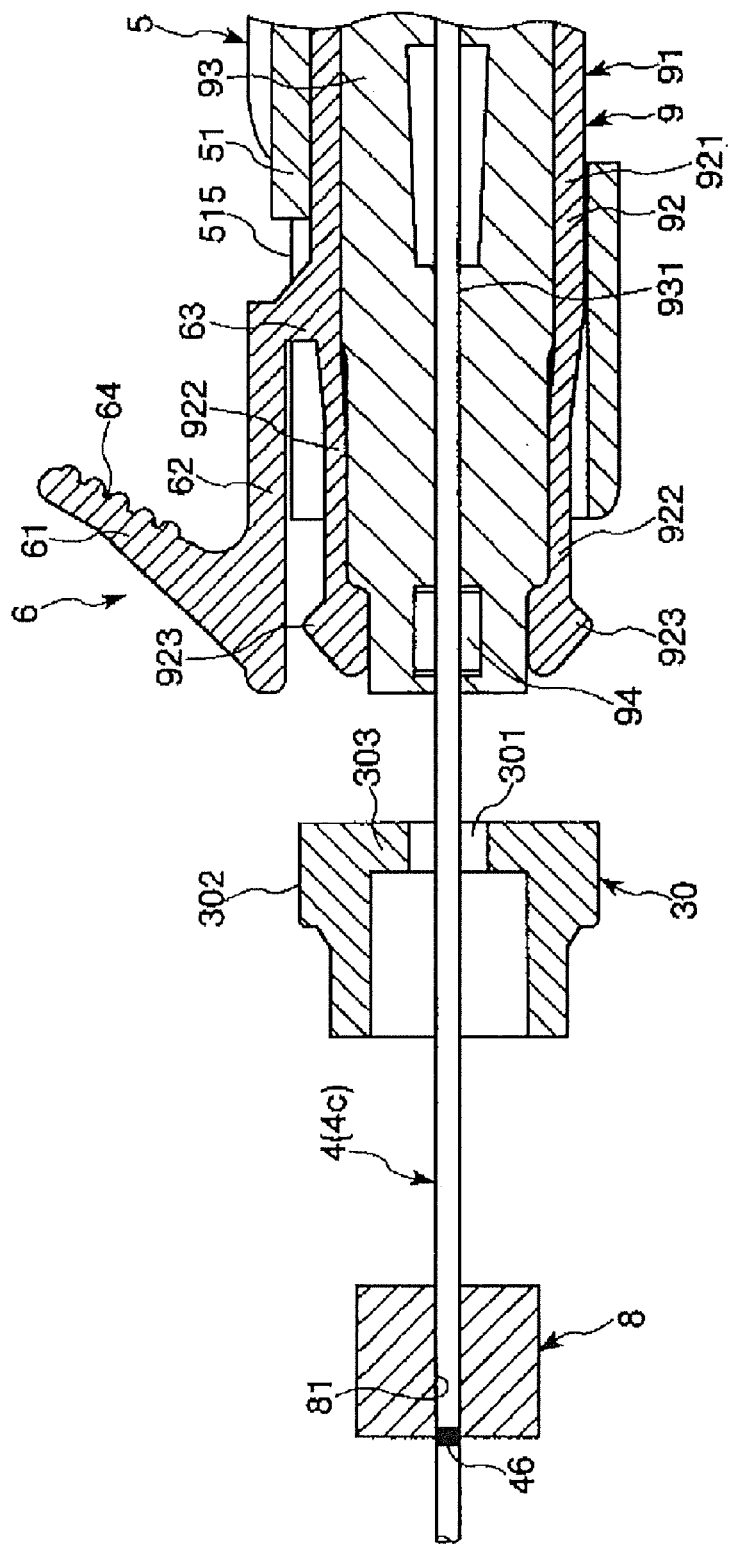
FIG. 23 is a drawing for sequentially illustrating the steps (fifth embodiment) for producing the indwelling needle assembly shown in FIG. 1.
Figure 24:
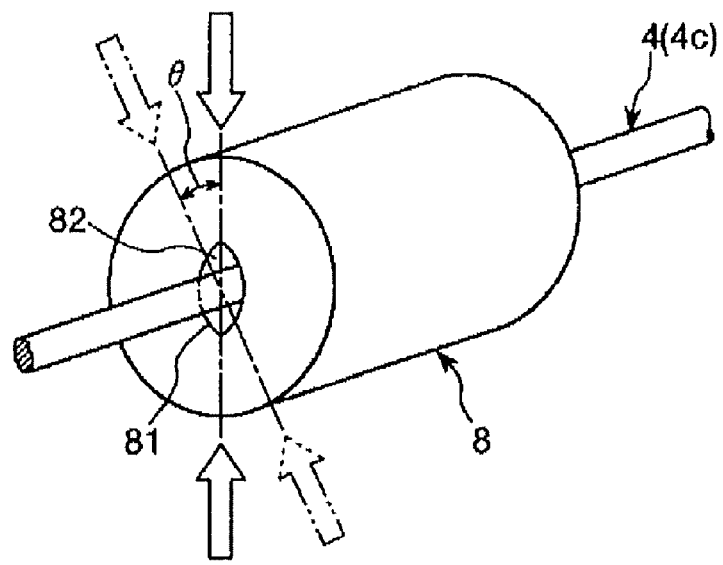
FIG. 24 is a drawing for sequentially illustrating the steps (fifth embodiment) for producing the indwelling needle assembly shown in FIG. 1.
Figure 25:
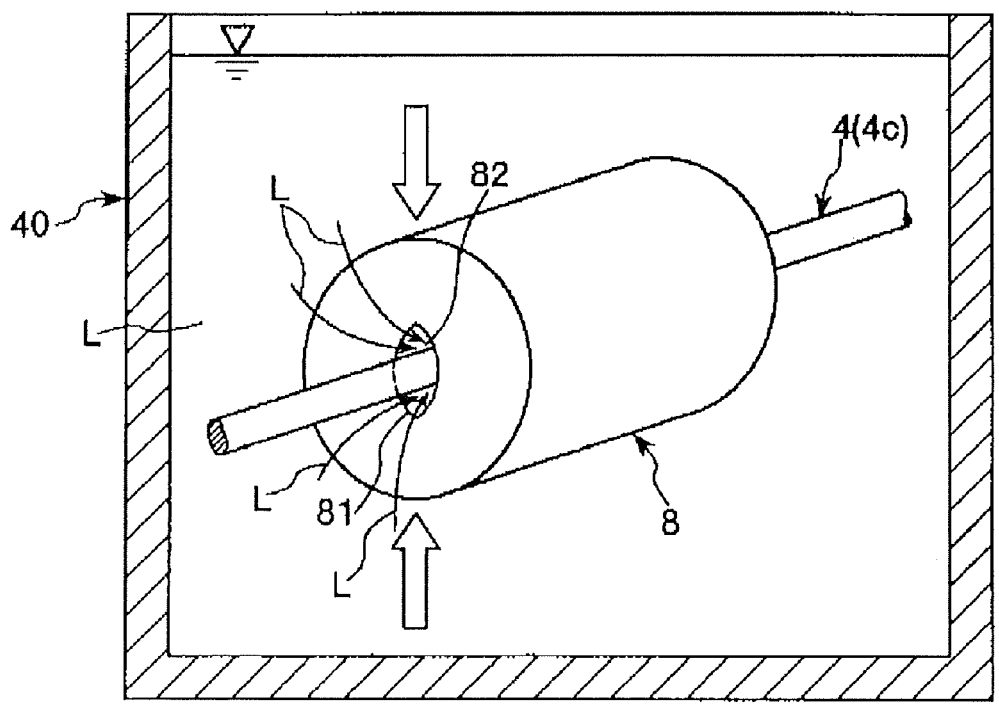
FIG. 25 is a drawing for sequentially illustrating the steps (fifth embodiment) for producing the indwelling needle assembly shown in FIG. 1.

Subsequently, in the condition shown in FIG. 23, the seal member 8 is compressed in a direction to open the slit 81, namely, in the direction in which the slit 81 is formed (i.e., in the vertical direction in FIG. 24). This enables the slit 81 to be opened securely, as shown in FIG. 24. As a result, a gap 82 is generated between the inner surface of the slit 81 and the outer peripheral surface of the inner needle 4.

Incidentally, compression of the seal member 8 may be conducted with the fingers, or may be performed by use of a pinching tool (for example, a pair of pincers or the like).

In addition, the direction in which the seal member 8 is compressed is not limited to a direction in which the slit 81 is formed, and the seal member 8 may be compressed in a direction which is inclined at a predetermined angle θ with respect to the direction in which the slit 81 is formed. The angle θ in this case is not particularly limited, and may be 0° to 45°, for example.

<<A4>> Lubricant Supply Step

Next, a reservoir 40, which is filled with a liquid lubricant (lubricating liquid) L, is prepared. Then, the seal member 8 (inclusive of the inner needle 4) in the condition shown in FIG. 24, and more specifically, in a condition where the slit 81 is opened, is immersed in the reservoir 40. As a result, a capillary action takes place between the slit 81 and the inner needle 4, whereby the lubricant L flows into the gap 82, and therefore the lubricant L is supplied into the gap 82 (the opened slit 81).

By such an immersion method, the lubricant L can readily be applied not only to a portion of the inner needle 4 that protrudes from the seal member 8, but also to inner surfaces of the slit 81 and to a portion of the outer surface of the inner needle 4, which is located inside the slit 81.

Further, when the inner needle 4 is immersed in the reservoir 40, such an operation can easily be carried out by gripping the inner needle hub 5, which is not immersed in the reservoir 40. Thus, the inner needle hub 5 functions as a grip part, which is gripped by the worker during immersion of the inner needle 4 in the reservoir 40.

In addition, the reservoir 40 has a size such that when the inner needle 4 (inclusive of the seal member 8) is immersed, the portion of the inner needle 4 that is to be immersed can be accommodated assuredly.

Further, the lubricant L is not particularly limited. Examples of lubricants which can be used include lubricants comprised mainly of silicone, particularly, silicone oils, reactive silicones, and mixtures thereof. Reactive silicones are silicones which can be cured by heat or radiation. When a reactive silicone is used, the silicone remains on inner surfaces of the slit 81 in the seal member 8 and on the surface of the inner needle 4 for a long time, so that the effect thereof on reducing friction between the inner needle 4 and the seal member 8 is maintained. In addition, the mixing ratio utilized when mixing silicone oil with reactive silicone ("amount of silicone oil": "amount of reactive silicone") is not particularly limited. For example, the mixing ratio is preferably in a range from 1:9 to 9:1, and more preferably, from 2:8 to 8:2.

<<A5>> Lubricant Penetration Step

Subsequently, the inner needle 4, the seal member 8 and the compression member 30 are drawn up (taken out) from the reservoir 40.

In addition, compression on the seal member 8 is released. As a result, the slit 81 is closed again.

Figure 26:
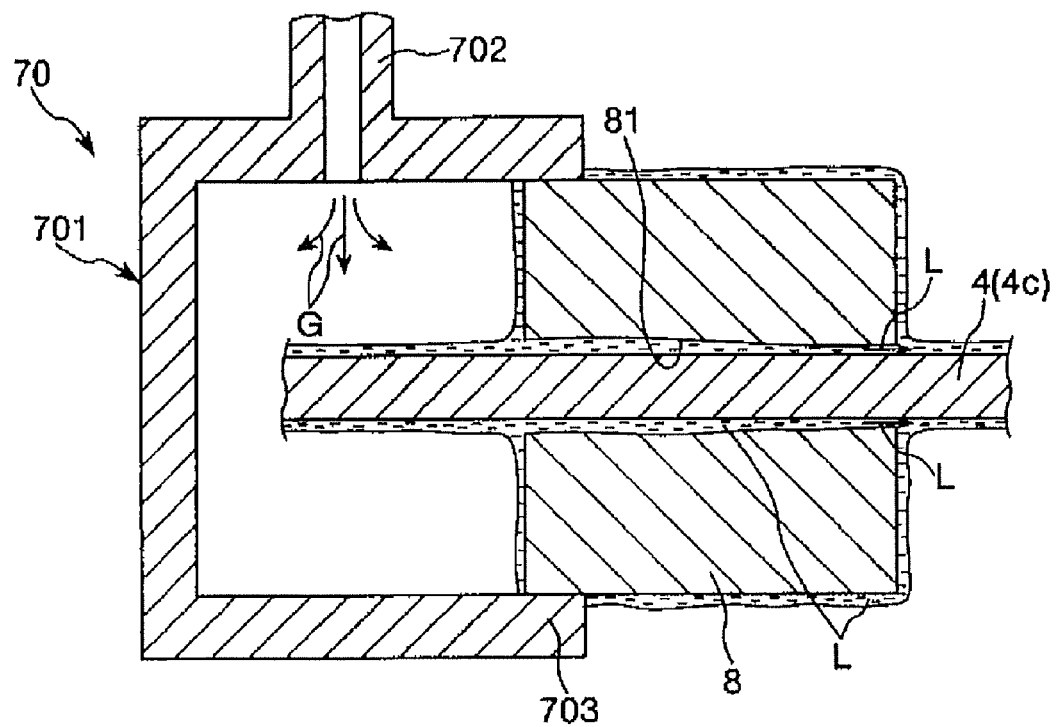
FIG. 26 is a drawing for sequentially illustrating the steps (fifth embodiment) for producing the indwelling needle assembly shown in FIG. 1.

On the other hand, a pressure device 70 is prepared. As shown in FIG. 26, the pressure device 70 includes a chamber (pressure chamber) 701 having an installation part 703, to which a distal portion of the seal member 8 may be detachably mounted, and a connecting pipe 702 for connecting the chamber 701 and a pressure pump (not shown) to each other.

Then, as shown in FIG. 26, the distal portion of the seal member 8 is mounted to (fitted into) the installation part 703 of the chamber 701. As a result, the inside of the chamber 701 is placed in an air-tight state.

Under this condition, when the pressure pump is operated, air G flows from the pressure pump into the chamber 701 through the connecting pipe 702. This results in the inside of the chamber 701 becoming pressurized, whereby the pressure inside the chamber 701 is raised. In this instance, the lubricant L present inside the slit 81, and the lubricant L deposited on the portion of the inner needle 4 that is on the distal side relative to the seal member 8, are pushed (made to flow) along the proximal direction inside the slit 81. This causes the lubricant L to penetrate further into the slit 81, or in other words, penetration of the lubricant L into the slit 81 is promoted. Therefore, the slit 81 can reliably be supplied with the lubricant L over the entire range thereof along the longitudinal direction.

As a result of the lubricant L having thus entered into the slit 81, frictional resistance between the inner needle 4 and the seal member 8 (the slit 81) can be reduced when the inner needle 4 is pulled out from the seal member 8, as mentioned above.

<<A6>> Seal Member Accommodation Step

Next, the seal member 8 is dismounted from the pressure device 70.

Figure 27:
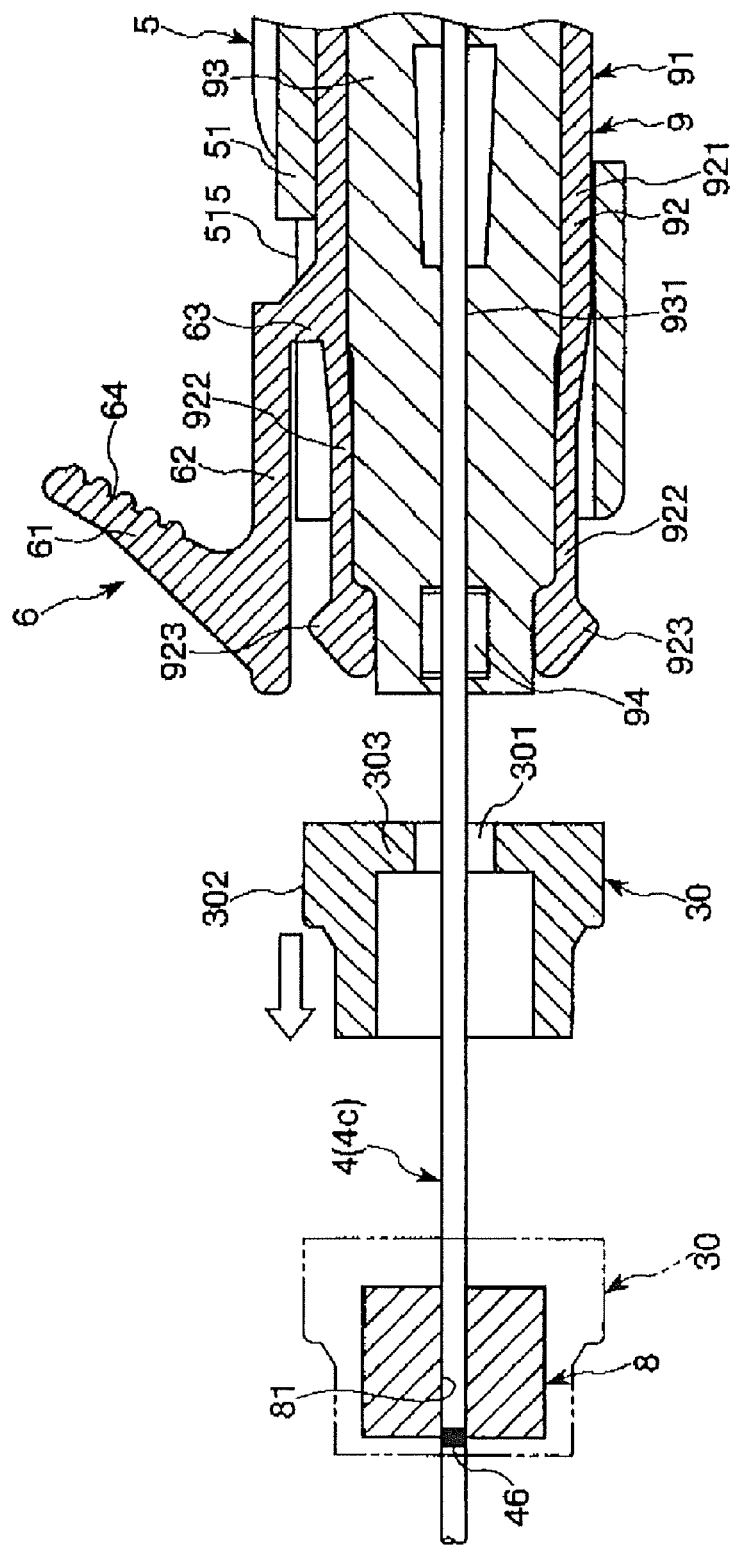
FIG. 27 is a drawing for sequentially illustrating the steps (fifth embodiment) for producing the indwelling needle assembly shown in FIG. 1.

Thereafter, as shown in FIG. 27, the compression member 30 is moved in the distal direction along the inner needle 4, so as to accommodate the seal member 8 in the compression member 30 (refer to the part (compression member 30) indicated by the two-dotted chain line in FIG. 27), resulting in a pressed-in condition.

<<A7>> Tube Connection Step

Subsequently, a tube 7 having a connector 72 connected thereto, and an outer needle hub 3 are prepared.

Figure 28:
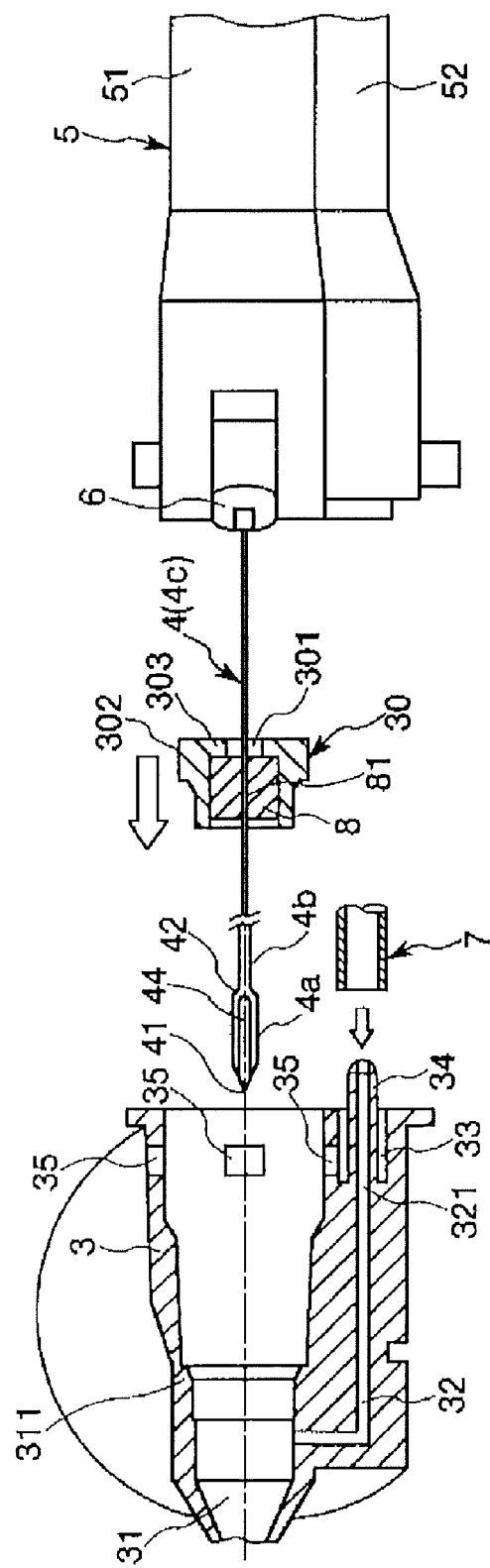
FIG. 28 is a drawing for sequentially illustrating the steps (fifth embodiment) for producing the indwelling needle assembly shown in FIG. 1.

An end portion of the tube 7, on a side opposite to the connector 72, is inserted into a recess 33 of the outer needle hub 3, whereby the tube 7 is fitted onto a projected part 34 (see FIG. 28). As a result, the tube 7 and the outer needle hub 3 are connected to each other.

<<A8>> Outer Needle Hub Fixation Step

Next, the outer needle hub 3, with the tube 7 connected thereto, is prepared. The outer needle hub 3 already has the outer needle 2 affixed thereto.

While maintaining the positional relationship between the inner needle 4 and the seal member 8, as shown in FIG. 28, the inner needle 4 in the inserted condition is inserted into the outer needle hub 3 from the proximal side of the outer needle hub 3, until the inner needle hub 5 abuts against the outer needle hub 3. As a result, the inner needle 4 is accommodated in the outer needle 2, the compression member 30 is fitted into the inside 31 of the outer needle hub 3, and the seal member 8 is affixed to the outer needle hub 3 through the compression member 30.

Thereafter, the tube 7 is accommodated inside a tube accommodating part 52 of the inner needle hub 5.

By means of the aforementioned steps, the indwelling needle assembly 1 can be produced (assembled) assuredly.

Incidentally, the method of producing the indwelling needle assembly 1 may include, after the lubricant penetration step <<A5>>, a step of removing the lubricant L, which has been deposited on a portion (exposed portion) of the inner needle 4 that protrudes from the seal member 8.

Further, in the indwelling needle assembly 1, in the assembled condition, the lubricant L is deposited on the slit 81 as well as on the outer surface of the inner needle 4. Therefore, when the inner needle 4 is pulled out from the seal member 8 in a condition where a blood vessel has been securely punctured by the outer needle 2, frictional resistance between the inner needle 4 and the seal member 8 can be reduced assuredly. This ensures that the outer needle 2 can be moved smoothly, and that the indwelling needle assembly 1 is excellent in operability when the puncturing operation is performed.

In addition, in the case that the inner needle 4 is formed from a metallic material, as previously mentioned, due to the presence of the lubricant L, slidability of the inner needle 4 relative to the seal member 8 is enhanced, or in other words, frictional resistance between the seal member 8 and the inner needle 4 can be reduced more securely. Consequently, excellent operability during the pulling-out operation is ensured.

Further, in the lubricant penetration step, penetration of the lubricant L may be promoted by reciprocating the inner needle 4 in the axial direction thereof.

In addition, in the method of producing the indwelling needle assembly according to the present embodiment, the lubricant penetration step may be omitted.

<Sixth Embodiment>

Figure 29:
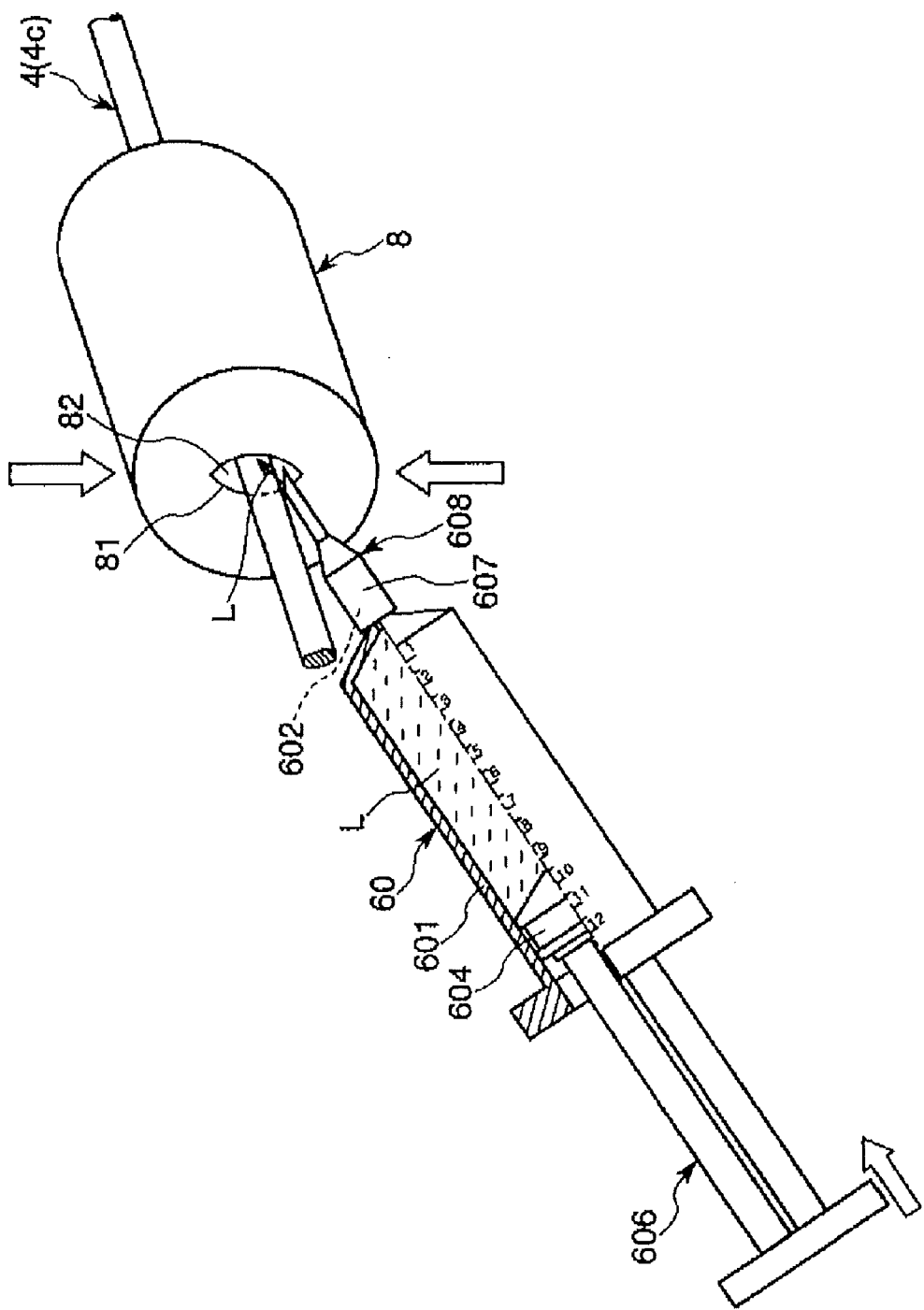
FIG. 29 is a drawing for illustrating a step (sixth embodiment) for producing the indwelling needle assembly according to the invention.

FIG. 29 is a drawing illustrating steps (sixth embodiment) for producing the indwelling needle assembly according to the present invention.

Next, referring to the figure, a sixth embodiment of the method of producing an indwelling needle assembly, as well as the indwelling needle assembly produced thereby according to the present invention, will be described below. The following description will be centered on differences from the aforementioned embodiments, in which detailed descriptions of the same items have been omitted.

The present embodiment is the same as the fifth embodiment above, except for differences in a portion of the steps used for producing the indwelling needle assembly.

In this embodiment, steps ranging from the <<B1>> insertion step through the <<B2>> inner needle hub fixation step to the <<B3>> slit opening step are the same as the steps ranging from the <<A1>> insertion step to the <<A3>> slit opening step, as described in connection with the fifth embodiment above.

<<B4>> Lubricant Supply Step

In this step, a syringe (injection container) preliminarily filled with a lubricant L is prepared.

The syringe 60 includes an outer tube (syringe outer tube) 601, a gasket 604 which is slidable inside of the outer tube 601, and a plunger (plunger rod) 606 that operates to move the gasket 604 along the longitudinal direction (axial direction) of the outer tube 601 (see FIG. 29). The gasket 604 is linked to the distal end of the plunger rod 606.

The outer tube 601 is composed of a member, which is in the shape of a bottomed tube. At a central portion of a distal-side bottom part of the outer tube 601, a mouth part (reduced diameter part) 602, which is reduced in diameter as compared with a barrel part of the outer tube 601, is formed integrally therewith in a projecting manner. A needle pipe 608 is mounted onto the mouth part 602 through a needle hub 607.

In addition, the outer peripheral surface of the outer tube 601 is provided with graduations thereon for indicating the amount of liquid.

Examples of materials for the outer tube 601 and the plunger rod 606 include various resins, such as polyvinyl chloride, polyethylene, polypropylene, and cyclic polyolefins. Incidentally, it is preferable for the material constituting the outer tube 601 to be substantially transparent, to enable the inside thereof to be visible.

Materials used for the gasket 604 are not particularly limited. Examples of such materials include elastic materials, made up of various rubber materials such as natural rubber, butyl rubber, isoprene rubber, butadiene rubber, styrene-butadiene rubber, silicone rubbers, etc., various thermoplastic elastomers based on polyurethane, polyester, polyamide, olefin, styrene or the like, and mixtures thereof.

In this step, a syringe 60 may be used.

As shown in FIG. 29, a distal portion of a needle pipe 608 of the syringe 60 is inserted into a gap 82, which is formed in a seal member 8 while being compressed. Under this condition, the plunger rod 606 of the syringe 60 is pressed. This causes the lubricant L to flow out from the needle pipe 608, and to be injected into (fill) the gap 82 assuredly. Therefore, the lubricant L can be applied assuredly to inner surfaces of the slit 81, as well as to a portion of the outer surface of the inner needle 4 that is located within the slit 81.

The steps subsequent to the aforementioned step are carried out in the same manner as the steps ranging from <<A5>> lubricant penetration step to <<A8>> outer needle hub fixation step, which have been described above in connection with the fifth embodiment.

Through the aforementioned steps, the indwelling needle assembly 1 is produced (assembled) reliably.

<Seventh Embodiment>

FIGS. 30 to 36 are drawings for sequentially illustrating steps (seventh embodiment) for producing the indwelling needle assembly shown in FIG. 1. FIG. 37 is a sectional view taken along line B-B of FIG. 31. Incidentally, in the following description, the right side in FIGS. 30 to 32 and 34 to 36 will be referred to as "proximal," and the left side as "distal." Further, in FIG. 37, a magnitude-basis relationship between the curvature of the seal member and the curvature of each of nanobubbles is different from the actual relationship; more specifically, the nanobubbles are drawn in an exaggerated manner (to be comparatively larger) as compared to the seal member.

Next, a seventh embodiment of the method of producing an indwelling needle assembly, and the indwelling needle assembly produced thereby, according to the present invention will be described below. The following description will be centered on differences from the above-described embodiments, and descriptions of the same items therein shall be omitted.

The present embodiment is the same as the first embodiment, except for differences in the steps that are performed for producing the indwelling needle assembly.

Next, the method of producing the indwelling needle assembly 1 will be described below referring to FIGS. 30 to 36.

The method of producing the indwelling needle assembly 1 includes an immersion step (first step), an insertion step (second step), a drawing-up step (third step), a lubricant application step (fourth step), a reciprocation step (fifth step), an inner needle hub fixation step (sixth step), a seal member accommodation step (seventh step), a tube connection step (eighth step), and an outer needle hub fixation step (ninth step), wherein these steps are carried out sequentially.

<<1>> Immersion Step

Figure 30:
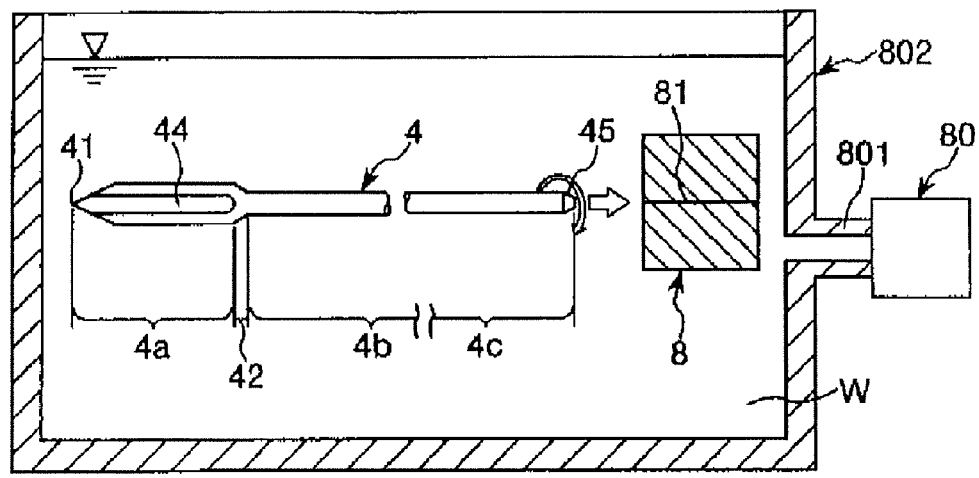
FIG. 30 is a drawing for sequentially illustrating steps (seventh embodiment) for producing the indwelling needle assembly shown in FIG. 1.

First, in this step, a nanobubble water production device 80 (for example, "BUVITAS," a product by KYOWAKISETSU Co., Ltd.) for producing nanobubble water W containing nanobubbles B, and a reservoir 802 connected to the nanobubble water production device 80 through a connecting pipe 801 are used (see FIG. 30). The nanobubble water W produced by the nanobubble water production device 80 flows through the connecting pipe 801 into the reservoir 802. As a result, the reservoir 802 is supplied with the nanobubble water W, whereupon the reservoir 802 becomes filled with the nanobubble water W.

In addition, a seal member 8 and an inner needle 4 are prepared. The seal member 8 is preliminarily formed with a slit 81 therein. This ensures that an operation of inserting the inner needle 4 (insertion operation), to be described later, can be carried out easily. Further, a proximal portion 45 of the inner needle 4 may be formed with a tapered part, where the outside diameter thereof decreases gradually in the proximal direction. Alternatively, the proximal portion 45 may have a simple flat surface.

Then, as shown in FIG. 30, the inner needle 4 and the seal member 8, which are yet to be assembled, are immersed in the reservoir 802 filled with the nanobubble water W.

<<2>> Insertion Step

Figure 31:
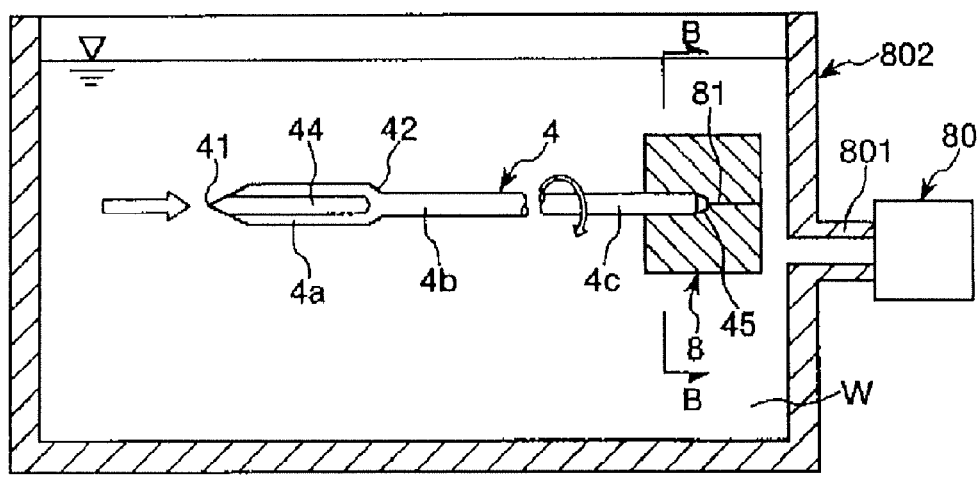
FIG. 31 is a drawing for sequentially illustrating the steps (seventh embodiment) for producing the indwelling needle assembly shown in FIG. 1.

As shown in FIG. 31, in the nanobubble water W, the inner needle 4 is inserted through (into) a slit 81 in the seal member 8, starting with a side opposite to the needle point 41, namely, starting with the proximal portion 45. In this instance, a multiplicity of nanobubbles B enter into the gap between the inner surface 811 of the slit 81 in the seal member 8 and the outer peripheral surface 48 of the inner needle 4 (see FIG. 37). Surface activity of the nanobubbles B facilitates insertion of the inner needle 4 into and through the seal member 8. In addition, the area of contact between the inner surface 811 of the slit 81 and the outer peripheral surface 48 of the inner needle 4 is reduced. More specifically, fine gaps 82 are generated between such surfaces, whereby insertion of the inner needle 4 into and through the seal member 8 is facilitated.

Further, the insertion operation can be carried out more easily, owing to the synergistic effect of the tapered part, which is provided at the proximal portion 45 of the inner needle 4, and the slit 81 that is formed preliminarily in the seal member 8.

Figure 32:
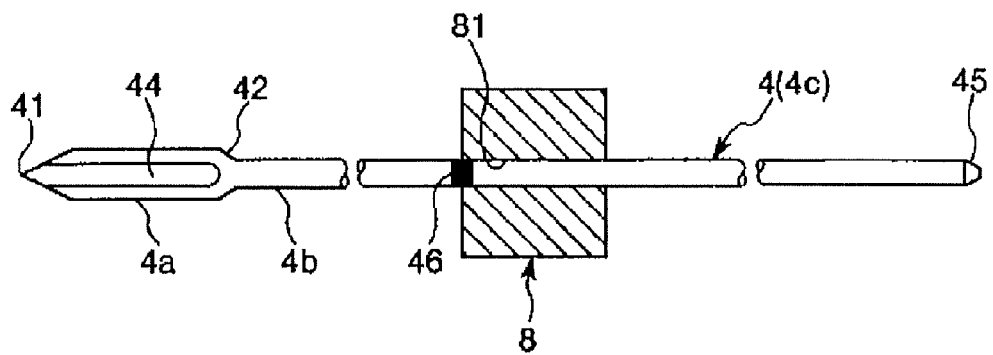
FIG. 32 is a drawing for sequentially illustrating the steps (seventh embodiment) for producing the indwelling needle assembly shown in FIG. 1.

When the inner needle 4 is pressed further in toward the proximal side, the proximal portion 45 reaches beyond the seal member 8 and protrudes toward the proximal side of the seal member 8 (see FIG. 32).

In addition, in this case, a predetermined position of a minimum outside diameter part 4c of the inner needle 4 is disposed inside the slit 81, thereby positioning the inner needle 4 relative to the seal member 8. Incidentally, as shown in FIG. 32, the minimum outside diameter part 4c of the inner needle 4 may be provided with a marker 46 thereon to facilitate positioning. The marker 46 may be provided, for example, at a portion of the inner needle 4 that corresponds to the distal end face (the end face on one side) of the seal member 8.

Conditions of the seal member 8, a compression member 30 and the inner needle 4, which are assembled together in this manner, will be referred to as an "inserted condition" (see FIG. 32).

In the aforementioned insertion step, the needle point 41 of the inner needle 4 is prevented securely from becoming worn as a result of making contact with the seal member 8 (the slit 81). Consequently, damage to the needle point 41 (for example, chipping of the cutting edge) can be securely prevented from occurring, or in other words, the needle point 41 can be protected assuredly.

Further, when the inner needle 4 is inserted into and through the seal member 8, the insertion operation may be conducted while the inner needle 4 is rotated about its axis. This makes the insertion operation easier to carry out.

<<3>> Drawing-up Step

Next, the inner needle 4 and the seal member 8 in the inserted condition are drawn up from the nanobubble water W.

<<4>> Lubricant Application Step

Figure 33:
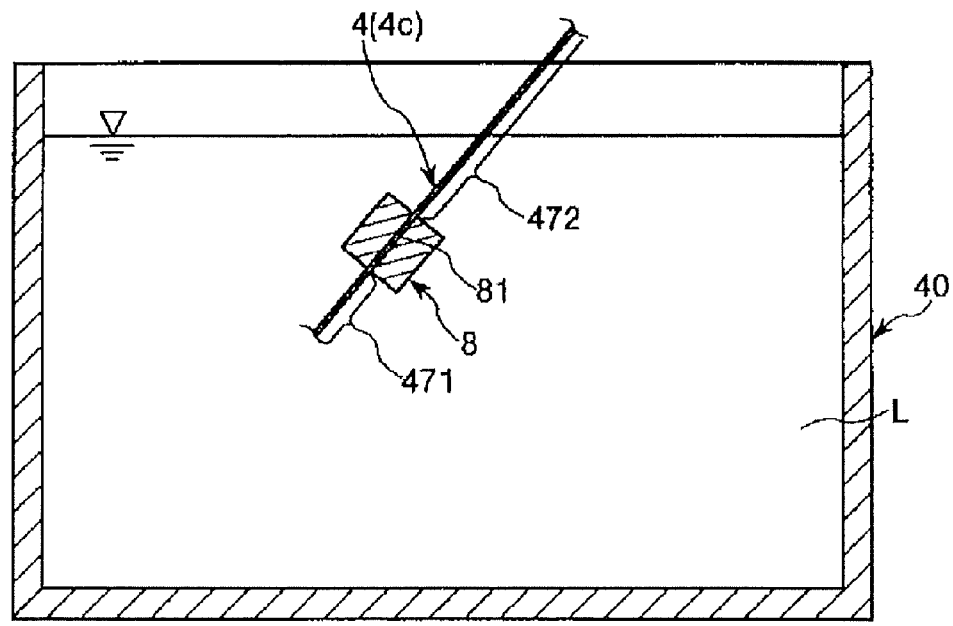
FIG. 33 is a drawing for sequentially illustrating the steps (seventh embodiment) for producing the indwelling needle assembly shown in FIG. 1.

Subsequently, a reservoir 40, which is filled with liquid lubricant (lubricating liquid) L, is prepared. Then, as shown in FIG. 33, the inner needle 4 and the seal member 8 in the inserted condition are immersed in the reservoir 40. Thus, by such an immersion method, the lubricant L can be applied (supplied) easily and assuredly to the portion of the inner needle 4 that protrudes from the seal member 8. Incidentally, the portion of the inner needle 4 that protrudes from the seal member 8 includes a distal-side part (distal-side protruding part 471) and a proximal-side part (proximal-side protruding part 472), with the seal member 8 being disposed therebetween (see FIG. 33). In addition, it is unnecessary for the proximal-side protruding part 472 to be entirely immersed in the lubricating liquid L, and it suffices if only a portion thereof near the seal member 8 is immersed.

Incidentally, the lubricant L is not particularly limited. Examples of usable lubricants include those consisting mainly of silicone, particularly, silicone oils, reactive silicones, and mixtures thereof. Reactive silicones are silicones that can be cured by heat or radiation. When a reactive silicone is used, silicone remains for a long time on the inner surfaces 811 of the slit 81 in the seal member 8, as well as on the surface (outer peripheral surface 48) of the inner needle 4, so that the effect of the lubricant L on reducing friction between the inner needle 4 and the seal member 8 is maintained. Further, the mixing ratio employed when mixing a silicone oil and a reactive silicone ("amount of silicone oil": "amount of reactive silicone") is not particularly limited. For example, the mixing ratio preferably is in the range from 1:9 to 9:1, and more preferably, from 2:8 to 8:2.

<<5>> Reciprocation Step

Next, the inner needle 4 and the seal member 8 in the inserted condition are drawn up (taken out) from the reservoir 40.

Figure 34:
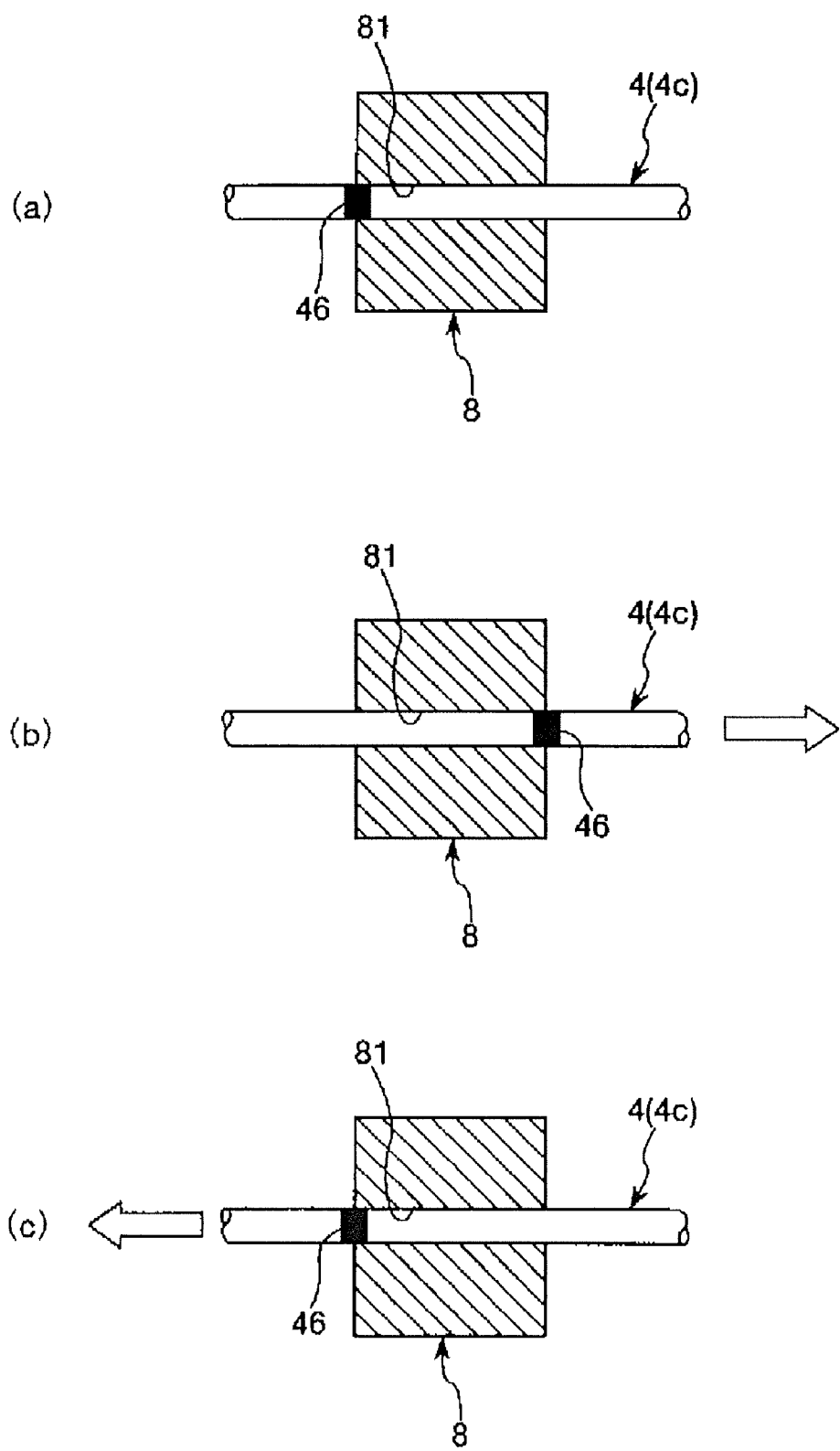
FIG. 34 shows drawings for sequentially illustrating the steps (seventh embodiment) for producing the indwelling needle assembly shown in FIG. 1.

Then, with an end portion of the inner needle 4 being gripped by one hand and while the seal member 8 is gripped by the other hand, the inner needle hub 5 is reciprocated along the axial direction of the inner needle 4 relative to the seal member 8, as shown in FIG. 34. This ensures that the lubricant L, which is deposited on the outer peripheral surfaces of the distal-side protruding part 471 and the proximal-side protruding part 472 of the inner needle 4, enters (penetrates) reliably into the slit 81. The lubricant L, having entered into the slit 81, makes it possible to securely reduce frictional resistance between the inner needle 4 and the seal member 8 (the slit 81) when the inner needle 4 is pulled out from the seal member 8, as mentioned above.

In addition, during the reciprocating operation, the marker 46 on the inner needle 4, which is located near the distal end face of the seal member 8 (see FIG. 34(a)), travels a distance so as to reach beyond the proximal end face (the end face on the other side) of the seal member 8 (see FIG. 34(b)). This enables the slit 81 to be securely supplied with the lubricant L, over an entire range thereof in the longitudinal direction. Therefore, frictional resistance can be reduced more assuredly. Further, by visually checking the marker 46, the distance traveled by the marker 46 can be ascertained.

In addition, during the reciprocating operation, the operation may be performed while rotating the inner needle 4 about its axis. This reduces sliding resistance between the inner needle 4 and the seal member 8 during the reciprocating operation, and therefore facilitates reciprocation thereof.

Besides, the number of times that the reciprocating operation is carried out is not particularly limited. For example, the number of times preferably is at least once, and more preferably, 1 to 5 times.

<<6>> Inner Needle Hub Fixation Step

Subsequently, an inner needle hub 5 having a protector 9 assembled (accommodated) therein, and the compression member 30 are prepared.

The compression member 30 is disposed so that the flange 302 thereof is located on the proximal side, whereas the inner needle 4 in the inserted condition is disposed so that the proximal portion 45 thereof is located on the proximal side. Disposed in this manner, the inner needle 4 in the inserted condition is inserted, proximal side first, into the compression member 30. Then, the compression member 30 is disposed at an intermediate portion of the minimum outside diameter part 4c of the inner needle 4, so that the seal member 8 is not accommodated within the compression member 30 (see FIG. 35).

Thereafter, the inner needle 4, with the compression member 30 disposed thereon as mentioned above, is inserted, proximal portion 45 first, into the inner needle hub 5 (the protector 9). As a result, the proximal portion 45 of the inner needle 4 passes through an inner needle passage 931 in the protector 9, to arrive at (reach) a projected part 512 of the inner needle hub 5. The proximal portion 45 of the inner needle 4 is inserted into a hole 513, and is affixed to the projected part 512, for example, by fitting. Consequently, the inner needle hub 5 and the inner needle 4 are assembled together, and the inner needle 4 is affixed to the inner needle hub 5 (see FIGS. 1 and 35).

<<7>> Seal Member Accommodation Step

Figure 35:
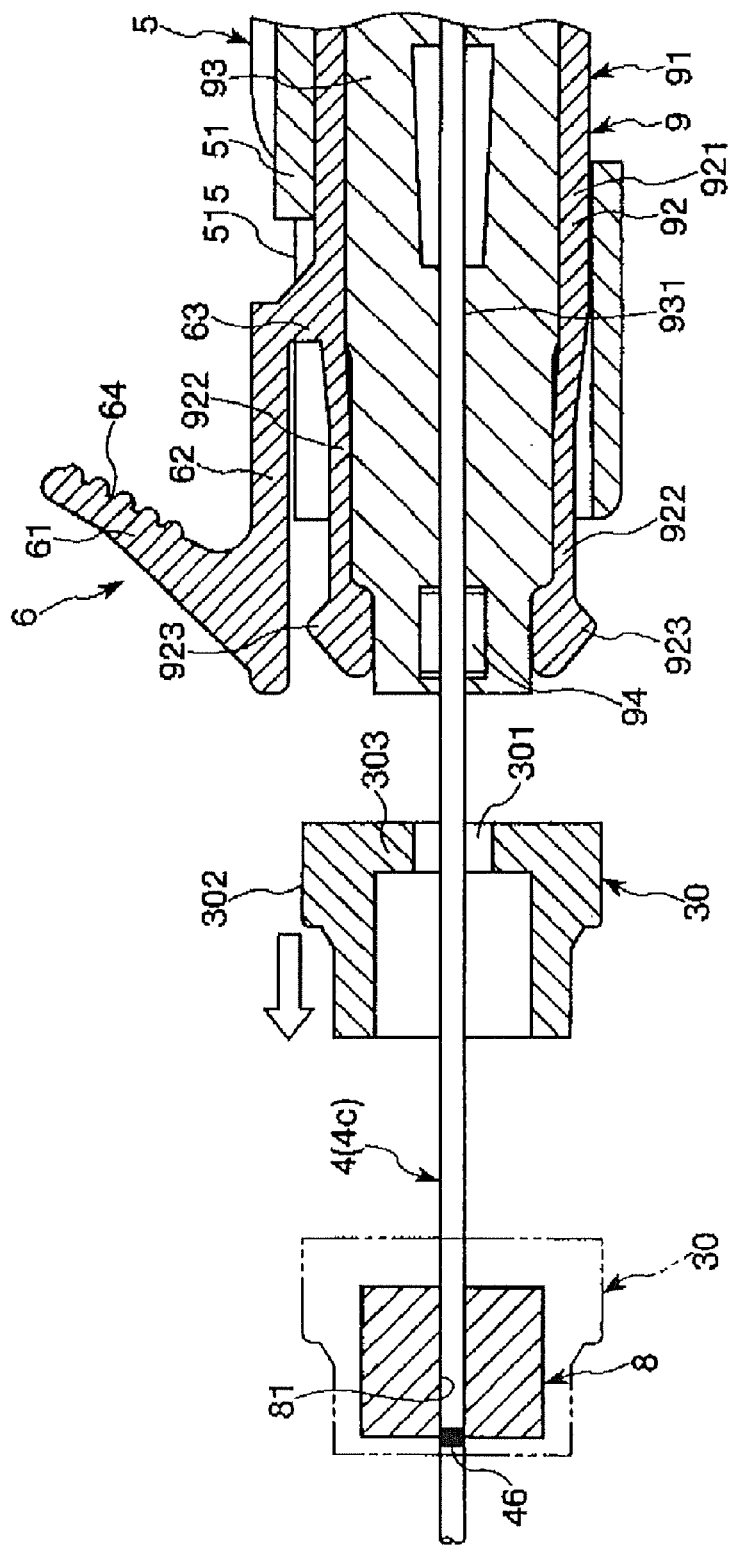
FIG. 35 is a drawing for sequentially illustrating the steps (seventh embodiment) for producing the indwelling needle assembly shown in FIG. 1.

Next, as shown in FIG. 35, the compression member 30 is moved in the distal direction along the inner needle 4, whereupon the seal member 8 becomes accommodated in the compression member 30 (refer to the part (compression member 30) indicated by the two-dotted chain line in FIG. 35), thereby resulting in a pressed-in condition.

<<8>> Tube Connection Step

Subsequently, a tube 7 having a connector 72 connected thereto, and an outer needle hub 3 are prepared.

Figure 36:
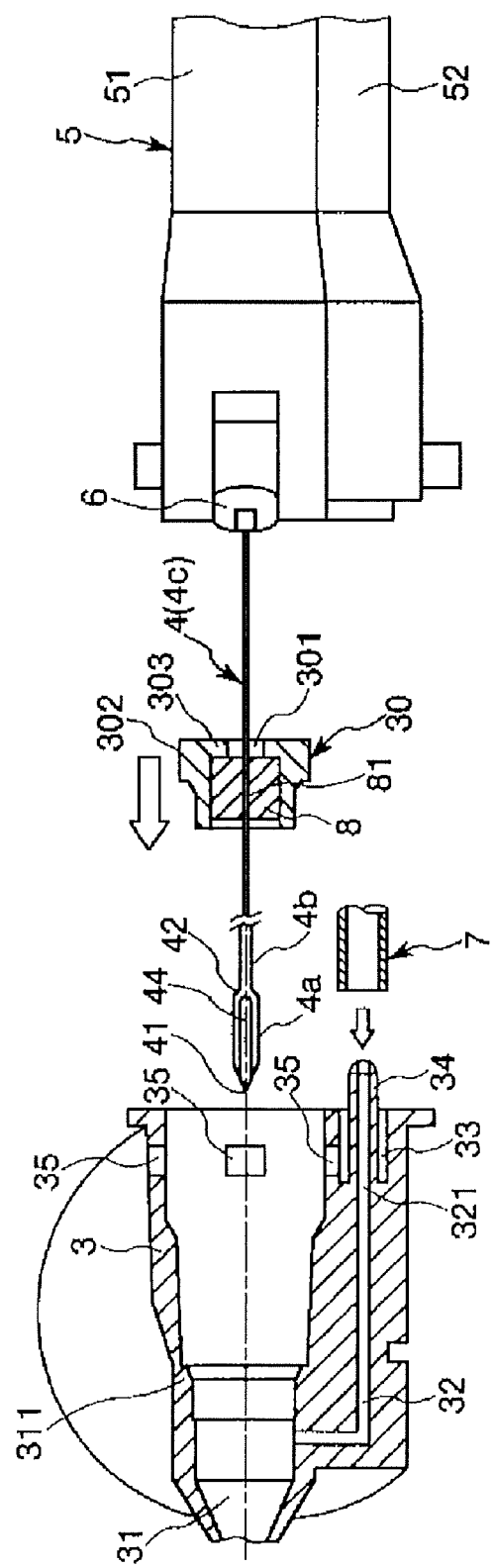
FIG. 36 is a drawing for sequentially illustrating the steps (seventh embodiment) for producing the indwelling needle assembly shown in FIG. 1.
Figure 37:
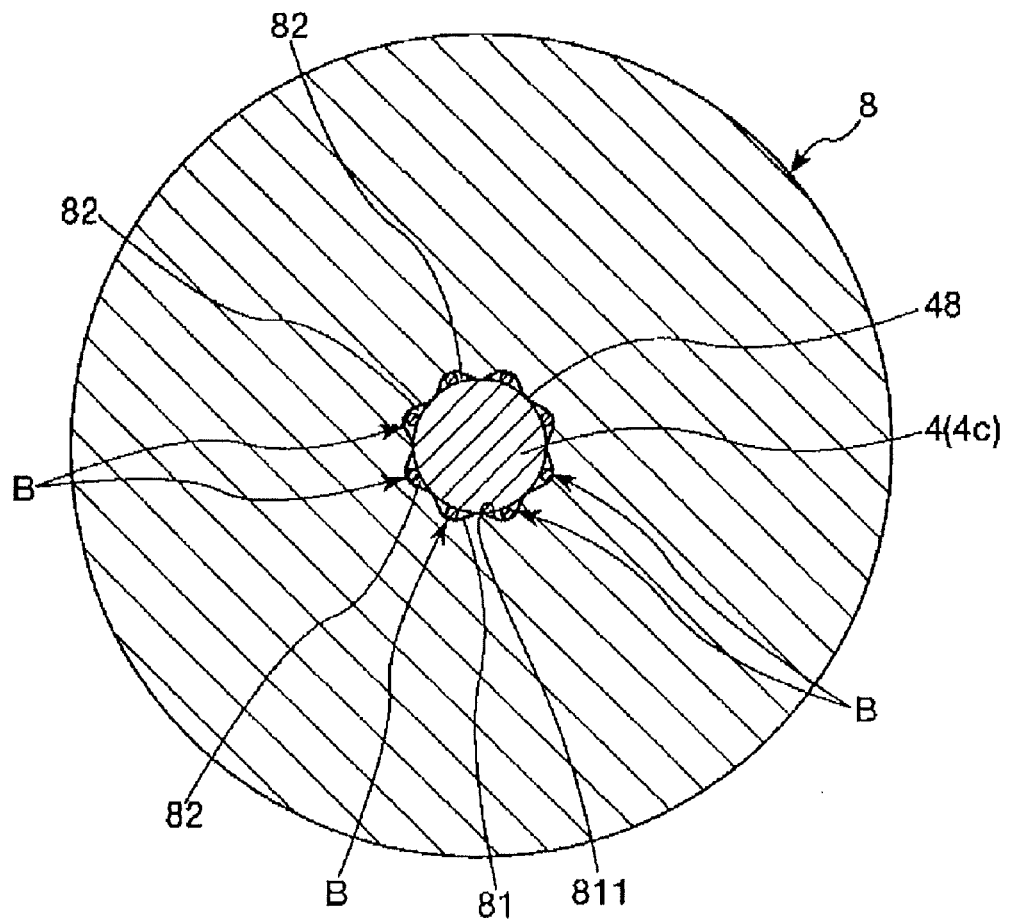
FIG. 37 is a sectional view taken along line B-B of FIG. 31.

An end portion of the tube 7, on a side opposite to the connector 72, is inserted into a recess 33 in the outer needle hub 3, whereupon the end portion is fitted onto a projected part 34 (see FIG. 36). This results in the tube 7 and the outer needle hub 3 becoming connected to each other.

<<9>> Outer Needle Hub Fixation Step

Next, the outer needle hub 3 with the tube 7 connected thereto is prepared. The outer needle hub 3 is accompanied by an outer needle 2, which is already affixed thereto.

While maintaining the positional relationship shown in FIG. 36 between the inner needle 4 and the seal member 8, in the inserted condition, the inner needle 4 is inserted with the proximal side thereof first into the outer needle hub 3, until the inner needle hub 5 abuts against the outer needle hub 3. This results in the inner needle 4 becoming accommodated in the outer needle 2. Also, the compression member 30 is fitted at the inside 31 of the outer needle hub 3, and the seal member 8 is affixed to the outer needle hub 3 through the compression member 30.

Thereafter, the tube 7 becomes accommodated in a tube accommodating part 52 of the inner needle hub 5.

Through the aforementioned steps, the indwelling needle assembly 1 is produced (assembled) assuredly.

In addition, the nanobubbles B have a bactericidal effect. Therefore, such nanobubbles B are suited for use in producing a medical implement, such as the indwelling needle assembly 1.

Further, in the indwelling needle assembly 1 in the assembled condition, the lubricant L is deposited in the slit 81 as well as on the outer peripheral surface 48 of the inner needle 4. Therefore, frictional resistance between the inner needle 4 and the seal member 8 can be reduced assuredly at a time when the inner needle 4 is pulled out from the seal member 8, in a condition where the blood vessel is punctured by the outer needle 2. As a result, the outer needle 2 can be moved smoothly, such that the indwelling needle assembly 1 is excellent in operability during the puncturing operation.

In addition, when the inner needle 4 is formed from a metallic material, as mentioned above, due to the presence of the lubricant L, slidability of the inner needle 4 relative to the seal member 8 is enhanced. Stated otherwise, frictional resistance between the seal member 8 and the inner needle 4 can be reduced more reliably. Consequently, excellent operability is ensured when the pulling-out operation is performed.

Further, although the seal member 8, which is formed preliminarily with the slit 81 therein, was used in the above-described insertion step, the invention is not limited by this feature. For example, a seal member 8, which is not yet formed with a slit 81 therein, may also be used. In this case, by inserting the inner needle 4 into and through the seal member 8 (i.e., causing the inner needle 4 to penetrate the seal member 8), a slit (through-hole) is formed therein.

In addition, the lubricant application step is not limited to applying the lubricant L by immersion in the lubricant L. For example, a method of applying the lubricant L by means of spraying, or by use of a dropping pipette or the like, may also be used.

Further, in the reciprocation step, reciprocation may be conducted while the inner needle 4 is swung to and fro.

While the method of producing an indwelling needle assembly, as well as the indwelling needle assembly according to the present invention, have been described above with reference to the embodiments shown in the drawings, the invention is not strictly limited by such embodiments. Configurations of the respective components may be replaced by other configurations, which can exhibit functions equivalent to the functions of the original configuration. Further, other arbitrary structures and/or steps may be added.

In addition, the indwelling needle assembly according to the present invention is not limited to being used in a state of insertion into a blood vessel. For example, the invention also is applicable to indwelling needle assemblies, which are used in a state of, for example, being inserted into an abdominal cavity, a thoracic cavity, a lymph vessel, a vertebral canal or the like.

Further, in the present invention, the shape of the slit in the seal member is not limited to a straight line. For example, the slit may be in the shape of a cross, the letter Y, the letter T (e.g., a non-right angled T), the letter H, or the like.

In addition, in the present invention, a cap may be provided, which is placed on the proximal portion of the outer needle hub after the inner needle is pulled out from the outer needle. This ensures that leakage of liquid from the proximal end of the outer needle hub can be prevented more securely. The cap may be formed integrally with the outer needle hub, or may be a body that is separate from the outer needle hub. Further, the method of fixing the cap to the outer needle hub may be any method, for example, a method based on friction, latching, or the like.

In addition, in the present invention, the protector is not limited to being configured as shown in the drawings, insofar as the protector can be detachably linked to the outer needle hub. In particular, protectors having various configurations can be used, insofar as they are capable of covering at least the needle point of the inner needle upon withdrawal of the inner needle from the outer needle.

Further, in the present invention, the connector provided at the end portion of the tube is not particularly limited. Examples of connectors that can be used include the needle-less connector described in Japanese Laid-Open Patent Publication No. 2005-261931, and a three-way cock.

In addition, in the present invention, the component part provided at the end portion of the tube is not limited to the aforementioned connector. For example, the component part may comprise a cap, an air filter, or the like.

Further, in the indwelling needle assembly according to the present invention, the connector, the cap, and the air filter may be attached in a replaceable manner to the end portion of the tube, as required.

Industrial Applicability

One method of producing an indwelling needle assembly according to the present invention is a method of producing an indwelling needle assembly formed by assembling together an inner needle having a sharp needle point only at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out, the method of producing the indwelling needle assembly including: an insertion step for inserting the inner needle, with a side opposite to the needle point first, into and through the seal member so as to obtain an inserted condition; a lubricant application step for applying, in the inserted condition, lubricant to an outer peripheral surface of at least a portion of the inner needle that protrudes from the seal member; and a reciprocation step for reciprocating at least one time the inner needle in an axial direction thereof relative to the seal member, so as to cause the lubricant to penetrate inside of the seal member. Therefore, in the insertion step, wearing of the needle point of the inner needle due to making contact with the seal member is securely prevented from occurring. As a result, damage to the needle point (for example, chipping of the cutting edge) can securely be prevented from occurring. Namely, the needle point can be protected assuredly. In addition, since the indwelling needle assembly is produced through the lubricant application step and the reciprocation step, in the assembled condition the indwelling needle assembly has the lubricant deposited in the inside of the seal member, as well as on the outer surface of the inner needle. This makes it possible, in the indwelling needle assembly, to securely reduce frictional resistance between the inner needle and the seal member when the inner needle is pulled out from the seal member. Consequently, excellent operability is realized during the pulling-out operation. Further, if the seal member is preliminarily formed with a slit therein, during the insertion step, insertion can be carried out easily.

In addition, another method of producing an indwelling needle assembly according to the present invention is a method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom, the method of producing the indwelling needle assembly including: a jig insertion step for inserting a jig that permits the inner needle to be inserted therethrough into and through the seal member, so as to obtain a jig-inserted condition; a lubricant application step for applying lubricant to at least a portion of the outer peripheral surface of the inner needle that corresponds to the seal member when the inner needle and the seal member are assembled together; an inner needle insertion step for inserting the inner needle, with the lubricant applied thereto, into and through the inside of the jig in the jig-inserted condition; and a jig pulling-out step for moving the jig along an axial direction relative to the inner needle and the seal member in order to pull out the jig. Accordingly, when the inner needle is inserted into and through the seal member to assemble them together, the jig is preliminarily inserted into and through the seal member, whereupon the inner needle is inserted into and through the seal member by way of the jig. This ensures that wearing of the needle point of the inner needle due to making contact with the seal member is securely prevented, namely, the needle point can be protected assuredly, as compared to a case where the inner needle is inserted directly, with its needle point first, into the seal member during assembly of the indwelling needle assembly. Further, since the indwelling needle assembly is assembled (produced) by means of the lubricant application step and the jig pulling-out step, the indwelling needle assembly in the assembled condition has a lubricant deposited in the interior of the seal member and on the outer surface of the inner needle. This makes it possible, in the indwelling needle assembly, to securely reduce frictional resistance between the inner needle and the seal member when the inner needle is pulled out from the seal member. Consequently, operability during the pulling-out operation is excellent. In addition, if the seal member is formed preliminarily with a slit therein, the insertion operation can be carried out easily when the inner needle is inserted into and through the seal member.

A further method of producing an indwelling needle assembly according to the present invention is a method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, and having a slit therein which permits the inner needle to be inserted therethrough, the slit exhibiting a sealing function when the inner needle is pulled out therefrom, the method of producing the indwelling needle assembly including: an insertion step for inserting the inner needle, with a side opposite to the needle point first, into and through the slit to obtain an inserted condition; a slit opening step for opening the slit in the inserted condition; and a lubricant supplying step for supplying a lubricant into the opened slit to apply the lubricant to the inner surface of the slit and to a portion of the outer peripheral surface of the inner needle that is located inside the slit. Accordingly, in the insertion step, the inner needle is inserted, with the side opposite to the needle point first, into the seal member, thereby obtaining an inserted condition. Therefore, wearing of the needle point of the inner needle due to making contact with the seal member (the slit) is securely prevented from occurring. This ensures that damage to the needle point (for example, chipping of the cutting edge) can securely be prevented from occurring, whereby the needle point can be protected assuredly. In addition, in the assembled condition, the indwelling needle assembly has a lubricant deposited in the slit as well as to the outer surface of the inner needle. This makes it possible to securely reduce frictional resistance between the inner needle and the seal member at a time when the inner needle is pulled out from the seal member, in the condition where the outer needle has securely punctured a blood vessel. Consequently, the outer needle can be moved smoothly, and during the puncturing operation, the indwelling needle assembly is excellent in operability.

Yet another method of producing an indwelling needle assembly according to the present invention is a method of producing an indwelling needle assembly formed by assembling together an inner needle having a sharp needle point only at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom, the method of producing the indwelling needle assembly including: an immersion step for immersing the inner needle and the seal member in nanobubble water containing nanobubbles; an insertion step for inserting, in the nanobubble water, the inner needle, with a side opposite to the needle point first, into and through the seal member so as to obtain an inserted condition; a pulling-up step for pulling the inner needle and the seal member in the inserted condition up from the nanobubble water; a lubricant application step for applying, in the inserted condition, lubricant to the outer peripheral surface of at least a portion of the inner needle that protrudes from the seal member; and a reciprocation step for reciprocating at least one time the inner needle in an axial direction thereof relative to the seal member, so as to cause the lubricant to penetrate inside of the seal member. Accordingly, in the insertion step, wearing of the needle point of the inner needle due to making contact with the seal member is securely prevented from occurring. This ensures that damage to the needle point (for example, chipping of the cutting edge) can securely be prevented from occurring, namely, the needle point can be protected assuredly. In addition, at a time of obtaining the inserted condition, a multiplicity of nanobubbles enter into the gap between the seal member and the outer peripheral surface of the inner needle, so that the operation (insertion operation) is facilitated as a result of surface activity of the nanobubbles. In addition, since the indwelling needle assembly is produced through the lubricant application step and the reciprocation step, the indwelling needle assembly in the assembled condition has a lubricant applied to the inside of the seal member as well as to the outer surface of the inner needle. This makes it possible, in the indwelling needle assembly, to securely reduce frictional resistance between the inner needle and the seal member at a time when the inner needle is pulled out from the seal member. Consequently, excellent operability is ensured during the pulling-out operation. Further, if the seal member is formed preliminarily with a slit therein, when the insertion step is performed, insertion can be carried out easily.

Accordingly, the method of producing an indwelling needle assembly according to the present invention has industrial applicability.

The invention claimed is:

1. A method of producing an indwelling needle assembly formed by assembling together an inner needle having a sharp needle point only at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out, the method of producing the indwelling needle assembly comprising:
an insertion step for inserting the inner needle, with a side opposite to the needle point first, into and through the seal member so as to obtain an inserted condition;
a lubricant application step for applying, in the inserted condition, lubricant to an outer peripheral surface of at least a portion of the inner needle that protrudes from the seal member; and
a reciprocation step for reciprocating at least one time the inner needle in an axial direction thereof relative to the seal member, so as to cause the lubricant to penetrate inside of the seal member;
wherein, in the reciprocation step, the portion of the inner needle that corresponds to one end face of the seal member travels a distance sufficient to pass beyond the other end face of the seal member; and
further comprising, after the reciprocation step, an outer needle hub fixation step for fixing to the outer needle hub the seal member in the inserted condition and thereby forming the indwelling needle assembly.

2. The method of producing the indwelling needle assembly according to claim 1, wherein in the insertion step, insertion of the inner needle into and through the seal member is performed while the inner needle is rotated about its axis.

3. The indwelling needle assembly produced by the method according to claim 1.

4. The method of producing the indwelling needle assembly according to claim 1, comprising, between the insertion step and the lubricant application step, an inner needle hub fixation step for fixing the inner needle hub to the proximal portion of the inner needle in the inserted condition.

5. The method of producing the indwelling needle assembly according to claim 1, wherein the inner needle includes a marker and movement of the marker corresponds to movement of the inner needle, and the method further comprising ascertaining the distance traveled by the inner needle during the reciprocation step based upon movement of the marker.

6. A method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom, the method of producing the indwelling needle assembly comprising:
a jig insertion step for inserting a jig that permits the inner needle to be inserted therethrough into and through the seal member, so as to obtain a jig-inserted condition;
a lubricant application step for applying lubricant to at least a portion of the outer peripheral surface of the inner needle that corresponds to the seal member when the inner needle and the seal member are assembled together;
an inner needle insertion step for inserting the inner needle, with the lubricant applied thereto, into and through the inside of the jig in the jig-inserted condition; and
a jig pulling-out step for moving the jig along an axial direction relative to the inner needle and the seal member in order to pull out the jig.

7. A method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom, the method of producing the indwelling needle assembly comprising:

a jig insertion step for inserting a jig that permits the inner needle to be inserted therethrough into and through the seal member, so as to obtain a jig-inserted condition;

an inner needle insertion step for inserting the inner needle into and through the inside of the jig in the jig-inserted condition;

a lubricant application step for filling a gap between the inside of the jig and the inner needle with a lubricant, so as to apply the lubricant to at least a portion of the outer peripheral surface of the inner needle that corresponds to the seal member when the inner needle and the seal member are assembled together; and a jig pulling-out step for moving the jig along an axial direction thereof relative to the inner needle and the seal member in order to pull out the jig.

8. A method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom, the method of producing the indwelling needle assembly comprising:

a jig insertion step for inserting a jig that permits the inner needle to be inserted therethrough into and through the seal member, so as to obtain a jig-inserted condition;

a lubricant filling step for filling the inside of the jig with a lubricant;

a lubricant application step for inserting the inner needle into and through the inside of the jig, which is in the jig-inserted condition and filled with the lubricant, so as to apply the lubricant to at least a portion of the outer peripheral surface of the inner needle that corresponds to the seal member when the inner needle and the seal member are assembled together; and a jig pulling-out step for moving the jig along an axial direction relative to the inner needle and the seal member in order to pull out the jig.

9. A method of producing an indwelling needle assembly formed by assembling together an inner needle having a sharp needle point at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, and having a slit that permits the inner needle to be inserted therethrough, the slit exhibiting a sealing function when the inner needle is pulled out therefrom, the method of producing the indwelling needle assembly comprising:

an insertion step for inserting the inner needle, with a side opposite to the needle point first, into and through the slit to obtain an inserted condition;

a slit opening step for opening the slit in the inserted condition; and a lubricant supplying step for supplying a lubricant into the opened slit to apply the lubricant to the inner surface of the slit and to a portion of the outer peripheral surface of the inner needle that is located inside the slit; and further comprising, after the reciprocation step, an outer needle hub fixation step for fixing to the outer needle hub the seal member in the inserted condition and thereby forming the indwelling needle assembly.

10. The method of producing the indwelling needle assembly according to claim 9, wherein in the insertion step, insertion of the inner needle into and through the seal member is carried out while rotating the inner needle about its axis.

11. A method of producing an indwelling needle assembly formed by assembling together an inner needle having a sharp needle point only at a tip thereof, an inner needle hub fixed to a proximal portion of the inner needle, a hollow outer needle that permits the inner needle to be inserted therethrough, an outer needle hub fixed to a proximal portion of the outer needle, and a seal member made from an elastic material provided on the outer needle hub, for permitting the inner needle to be inserted therethrough, and exhibiting a sealing function when the inner needle is pulled out therefrom, the method of producing the indwelling needle assembly comprising:

an immersion step for immersing the inner needle and the seal member in nanobubble water containing nanobubbles;

an insertion step for inserting, in the nanobubble water, the inner needle, with a side opposite to the needle point first, into and through the seal member so as to obtain an inserted condition;

a pulling-up step for pulling the inner needle and the seal member in the inserted condition up from the nanobubble water;

a lubricant application step for applying, in the inserted condition, lubricant to the outer peripheral surface of at least a portion of the inner needle that protrudes from the seal member; and a reciprocation step for reciprocating at least one time the inner needle in an axial direction thereof relative to the seal member, so as to cause the lubricant to penetrate inside of the seal member; and further comprising, after the reciprocation step, an outer needle hub fixation step for fixing to the outer needle hub the seal member in the inserted condition and thereby forming the indwelling needle assembly.

* * * * *